United States Patent
Rosen et al.

(10) Patent No.: US 11,198,680 B2
(45) Date of Patent: Dec. 14, 2021

(54) RHO KINASE INHIBITOR BA-1049 (R) AND ACTIVE METABOLITES THEREOF

(71) Applicant: BioAxone BioSciences, Inc., Boston, MA (US)

(72) Inventors: Kenneth M. Rosen, Milton, MA (US); Matthew D. Abbinanti, Westford, MA (US); Joerg Ruschel, Cambridge, MA (US); Lisa McKerracher, Boston, MA (US); Lisa Bond Moritz, Burtonsville, MD (US)

(73) Assignee: BioAxone BioSciences, Inc., Boston, MA (US)

(*) Notice: Subject to any disclaimer, the term of this patent is extended or adjusted under 35 U.S.C. 154(b) by 0 days.

(21) Appl. No.: 16/735,359

(22) Filed: Jan. 6, 2020

(65) Prior Publication Data
US 2020/0199105 A1    Jun. 25, 2020

Related U.S. Application Data

(60) Division of application No. 15/988,736, filed on May 24, 2018, now Pat. No. 10,526,313, which is a
(Continued)

(51) Int. Cl.
*C07D 401/12* (2006.01)
*C07C 55/14* (2006.01)
(Continued)

(52) U.S. Cl.
CPC ........ *C07D 401/12* (2013.01); *A61K 31/4545* (2013.01); *A61K 31/4725* (2013.01); *A61K 31/551* (2013.01); *A61K 45/06* (2013.01); *C07B 59/002* (2013.01); *C07C 55/14* (2013.01); *C07B 2200/05* (2013.01); *C07B 2200/07* (2013.01)

(58) Field of Classification Search
CPC .............................. C07D 401/12; A61K 45/06
See application file for complete search history.

(56) References Cited

U.S. PATENT DOCUMENTS 3,539,573 A    11/1970    Hunziker et al.
4,584,303 A    4/1986    Huang et al.
(Continued)

FOREIGN PATENT DOCUMENTS

CA    2304981 A1    5/1999
CA    2342251 A1    3/2000
(Continued)

OTHER PUBLICATIONS

Alexopoulos et al. "Design and synthesis of novel biologically active thrombin receptor non-peptide mimetics based on the pharmacophoric clusterPhe/Arg/NH2 of the Ser42-Phe-Leu-Leu-Arg46 motif sequence: platelet aggregation and relaxant activities," 2004, J. Med. Chem. 47(13):3338-33352.
(Continued)

*Primary Examiner* — San Ming R Hui
(74) *Attorney, Agent, or Firm* — Troutman Pepper Hamilton Sanders LLP

(57) ABSTRACT

BA-1049 (R) and its active metabolite are disclosed. Also disclosed are pharmaceutical formulations containing BA-1049 (R) or its active metabolite.

2 Claims, 28 Drawing Sheets

Specification includes a Sequence Listing.

BA-1049 (R)

Fasudil

Related U.S. Application Data continuation of application No. 15/591,039, filed on May 9, 2017, now Pat. No. 10,106,525.

(60) Provisional application No. 62/437,181, filed on Dec. 21, 2016.

(51) Int. Cl.
*C07B 59/00* (2006.01)
*A61K 31/4725* (2006.01)
*A61K 45/06* (2006.01)
*A61K 31/4545* (2006.01)
*A61K 31/551* (2006.01)

(56) References Cited

U.S. PATENT DOCUMENTS

| | | | |
|---|---|---|---|
| 4,678,783 A | 7/1987 | Hidaka et al. | |
| 4,798,897 A | 1/1989 | Hidaka et al. | |
| 4,849,521 A | 7/1989 | Kudzma et al. | |
| 4,857,301 A | 8/1989 | Czarniecki et al. | |
| 4,866,077 A | 9/1989 | Bogeso et al. | |
| 4,933,353 A | 6/1990 | Jensen et al. | |
| 4,997,834 A | 3/1991 | Muro et al. | |
| 5,478,838 A | 12/1995 | Arita et al. | |
| 5,496,846 A | 3/1996 | Wilson et al. | |
| 5,741,792 A | 4/1998 | Kimball et al. | |
| 5,906,819 A | 5/1999 | Kaibuchi et al. | |
| 6,020,352 A | 2/2000 | Kapin et al. | |
| 6,140,333 A | 10/2000 | Tsuchiya et al. | |
| 6,169,097 B1 | 1/2001 | Janssens et al. | |
| 6,218,410 B1 | 4/2001 | Uehata et al. | |
| 6,297,228 B1 | 10/2001 | Clark | |
| 6,506,901 B2 | 1/2003 | Steffan et al. | |
| 6,545,022 B1 | 4/2003 | Bryans et al. | |
| 6,906,061 B2 | 6/2005 | Uehata et al. | |
| 7,169,783 B2 | 1/2007 | McKerracher et al. | |
| 7,199,147 B2 | 4/2007 | Imazaki et al. | |
| 7,572,913 B2 * | 8/2009 | McKerracher | A61P 25/16 546/141 |
| 8,957,003 B2 | 2/2015 | Wu et al. | |
| 9,687,483 B2 | 6/2017 | McKerracher et al. | |
| 10,106,525 B2 | 10/2018 | Rosen et al. | |
| 10,149,856 B2 | 12/2018 | Rosen et al. | |
| 2003/0120511 A1 | 6/2003 | Legnini | |
| 2011/0112035 A1 | 5/2011 | Jorgensen et al. | |
| 2014/0256941 A1 | 9/2014 | Liu et al. | |
| 2015/0297643 A1 | 10/2015 | McKerracher | |
| 2016/0016914 A1 | 1/2016 | Ladziata et al. | |
| 2016/0213664 A1 | 7/2016 | McKerracher et al. | |
| 2017/0313680 A1 | 11/2017 | Rosen et al. | |

FOREIGN PATENT DOCUMENTS

| | | |
|---|---|---|
| CA | 2443108 A1 | 10/2002 |
| CA | 2325842 C | 8/2007 |
| JP | 2007523202 A | 8/2007 |
| JP | 2011530518 A | 12/2011 |
| WO | 2003042174 A1 | 5/2003 |
| WO | 2005080394 A1 | 9/2005 |
| WO | 2010017150 A1 | 2/2010 |
| WO | 2015165341 A1 | 11/2015 |
| WO | 2018022927 A1 | 2/2018 |
| WO | 2018118109 A1 | 6/2018 |

OTHER PUBLICATIONS

Berge et al. "Pharmaceutical Salts", 1977, Journal of Pharmaceutical Sciences 66(1):1-19.
Borikova et al. "Rho Kinase Inhibition Rescues the Endothelial Cell Cerebral Cavernous Malformation Phenotype" 2010, J. Biol. Chem. 285(16)11760-11764.
Concert Pharmaceuticals Inc., Precision Deuterium Chemistry Backgrounder, Internet Citation [Online], 2007, p. 1-6, URL, http://www.webcitation.org/5e81SGCnl.
Del Peso et al. "Rho proteins induce metastatic properties in vivo," 1997, Oncogene. 15(25):3047-3057.
Demiryurek et al. "Lack of association between the Thr431Asn and Arg83Lys polymorphisms of the ROCK2 gene and diabetic retinopathy," 2010, Curr Eye Res. 35(12):1128-1134.
Eldawoody et al. "Simplified experimental cerebral aneurysm model in rats: comprehensive evaluation of induced aneurysms and arterial changes in the circle of Willis," 2009, Brain Res. 1300:159-168.
FDA, Guidance for Industry "Estimating the Maximum Safe Starting Dose in Initial Clinical Trials for Therapeutics in Adult Healthy Volunteers," (2005) (30 pages).
Fukumoto et al. "Acute vasodilator effects of a Rho-kinase inhibitor, fasudil, in patients with severe pulmonary hypertension," 2005, Heart 91:391-392.
Green et al. "Design, Synthesis and Structure —Activity Relationshipa of Pyridine-based Rho Kinase (ROCK) Inhibitors" 2015, Journal of Medicinal Chemistry 58:5028-5037.
Hahmann et al. "Rho-kinase inhibitors as therapeutics: from pan inhibition to isoform selectivity," 2010, Cell. Mol. Life Sci. 67:171-177.
Hara et al. "Protein kinase inhibition by fasudil hydrochloride promotes neurological recovery after spinal cord injury in rats" 2000, J Neurosurg (Spine 1). 93:94-101.
Haskins "The Application of Stable Isotopes in Biomedical Research" 1982, Bionedical Mass Spectrometry 9 (7):269-277.
http://ehealthme.com/drug_side_effects/Fasudil-Hydrochloride-1268381 (3 pages).
http://rsb.info.nih.gov/ij/docs/menus/analyze.html (14 pages).
https://clinicaltrials.gov/ct2/show/NCT02317627?term-kd025&rank=2 (4 pages).
International Search Report and Written Opinion for PCT/US2017/031836 dated Aug. 30, 2017.
Ishizaki et al. "p160ROCK, a Rho-associated coiled-coil forming protein kinase, works downstream of Rho and induces focal adhesions," 1997, FEBS Lett. 404(2-3):118-124.
Ishizaki et al. "Pharmacological Properties of Y-27632, a Specific Inhibitor of Rho-Associated Kinases" 2000, Mal. Pharmacol 57:976-983.
Ishizaki et al. "The small GTP-binding protein Rho binds to and activates a 160 kDa Ser/Thr protein kinase homologous to myotonic dystrophy kinase," 1996, EMBO. 15(8):1885-1893.
Jacobs et al.,"The Structure of Dimeric ROCKI Reveals the Mechanism for Ligand Selectivity," 2006, J. Biolog. Chem. 281(1):260-268.
Jick et al.,"Statins and the risk of dementia," 2000, Lancet. 356(9242):1627-1631.
Kast et al. "Cardiovascular effects of a novel potent and highly selective azaindole-based inhibitor of Rho-kinase," 2007, Brit. J. Pharmacol. 152:1070-1080.
Kato et al., "Statin blocks Rho/Rho-kinase signalling and disrupts the actin cytoskeleton: relationship to enhancement of LPS-mediated nitric oxide synthesis in vascular smooth muscle cells," Biochim Biophys Acta. 1689(3):267-72 (2004).
Lee et al., "Neurodegenerative Tauopathies," Annu Rev Neurosci. 24:1121-59 (2001).
Lee et al., "Selective ROCK2 inhibition in focal cerebral ischemia." Ann. Clin. Transl. Neurol. 1(1):2-14 (2014).
Leemhuis et al., "The protein kinase A inhibitor H89 acts on cell morphology by inhibiting Rho kinase," J. Pharmacol. Exp. Ther. 300(3):1000-7 (2002).
McGeer et al., "Anti-inflammatory drugs and Alzheimer disease," Lancet. 335(8696): 1037 (1990).
McKerracher et al., "Identification of myelin-associated glycoprotein as a major myelin-derived inhibitor of neurite growth," Neuron. 13(4):805-11 (1994).
Mertsch et al., "Opposing Signaling of ROCK1 and ROCK2 Determines the Switching of Substrate Specificity and the Mode of Migration of Glioblastoma Cells," Mol. Neurobiol. 49:900-915 (2014).

(56) References Cited

OTHER PUBLICATIONS

Nakagawa et al., "ROCK-I and ROCK-II, two isoforms of Rho-associated coiled-coil forming protein serine/threonine kinase in mice." FEBS. Lett. 392(2):189-93 (1996).

Newell-Litwa et al., "ROCK1 and 2 differentially regulate actomyosin organization to drive cell and synaptic polarity," J Cell Biol. 210(2)225-242 (2015).

O'Driscoll "Swapping Selected Hydrogen Atoms for Deuterium could be a fast route to making safe, longer-lasting Drugs" Mar. 9, 2009, Chemistry & Industry, p. 24-26.

Pelosi et al., "ROCK2 and Its Alternatively Spliced Isoform ROCK2m Positively Control the Maturation of the Myogenic Program," Mol. Cell. Biol. 27(17):6163-6176 (2007).

Rikitake et al., "Inhibition of Rho Kinase (ROCK) Leads to Increased Cerebral Blood Flow and Stroke Protection," Stroke. 36(10):2251-2257 (2005).

Sayas et al., "Glycogen synthase kinase-3 is activated in neuronal cells by Galpha12 and Galpha13 by Rho-independent and Rho-dependent mechanisms," J. Neurosci. 22(16):6863-75 (2002).

Shi et al., "Distinct roles for ROCK1 and ROCK2 in the regulation of cell detachment." Cell Death and Disease 4:e483 (2013).

Shi et al., "Rho Kinases in Cardiovascular Physiology and Pathophysiology: The Effect of Fasudil," J. Cardiovasc. Pharmacol 62:341-354 (2013).

Tosaka "Research on the causes and pathology of cerebral vasospasm" 2003, Kitakanto Med J, 2003, vol. 53 (1):99-100 (with English translation).

Weggen et al., "A subset of NSAIDs lower amyloidogenic Abeta42 independently of cyclooxygenase activity," Nature. 414(6860):212-6 (2001).

Wibberley et al., "Expression and functional role of Rho-kinase in rat urinary bladder smooth muscle," Br. J. Pharmacol. 138(5):757-66 (2003).

Yi et al., "Photoactivation of hypericin decreases the viability of RINm5F insulinoma cells through reduction in JNK/ERK phosphorylation and elevation of caspase-9/caspase-3 cleavage and Bax-to-Bcl-2 ratio." Biosci Rep. 35:1-13 (2015).

Zhao et al., "Efficacy and safety of fasudil in patients with subarachnoid hemorrhage: final results of a randomized trial of fasudil versus nimodipine," Neurol. Med. Chir. 51:679-683 (2011).

Zhou et al., "Nonsteroidal anti-inflammatory drugs can lower amyloidogenic Abeta42 by inhibiting Rho," Science. 302 (5648):1215-7 (2003).

\* cited by examiner

Fasudil

1-Hydroxy-BA-1049

BA-1049 (R)

SLx-2119 (KD-025)

Scheme 1:

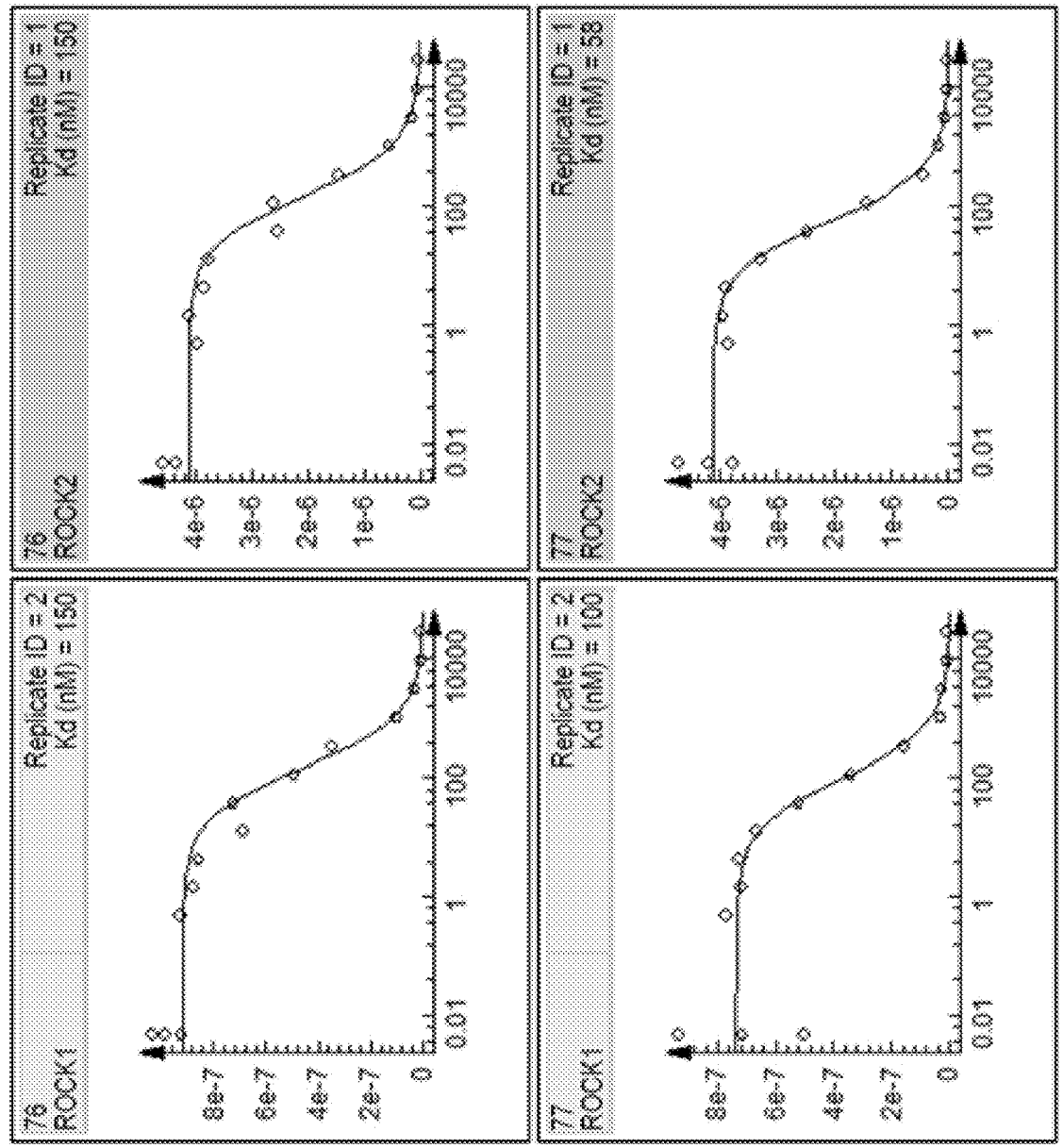

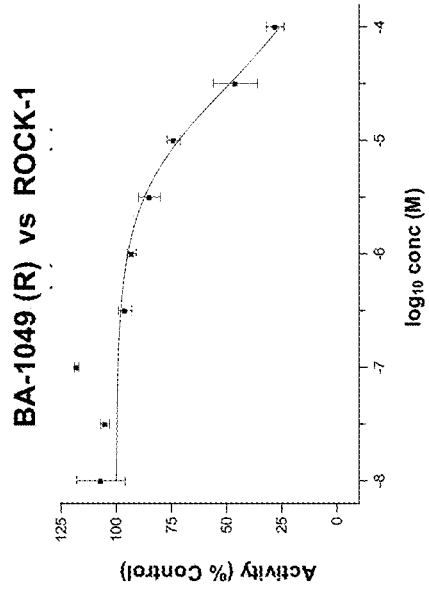
Fig. 7C
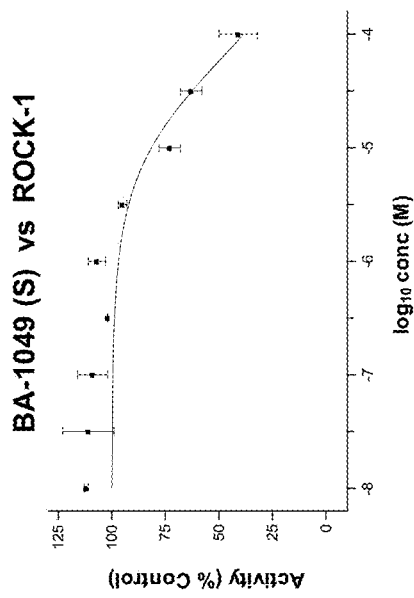
Fig. 7A
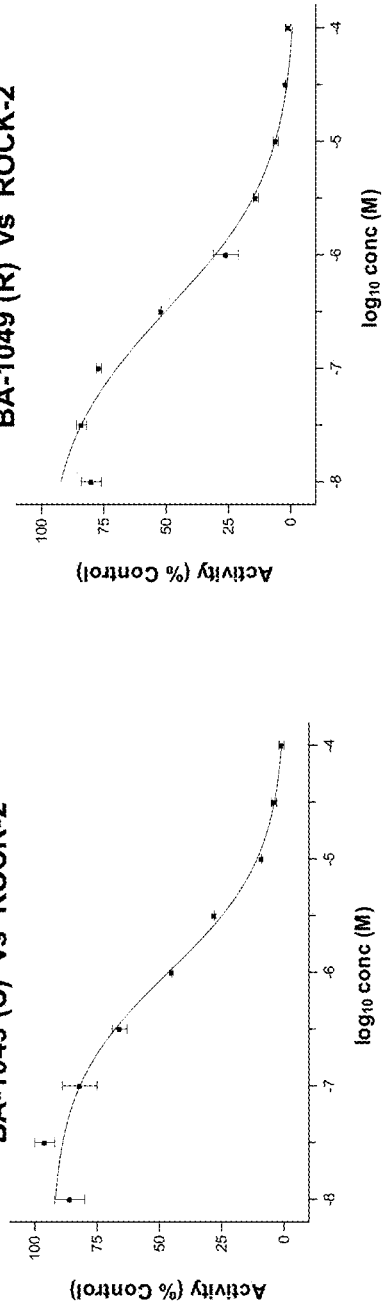
Fig. 7D
Fig. 7B

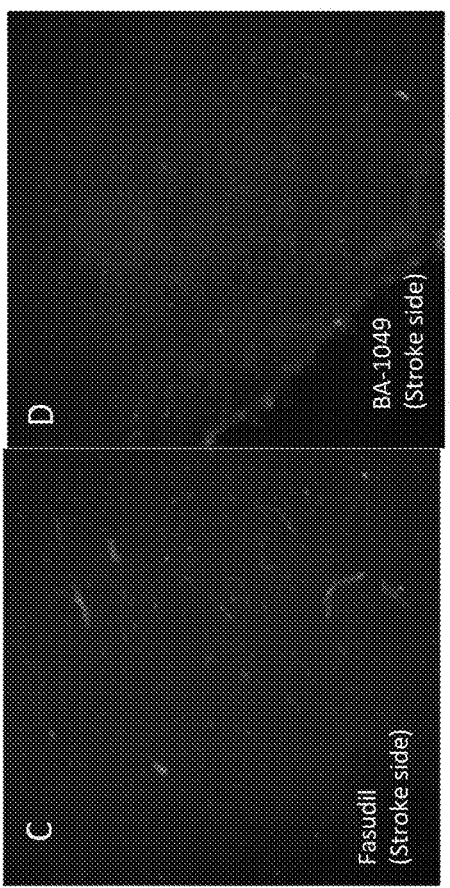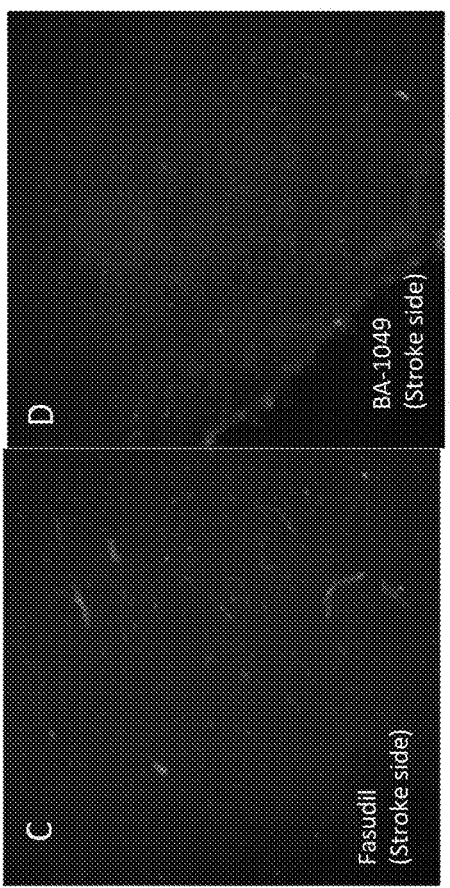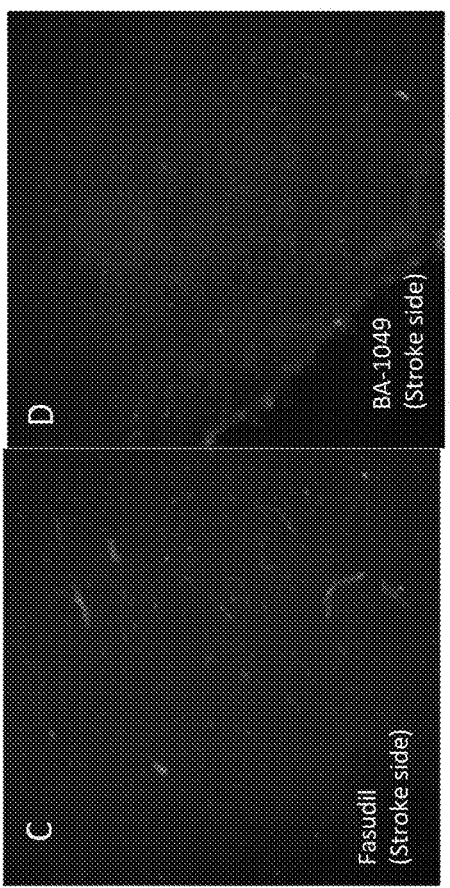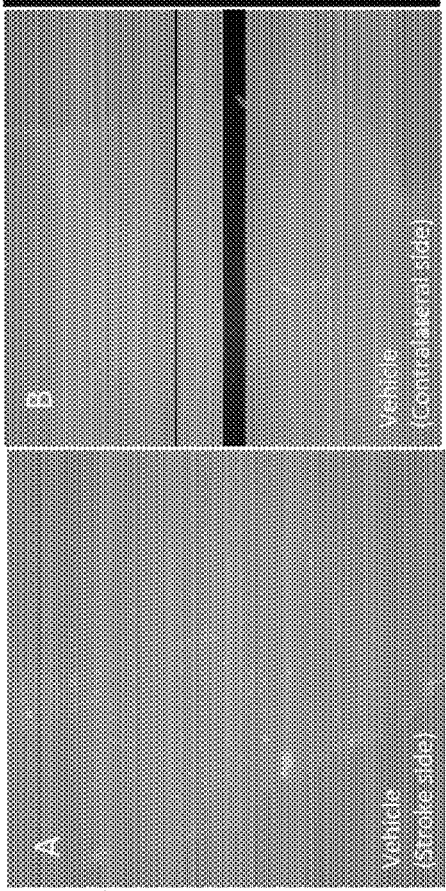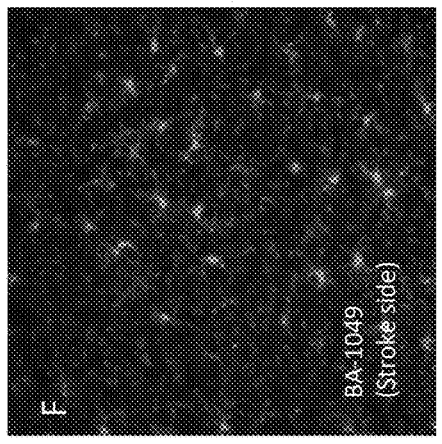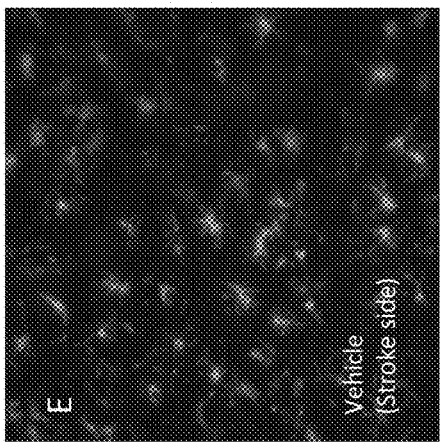

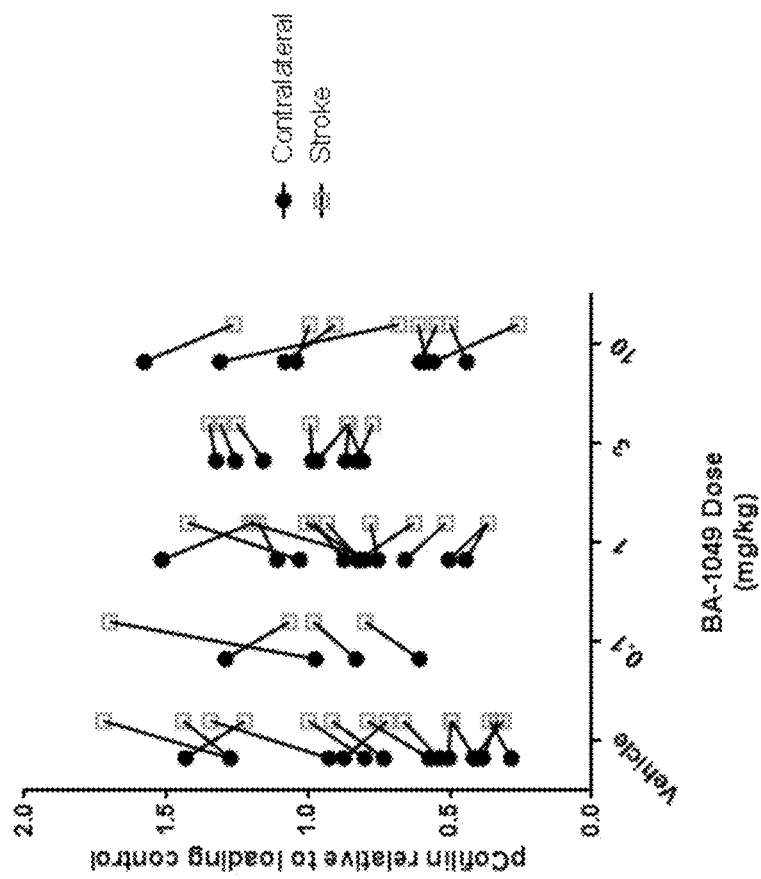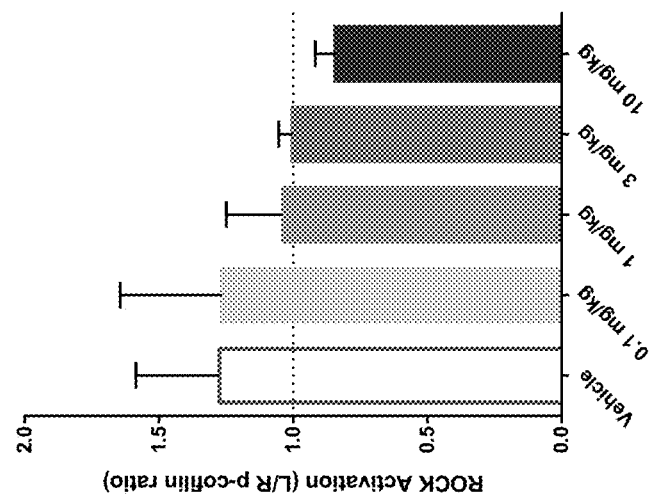

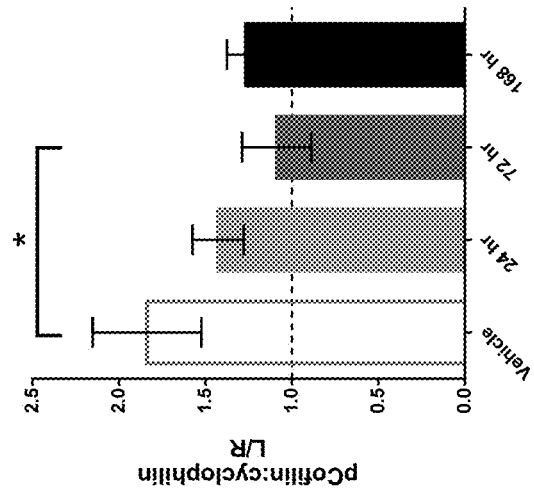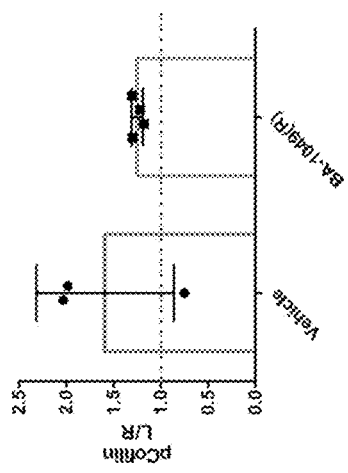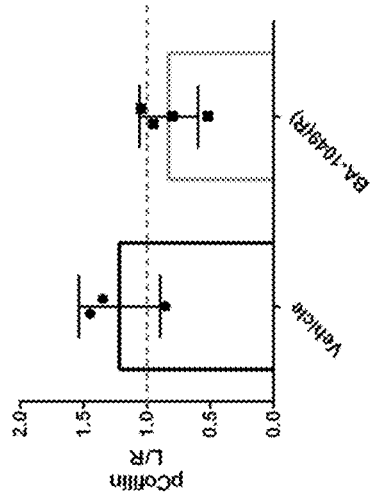

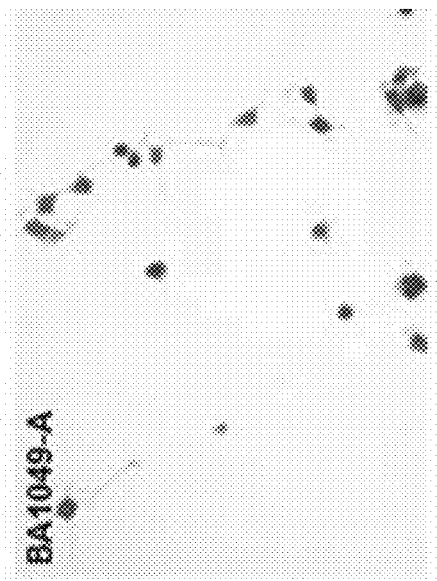
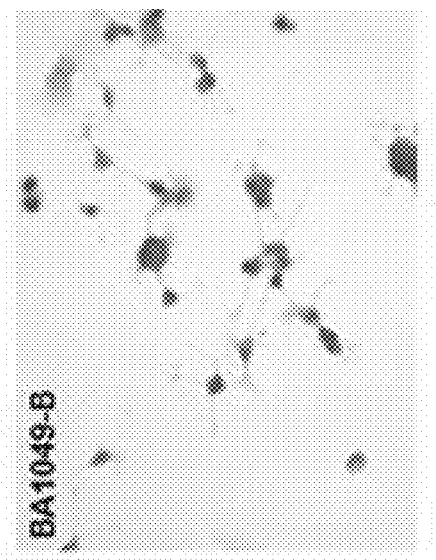
Fig. 15A  Fig. 15B  Fig. 15C  Fig. 15D

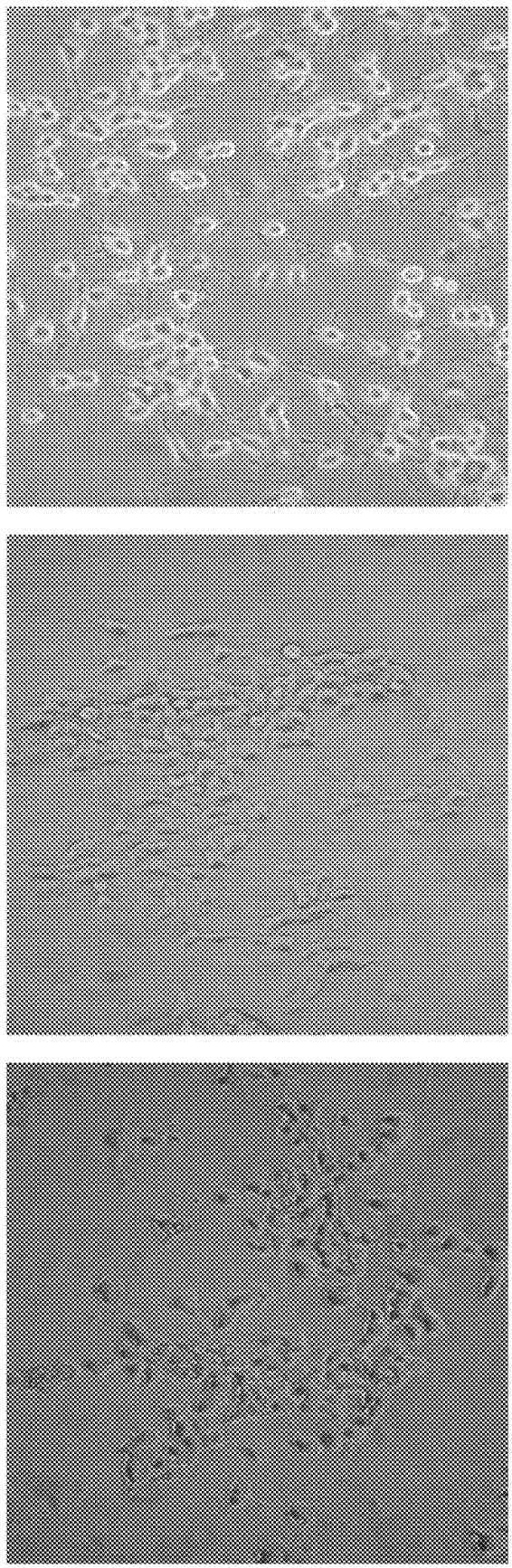

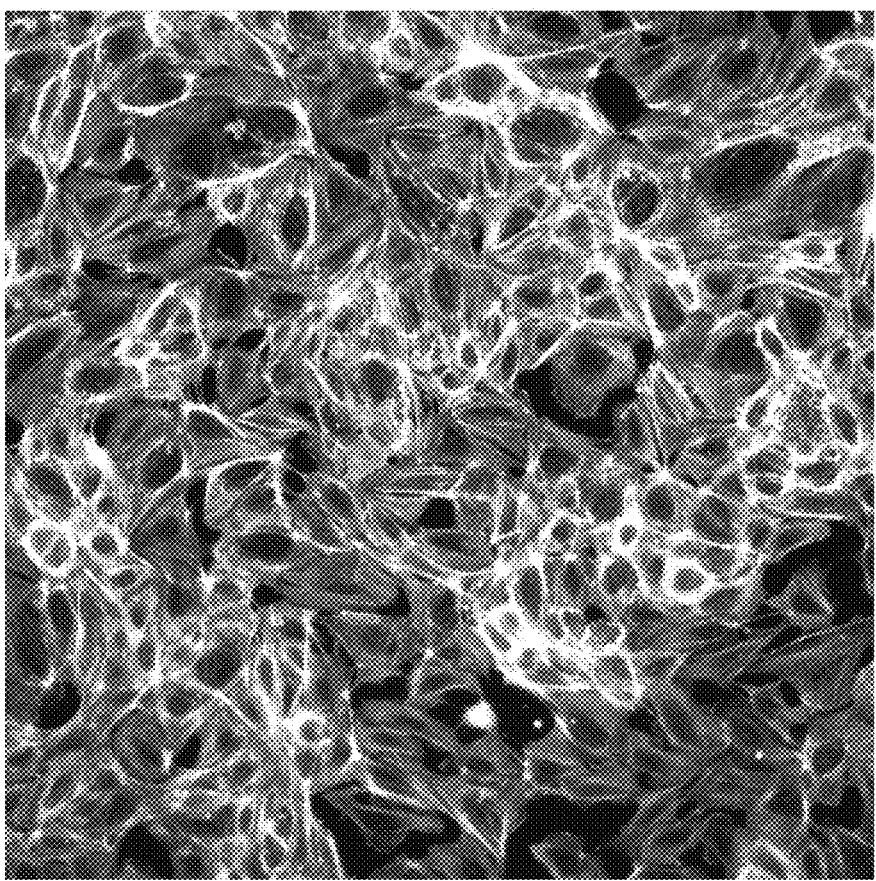
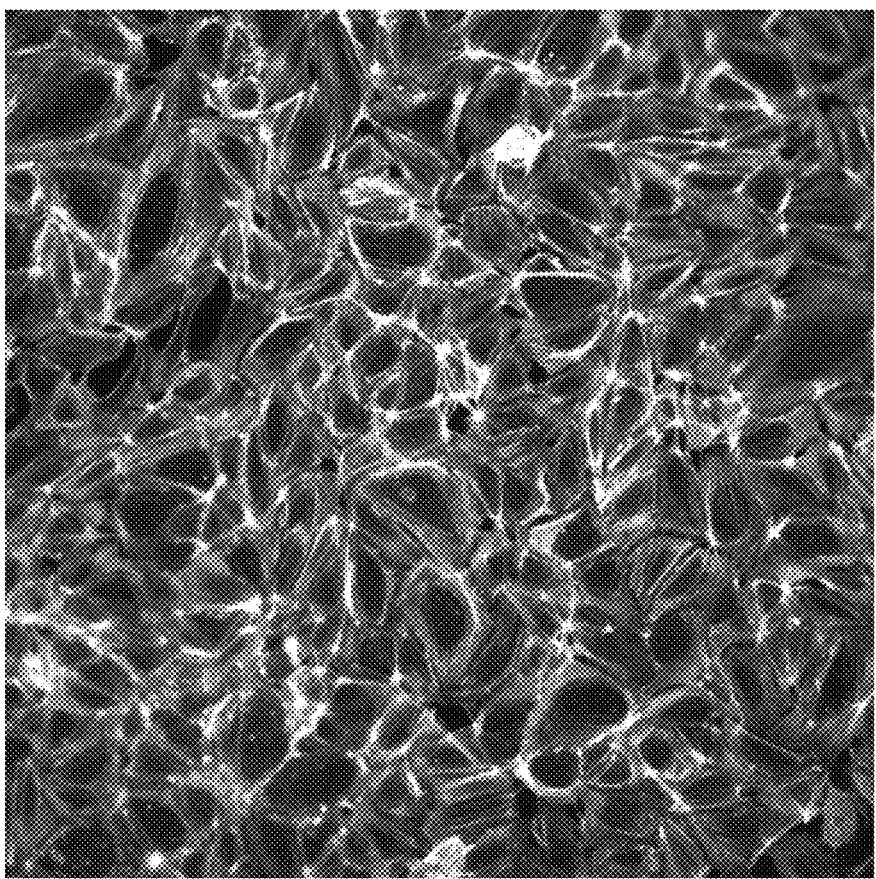

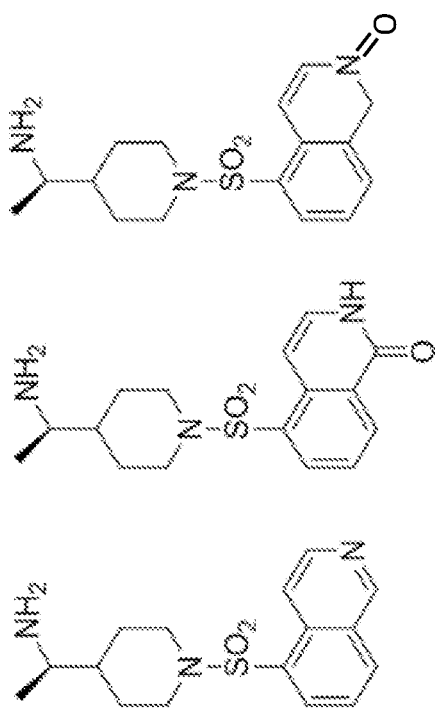

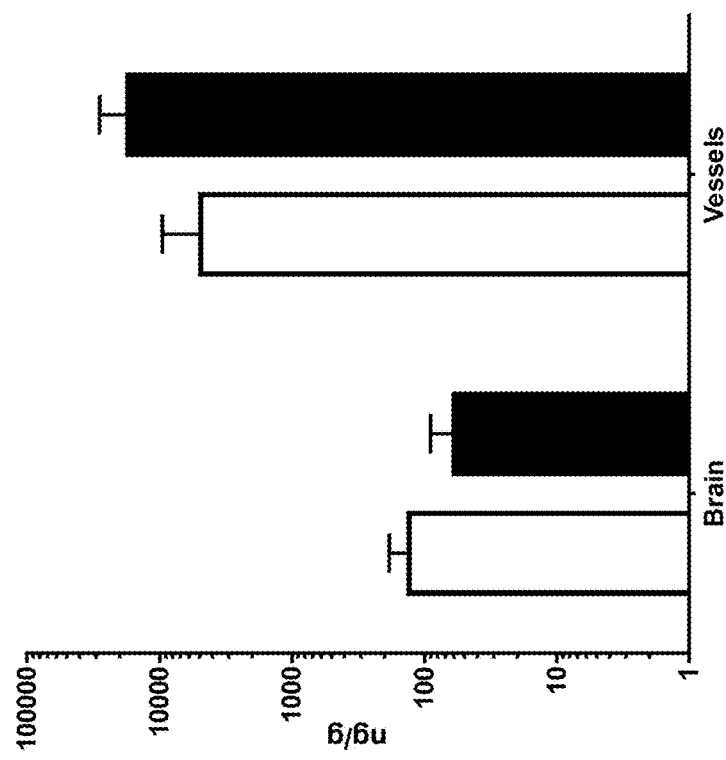
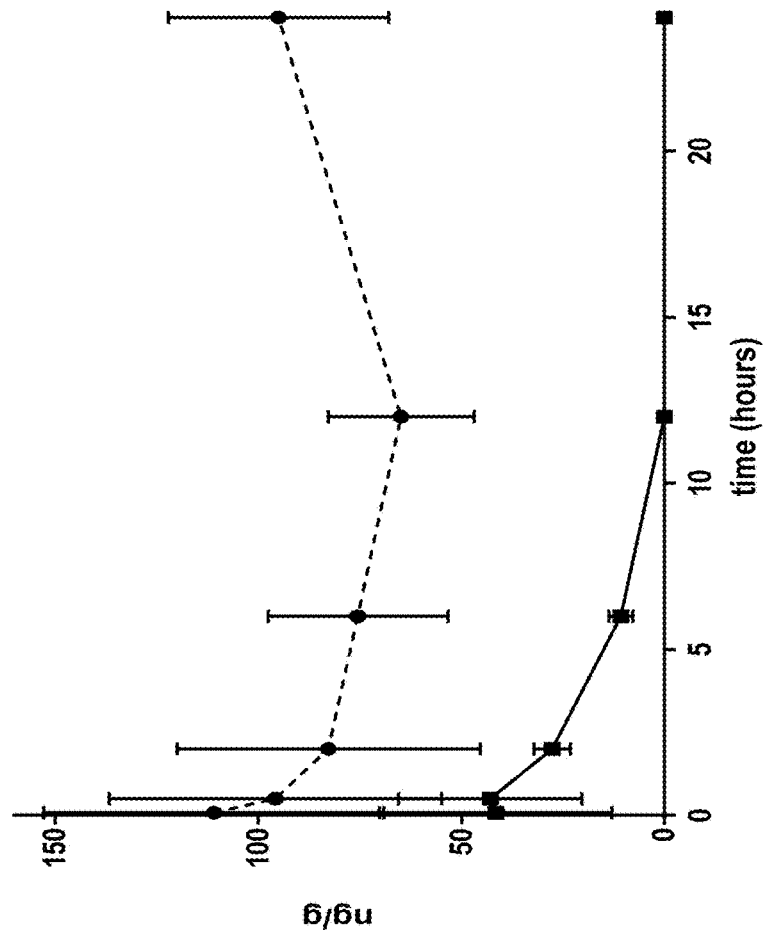
Fig. 22B
Fig. 22A

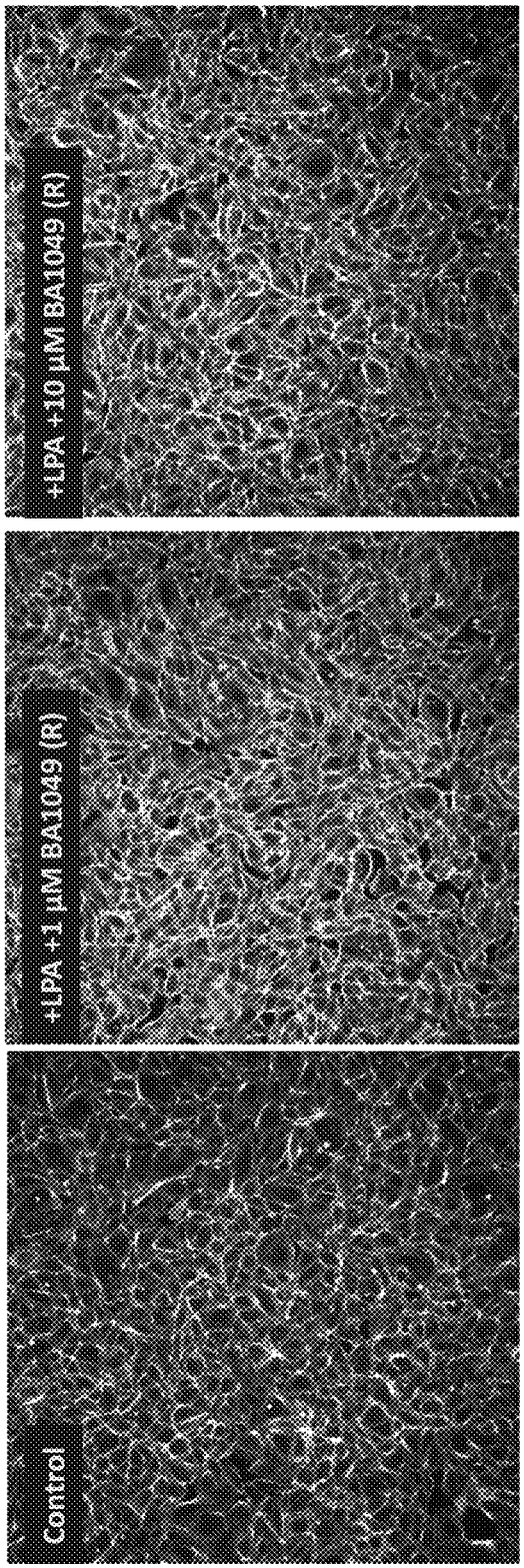

RHO KINASE INHIBITOR BA-1049 (R) AND ACTIVE METABOLITES THEREOF

CROSS-REFERENCE TO RELATED APPLICATIONS

This application is a division of U.S. application Ser. No. 15/988,736, filed May 24, 2018, which is a continuation of U.S. application Ser. No. 15/591,039, filed May 9, 2017, which claims the benefit of U.S. Provisional Application No. 62/437,181, filed Dec. 21, 2016. The entire teachings of the above application(s) are incorporated herein by reference.

FIELD OF THE INVENTION

The present disclosure relates to medicine and neurology. More particularly, it relates to specific ROCK2 inhibitor compounds useful for treating neurological conditions.

BACKGROUND OF THE INVENTION

Rho kinase (ROCK) is a serine/threonine kinase that plays a pivotal role in regulation of the cytoskeleton, motility, and junctional contacts in a variety of tissues. ROCK is activated when the small GTPase Rho is activated, and ROCK is downstream of Rho and plays a key role in phosphorylating other kinases in a complex intracellular signaling cascade. There are two isoforms of Rho kinase, ROCK1 and ROCK2, both of which are activated by Rho. ROCK1 has widespread tissue distribution (but less in brain and skeletal muscle). ROCK2 is expressed in the central nervous system (U.S. Pat. No. 7,572,013), brain, heart, and lung, but is relatively low in liver, spleen, kidney, and testes. These two different forms may have differences in biological activity and functions (Shi et al. (2013) *J. Cardiovasc. Pharmacol.* 62:341-354; Mertsch et al. (2014) Mol. Neurobiol. 49:900-915; Xin et al. (2015) *Biosci. Rep.* 35:1-13).

Both Rho and ROCK are abnormally activated in many types of neurotrauma and neurovascular diseases. Inhibitors of ROCK promote neurite outgrowth and axon regeneration after injury and inhibitors of ROCK are also effective in reducing ROCK activation in endothelial cells after stroke and in neurovascular diseases such as aneurysms or angiomas.

When a stroke, caused by a blood clot or thromboembolism, blocks blood flow through a blood vessel (ischemia), there is a decrease in the oxygenation of the tissue (hypoxia) including the cells of the blood vessel wall, itself. This injury to the cells of the blood vessel wall leads to an increase in the permeability of the wall, allowing plasma constituents to leak into the surrounding brain tissue. In many cases, overt bleeding into the brain can occur in the area of the blood clot due to functional problems with the blood vessel wall. ROCK signaling is a foundational element of this increased inappropriate vascular permeability (Shi et al. (2016) Nature Comm. 7:10523).

Subarachnoid hemorrhage is a condition requiring emergent treatment intervention and frequently is associated with poor patient outcomes. Either open or endovascular surgical approaches are commonly applied to either stop or minimize bleeding in order to limit damage. An important feature in managing patients with this disorder is to control the vasospasm and changes in vascular tone that often occurs as a co-morbidity. Calcium channel blockers such as nimodipine have been used clinically, as has the ROCK inhibitor Fasudil (Satoh et al. (2014) *Curr. Vasc. Pharmacol.*: 12(5): 758-765). While Fasudil has been used to control vasospasm in this setting, its non-selective effects on both ROCK1 and ROCK2, and likely its off-target effects on other kinases, have made its use limited to only the first two weeks after hemorrhage.

Similarly, when a traumatic brain injury (TBI) occurs, numerous forces (e.g. percussive or shear forces) can cause direct, primary injury not only to neurons and glia but also to the vasculature of the brain inducing hemorrhage. In the aftermath of a TBI, secondary injuries can also occur. Many of these injuries are the result of decreased blood perfusion in the area of the injury, as a consequence of vascular coagulation, and the onset of tissue edema due to increases in vascular permeability across the blood brain barrier (Chodobski et al. (2011) *Transl. Stroke Res.* 2(4):492-516).

In spinal cord injury, there is a disruption of the blood brain barrier. Further, broken axons do not regenerate spontaneously because of over-activation of Rho kinase. Inactivation of Rho kinase promotes functional repair after spinal cord injury (Watzalawick et al. (2013). *JAMA Neurol.* 71:91-99).

Cerebral cavernous malformations (CCMs) is another disorder that impacts the nervous system vasculature. CCMs are vascular malformations that develop essentially exclusively in the venous (low pressure) vascular bed within the nervous system. The dysfunction of any of the three proteins genetically linked to this disorder in the cells that form the blood vessel walls, causes reduced adhesion between the cells and hyperactivation of ROCK. Ultimately this leads to an increased leakiness in these blood vessel walls, allowing blood cells and other plasma constituents to enter the brain in a non-regulated manner (Clatterbuck et al. (2001) *J. Neurol. Neurosurg. Psychiat.* 71:188-192). The blood-brain barrier is typically a very strong and highly regulated structure and is formed between the cells of the small blood vessels (capillary vascular endothelial cells, pericytes) and other cells of the nervous system, including astrocytes. The function of the blood brain barrier is to highly regulate the entrance of blood-borne molecules into the brain, and the ability of cells present in the blood plasma to enter the brain (Ballabh et al. (2004) *Neurobiol. Dis.* 16:1-13). The unregulated release of plasma proteins and other molecules into the brain tissue commonly leads to functional problems in the brain, and red blood cell accumulation can cause pathologic iron deposition.

Small molecule kinase inhibitors typically compete with ATP for binding to the ATP pocket of the kinase. Because the structure of ATP pockets is conserved, kinase inhibitors may have non-specific binding to multiple kinases, causing unwanted off-target kinase inhibition. Some kinase cause toxicity because of on-target effects, in which case risk-benefit analysis will drive drug development decisions. Off-target effects can cause toxicity including cardiotoxicity, and these can be detected by kinome screening. Inactivation of AMP-activated protein kinase (AMPK) contributes to cardiotoxicity because it is a regulator of cellular metabolism and its activation is needed when cardiomyocytes are energy stressed (Chen et al. (2010) *Progr. Cardiovasc. Dis.* 53:114-120.) A number of kinase inhibitors are approved for human use despite increased risk of cardiotoxicity.

Most Rho kinase inhibitors target both ROCK1 and ROCK2 and thus are nonselective. For example, Fasudil, a non-selective ROCK inhibitor, inhibits both ROCK1 and ROCK2. Fasudil was developed for the short-term treatment of cerebral vasospasm following hemorrhagic stroke (Rikitake et al. (2005) *Stroke* 36(10):2251-2257). Fasudil has also been studied in spinal cord injury (Hara et al. (2000) *J. Neurosurg.* (Spine 1) 93:94-101). Unfortunately, Fasudil causes toxicity that includes nausea, subcutaneous hemorrhage, subarachnoid hemorrhage, pyrexia, kidney failure, and hypotension, and hence long term use of Fasudil causes severe complications (Fukumoto et al. (2005) *Heart* 91:391-392; Shi et al. (2013) *J. Cardiovasc. Pharmacol.* 62:341-354) (http://www.ehealthme.com/drug_side_effects/Fasudil-Hydrochloride-1268381).

Another example is SLx-2119 which is a ROCK2-specific Rho kinase inhibitor being clinically tested for efficacy in the treatment of psoriasis (https://clinicaltrials.gov/ct2/show/NCT02317627?term=kd025&rank=2). Unfortunately, SLx-2119 must be used at a higher dose to show efficacy in neuroprotection in a mouse model of stroke (Lee et al. (2014) *Ann. Clin. Transl. Neurol.* 1(1):2-14), and these effective doses tested were higher than the human tolerated dose, when converted to a human dose based on body surface area (FDA (2005) *Guidance for Industry* "Estimating the maximum safe dose in Initiating Clinical trials for Therapeutics in Healthy Volunteers"). These comparisons highlight the difficulty in developing therapeutic ROCK inhibitors that are both safe for systemic use and that can be used to treat neurological conditions.

Rho kinase inhibitors that have more selectivity for ROCK2 decrease the incidence of the associated side effect of hypotension (Xin et al. (2015) *Biosci. Rep.* 35:1-13). This is likely because ROCK1 is the predominant Rho kinase in smooth muscle (Pelosi et al. (2007) *Mol. Cell. Biol.* 27(17): 6163-6176), and it is the relaxing the tone of vascular smooth muscle that causes the side effect of hypotension, thereby preventing chronic systemic use of non-selective ROCK inhibitors such as Fasudil to treat neurological disorders.

FSD-C10 is an example of an inhibitor that targets ROCK2 more selectively than ROCK1 (Xin et al. (2015) *Biosci. Rep.* 35:1-13). This inhibitor causes less hypotension than Fasudil, indicating that reducing affinity of ROCK1 compared to ROCK2 is better for drug development. However, FSD-C10 does not have high affinity for ROCK2 and with an $IC_{50}$ of 1141 µM for ROCK1 and 711 µM for ROCK2 the compound does not have appropriate drug-like properties. When FSD-C10 was compared with Fasudil, it was not as effective as Fasudil in inducing neurotrophic factor expression in an experimental model of multiple sclerosis, and animals treated with FSD-C10 tended to lose weight, suggesting potential efficacy versus safety issues.

Therefore, what is needed are more therapeutics, high-affinity ROCK inhibitors with selectivity, but not complete specificity, for ROCK2.

SUMMARY OF THE INVENTION

It has been discovered that the (R) enantiomeric form of the Rho kinase inhibitor compound, BA-1049 (BA-1049 (R)), and hydroxyl metabolites thereof, target ROCK2 and have the ability to reverse ROCK activation in brain endothelial cells after neurovascular trauma. It has also been discovered that BA-1049 (R) promotes neurite outgrowth from neurons after a neurological trauma and has the potential to reverse ROCK activation in neurons after trauma in the CNS.

These discoveries have been exploited to develop the present disclosure, which, in part, is directed to BA-1049 (R), and active metabolites thereof, and to methods of preventing and treating CCMs, stroke, vasospasm after subarachnoid hemorrhage, cerebral aneurysms, spinal cord injury, and traumatic brain injury using the same.

In one aspect, the disclosure provides an R enantiomer of BA-1049, deuterated forms thereof, and adipate salts thereof.

In another aspect, the invention provides an active hydroxyl metabolite of BA-1049 (R), (1-hydroxy-BA-1049 (R)) and deuterated forms thereof, and adipate salts thereof.

The disclosure also provides methods of treating stroke, vasospasm after subarachnoid hemorrhage, cerebral aneurysms, spinal cord injury, or traumatic brain injury, in a patient suffering therefrom comprising administering to a patient a therapeutically effective amount of a pharmaceutical formulation comprising, BA-1049 (R), and/or an active hydroxyl metabolite thereof. In certain embodiments, the hydroxyl metabolite is 1-hydroxy-BA-1049 (R). In some embodiments, BA-1049 (R) and/or the hydroxyl metabolite of BA-1049 (R) are (is) deuterated and/or are (is) an adipate salt.

In another aspect, the disclosure provides pharmaceutical formulations comprising BA-1049 (R), activate hydroxyl metabolites thereof such as 1-hydroxy-BA-1049, or mixtures thereof. In some embodiments, BA-1049 (R) and/or the active metabolites thereof are deuterated. In other embodiments, BA-1049 (R) and/or the active metabolites thereof are adipate salts. In some embodiments, the pharmaceutical formulation further comprises a rho kinase inhibitor which is not BA-1049 (R) or 1-hydroxy-RA-1049 (R).

In certain embodiments, the hydroxyl metabolite is 1-hydroxy-BA-1049 (R).

Also provided are methods of treating CCM, in a patient suffering therefrom, comprising administering to the patient a therapeutically effective amount of a pharmaceutical formulation comprising 1-hydroxy-BA-1049 (R), and/or deuterated and/or adipate salts thereof. In yet other embodiments, the pharmaceutical formulation further comprises a second rho kinase inhibitor which is not 1-hydroxy-BA-1049 (R). In other embodiment, the method further comprises administering a second pharmaceutical formulation comprising a rho kinase inhibitor which is not 1-hydroxy-BA-1049 (R).

In certain embodiments, the hydroxyl metabolite is 1-hydroxy-BA-1049 (R).

In yet another aspect, the disclosure provides treating CCM, cerebral aneurysms, stroke, vasospasm after subarachnoid hemorrhage, or spinal cord injury in a patient suffering therefrom, comprising administering a pharmaceutical formulation comprising at least one rho kinase inhibitor that is not BA-1049 (R) or an active metabolite thereof. In certain embodiments, the pharmaceutical formulation comprises a second rho kinase inhibitor that is not BA-1049 (R) or 1-hydroxy-BA-1049 (R). In some embodiments, the method further comprises administering a second pharmaceutical formulation comprising a therapeutically effective amount of a rho kinase inhibitor that is not BA-1049 (R) or an active metabolite thereof.

DESCRIPTION OF THE DRAWINGS

The foregoing and other objects of the present disclosure, the various features thereof, as well as the disclosure itself may be more fully understood from the following description, when read together with the accompanying drawings in which:

FIG. 6A is a graphic representation of a plot of binding dissociation curve against ROCK1 for BA-1049 (S);

FIG. 6B is a graphic representation of a plot of binding dissociation curve against ROCK1 for BA-1049 (R);

FIG. 6C is a graphic representation of a plot of binding dissociation curve against ROCK2 for BA-1049 (S);

FIG. 6D is a graphic representation of a plot of binding dissociation curve against ROCK2 for BA-1049 (R);

FIG. 7A is a graphic representation of inhibition curve plot for $IC_{50}$ analysis of BA-1049 (S) against ROCK1;

FIG. 7B is a graphic representation of inhibition curve plot for $IC_{50}$ analysis of BA-1049 (S) against ROCK2;

FIG. 7C is a graphic representation of inhibition curve plot for $IC_{50}$ analysis of BA-1049 (R) against ROCK1;

FIG. 7D is a graphic representation of inhibition curve plot for $IC_{50}$ analysis of BA-1049 (R) against ROCK2;

FIGS. 10A-10D are representations of photomicrographs of the insular cortex of the stroke side of a stroke brain treated with BA-1049 (FIG. 10D), Fasudil (FIG. 10C), or vehicle only (FIG. 10A) and (FIG. 10B); stroke side of brain (FIG. 10A) compared to the contralateral side (FIG. 10B) not affected by stroke in animals injected with vehicle only, where brain sections were subjected to immune-histochemistry using antibodies against phospho-MLC2.

FIGS. 10E-10F are representations of photomicrographs of activated microglia detected by immunostaining with Iba-1 antibody, where microglia are activated on the stroke side (FIG. 10E) and activation is reversed by BA-1049 (FIG. 10F);

FIG. 11A is a graphic representation of a dose-response experiment using different concentrations of BA-1049 (R) administered by intraperitoneal injection in adult mice, where the analysis of phospho-cofilin in left versus right brain as a biomarker of ROCK activation shows that the minimum effective dose to reverse ROCK activation to normal (value of 1) is 1 mg/kg (FIG. 11A).

FIG. 11B is a graphic representation showing phospho-cofilin levels in right (contralateral) versus left (stroke) for individual animals where the right and left brain values for a given animal are connected by a line;

FIG. 12A is a graphic representation of the reduction in phospho-cofilin in mouse brain 4 hours after treatment with BA-1049 (R) or vehicle (control) immediately after middle cerebral artery occlusion and the onset of reperfusion;

FIG. 12B is a graphic representation of the reduction in phospho-cofilin in mouse brain 24 hours after treatment with BA-1049 (R) or vehicle (control) immediately after transient middle cerebral artery occlusion and the onset of reperfusion;

FIG. 12C is a graphic representation of pretreatment of mice with 10 mg/kg BA-1049 (R) given I.P. 24 hours, 72 hours, and 168 hours prior to middle cerebral artery occlusion;

FIGS. 15A-15D are representations of photomicrographs of neuronal NG-108 cells plated in cell culture and treated with DMSO as control (FIG. 15A), racemic BA-1049 (FIG. 15B), BA-1049 (S) (FIG. 15C), and BA-1049 (R) (FIG. 15D);

FIGS. 16A-16C are representations of photomicrographs of NG-108 cells treated with 5 µM SLx-2119 (FIG. 16A), 5 µM BA-1049 (R) (FIG. 16B), or 50 µM BA-1049 (R) (FIG. 16C);

FIGS. 18A-18B are representations of photomicrographs showing the effect of lysophosphatidic acid (LPA), (a compound known to induce activation of ROCK), on endothelial cells (FIG. 18B); compared to control, untreated cells (FIG. 18A);

FIG. 21A is a schematic representation of the structure of BA-1049 (R);

FIG. 21B is a schematic representation of the structure of 1-hydroxy-BA-1049 (R);

FIG. 21C is a schematic representation of the structure of N-oxide-BA-1049 (R);

FIG. 22A is a graphic representation of the time course of the concentration of BA-1049 (R) (dashed lines) and 1-hydroxy-BA-1049 (R) (solid line) in the brain after intravenous administration of 5 mg/kg BA-1049 (R) to mice;

FIG. 22B is a graphic representation of the concentration of BA-1049 (R) (open bars) and 1-hydroxy-BA-1049 (R) (filled bars) in brain and vascular tissue (derived from inferior vena cava) of rats, 30 minutes after the intravenous administration of 2.5 mg/kg BA-1049 (R);

FIGS. 25A-25F are representations of photomicrographs of human umbilical vein endothelial cells treated with LPA to induce ROCK activation, followed by treatment with 1 µM BA-1049 (R) (FIG. 25B), 10 µM BA-1049 (R) (FIG. 25C), 1 µM BA-1049 (S) (FIG. 25E), or 10 µM BA-1049 (S) (FIG. 25F), where FIG. 25A shows untreated (control) cell where FIG. 25D shows cells treated only with LPA.

DESCRIPTION

The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Unless defined otherwise, all technical and scientific terms used herein have the same meaning as commonly understood by one of ordinary skill in the art to which this disclosure belongs. The initial definition provided for a group or term herein applies to that group or term throughout the present specification individually or as part of another group, unless otherwise indicated.

The present disclosure provides the R enantiomer of the BA-1049 (BA-1049 R), active metabolites thereof, such as 1-hydroxy-BA1049(R), deuterated forms of BA-1049 (R) and/or its active metabolites, and adipate salts of BA-1049 (R) and/or its active metabolites. The present disclosure also provides methods of treating various CNS disorders and injuries using these compounds in pharmaceutical formulations.

BA-1049 (R) Synthesis

Figure 1B:
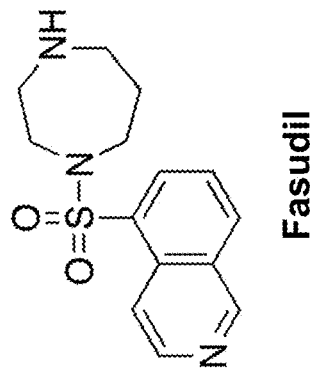
FIG. 1B is a schematic representation of Fasudil.
Figure 1D:
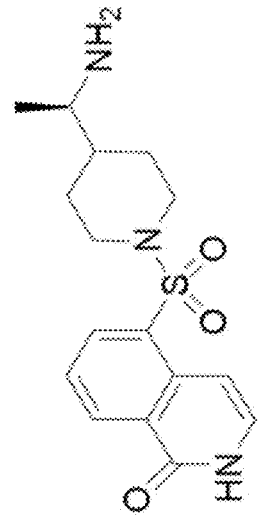
FIG. 1D is a schematic representation of 1-hydroxy-BA-1049 (R).
Figure 1A:
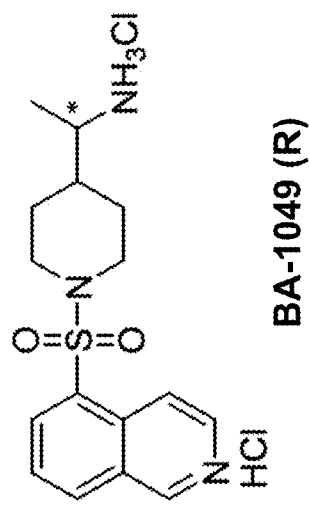
FIG. 1A is a schematic representation of BA-1049, a selective piperidinyl compound, where the asterisk identifies the chiral carbon.
Figure 1C:
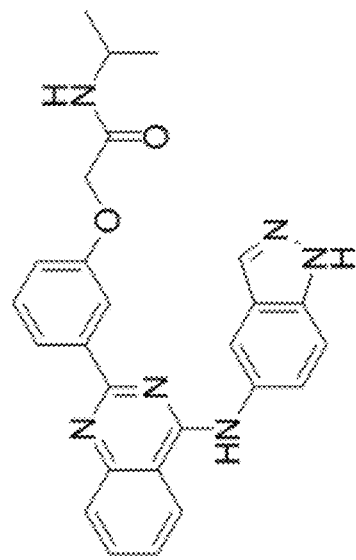
FIG. 1C is a schematic representation of SLx-2119 (also referred to as KD-025)
Figure 2:
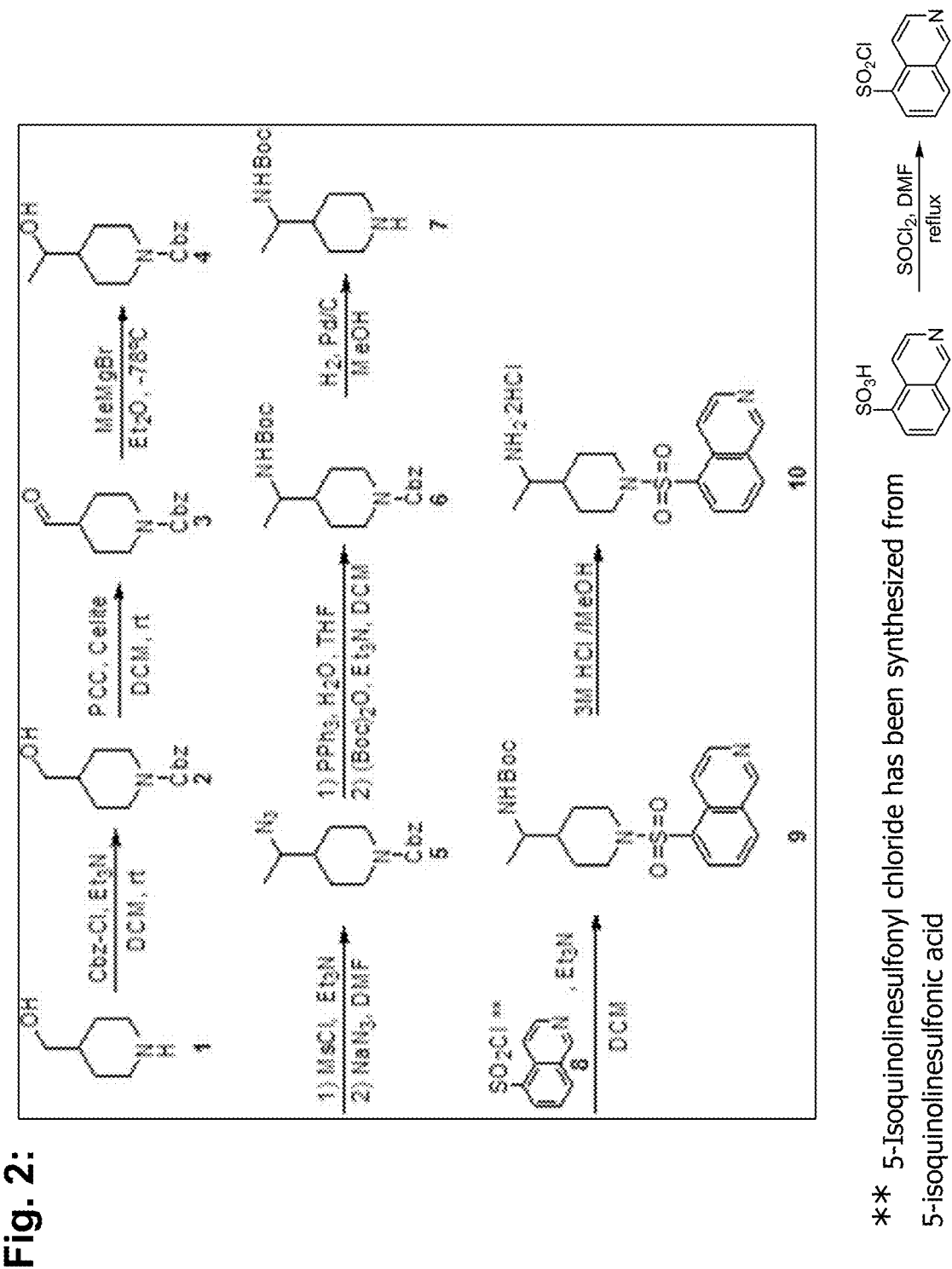
FIG. 2 is a schematic representation of the racemic synthesis of BA-1049, where the R enantiomer can be purified from the racemic mix by column chromatography.

BA-1049 (FIG. 1A), a 4-substituted piperidine derivative existing as a racemic mixture can be made in any method known in thereof, and has been described and its mode of preparation set forth in U.S. Pat. Nos. 7,572,913 and 8,957,093 (FIG. 2).

Figure 3:
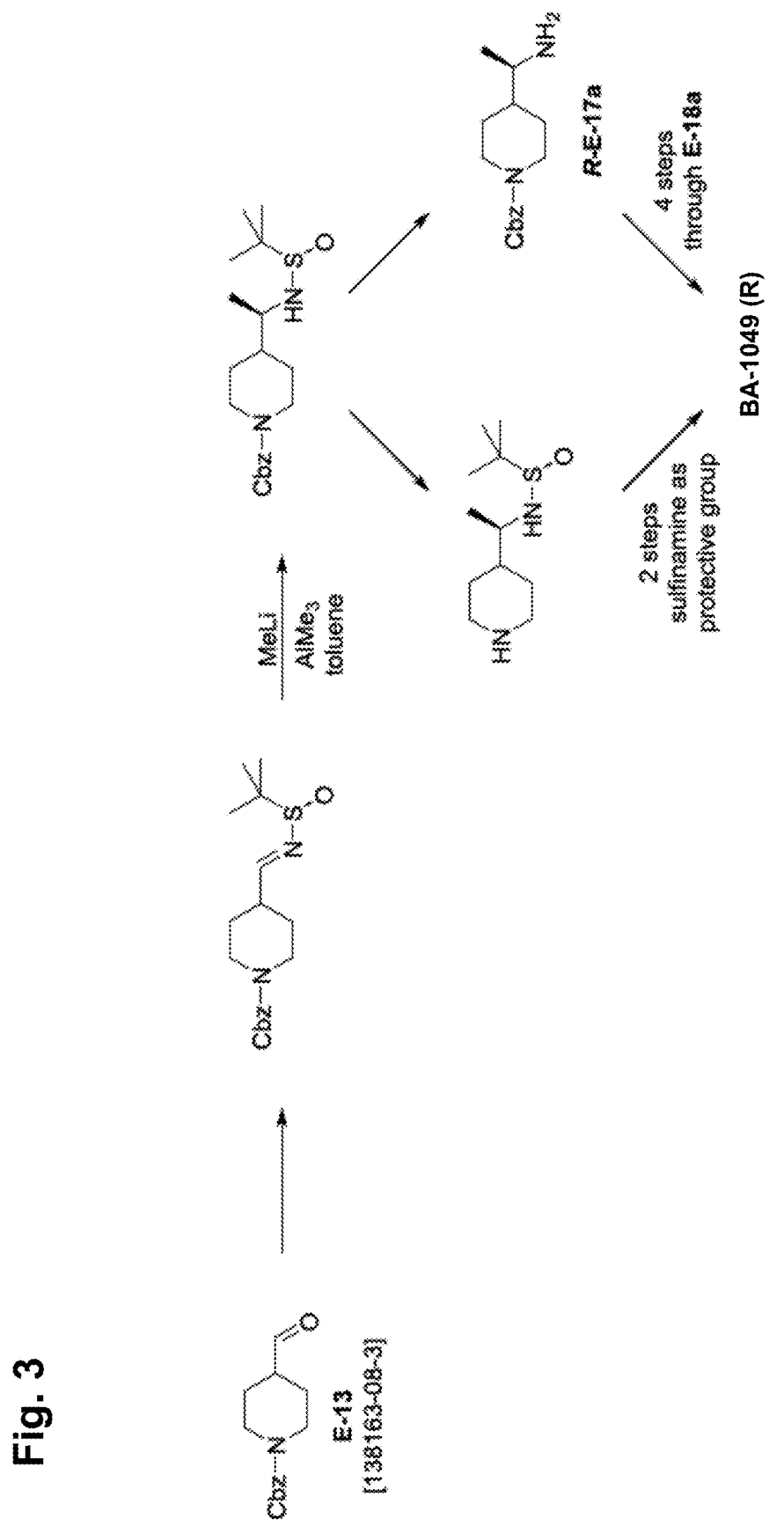
FIG. 3 is a representation of a synthetic scheme for preparing optically pure BA-1049 (R) utilizing diastereoselective introduction of a methyl group with a Lewis acid added for improved selectivity.

BA-1049 (R) (FIG. 22A) can be prepared after purification from the racemic mixture of (R) and (S) enantiomers, e.g., by column chromatography. Alternatively, BA-1049 (R) can be synthesized de novo as a chirally pure compound as shown in FIG. 3 or by any method known in the art.

Figure 4:
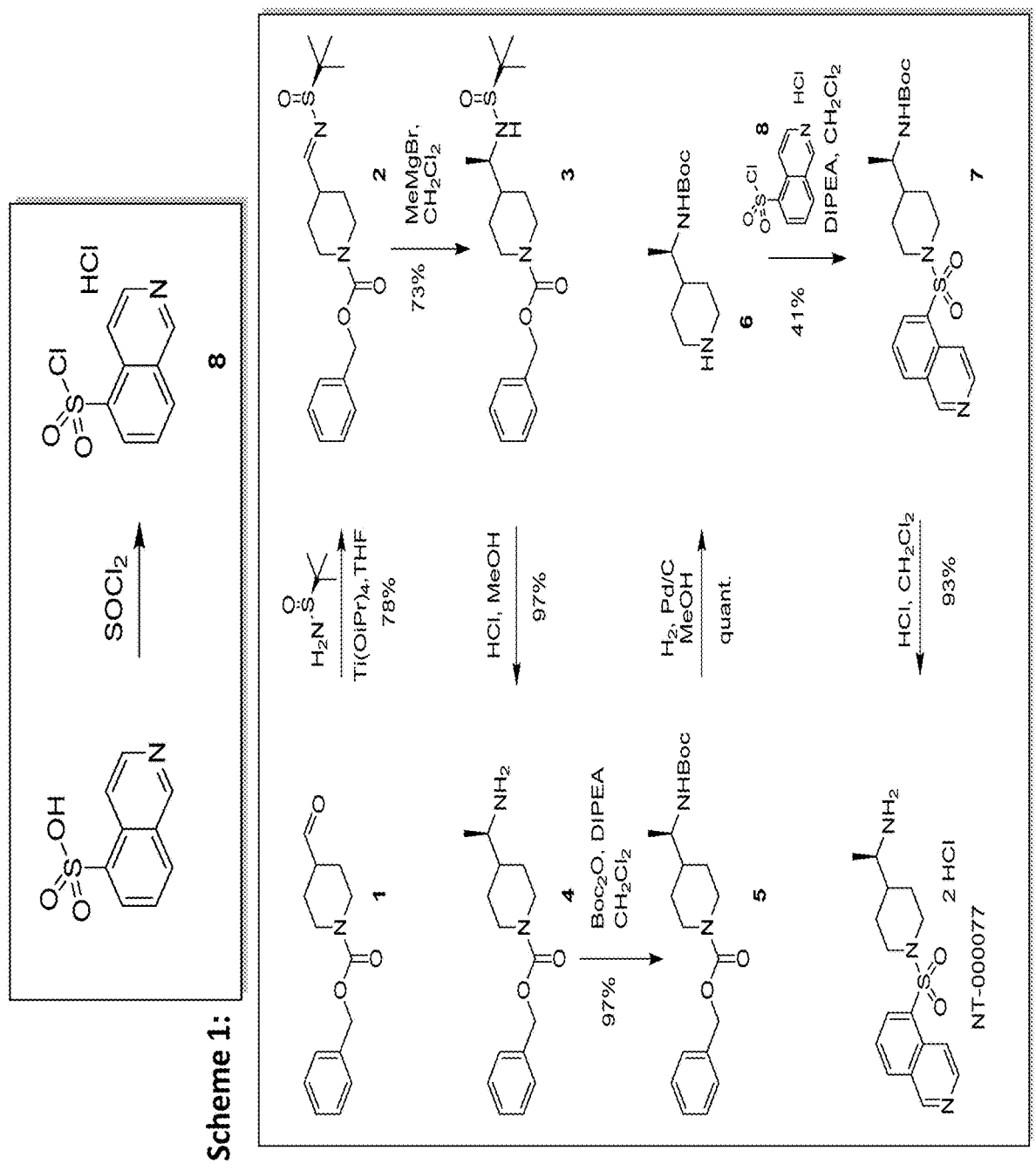
FIG. 4 is a schematic representation of an alternative synthetic scheme for preparing BA-1049 (R) ("NT-000077")

Alternatively, stereocontrolled synthesis of BA-1049 can be performed, as shown in FIG. 4, and as described in EXAMPLE 1. Briefly, in this method, condensation of the commercially available 1-benzyloxycarbonyl-4-formylpiperidine (1) with (S)-(−)-2-methyl-2-propanesulfinamide under standard conditions, stir for 18 hours at room temperature, filter through celite, separation of the organic layer, concentration and purification by column chromatography, affords the required chiral imine 2. The latter was then transformed to the (R, S) diastereomer 3 by selective addition of methyl Grignard at low temperature. Removal of the chiral auxiliary, protecting group manipulations, and the introduction of the isoquinoline 8 results in the same intermediate 7 used in the racemic synthesis of BA-1049 (R) (see FIG. 2).

Synthesis of 1-Hydroxy-BA-1049(R)

The 1-hydroxy-BA-1049 (R) metabolite was isolated from cultures of hepatocytes after they were exposed to BA-1049 (R) and characterized using LC-MS methods as described in EXAMPLE 2.

Figure 5:
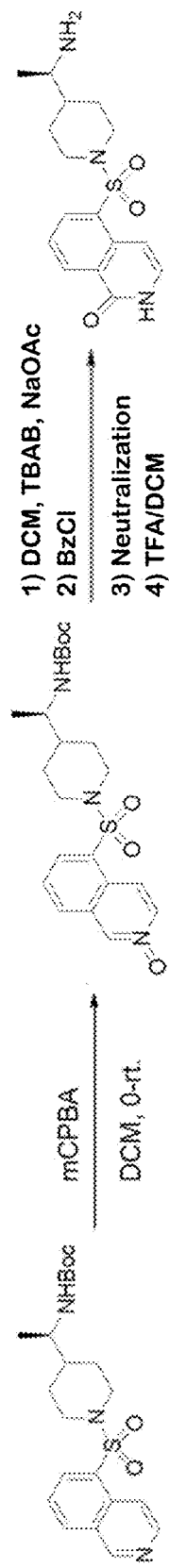
FIG. 5 is a schematic representation of a synthetic scheme for preparing optically pure 1-hydroxy-BA-1049 (R) beginning with the Boc-protected penultimate compound from the synthesis of enantiopure BA-1049 (R)

FIG. 5 shows one non-limiting method of chemically synthesizing 1-hydroxy-BA-1049 (R) starting with compound 9 illustrated in FIG. 2.

Specificity of BA-1049 (R) Binding

To determine the specificity/selectivity of BA-1049 (R) for ROCK1 and ROCK2, the disassociation constant ($K_D$) values for racemic BA-1049 and its individual enantiomers were determined as follows:

BA-1049 was synthesized, and the racemic mixture was separated into its enantiomers on a chiral column. Six additional Rho kinase inhibitors having structural similarity to BA-1049 (i.e., BA-1041, BA-1042, BA-1043, BA-1050, BA-1050A, and BA-1050B) were also synthesized. The $K_D$'s of these compounds were then measured to determine their selectivity for ROCK2 (see EXAMPLE 2, Table 5).

FIG. 6A-FIG. 6D and Table 1 illustrate the $K_D$'s for binding to either ROCK1 (FIG. 6A and FIG. 6B) or ROCK2 (FIG. 6C and FIG. 6D) by BA-1049 (R) and (S) isomers. Table 1 also shows the $K_D$'s for binding to ROCK1 or ROCK2 by Fasudil and SLx-2119 and the ratio of the dissociation constants of these compounds for each kinase (i.e., selectivity for ROCK2 binding).

TABLE 1

| Inhibitor | ROCK1 $K_d$ (nM) | ROCK2 $K_d$ (nM) | Fractional Selectivity for ROCK2 |
|---|---|---|---|
| BA-1049 (R) | 110 | 59 | 1.86 |
| BA-1049 (S) | 120 | 130 | 0.92 |
| Fasudil | 50 | 45 | 1.11 |
| SLx-2119 | 7400 | 65 | 113.85 |

These results reveal that BA-1049 (R) bound the most strongly to ROCK2. In contrast, the (S) enantiomer of BA-1049 bound to ROCK1 and ROCK2 with similar affinities.

D. $IC_{50}$ Determination of BA-1049

The potency ($IC_{50}$ values), or the ability of the enantiomers of BA-1049 to inhibit either ROCK1 or ROCK2, was then determined. Two similar competitive binding assays were used which measured the ability of each compound to compete with an immobilized enzyme active-site-directed ligand to perform determinations for ROCK1 and ROCK2 using a standard ATP concentration of 10 μM.

The results shown in FIGS. 7A-7D and Table 2 were obtained using a direct filter-binding radiometric kinase assay (see EXAMPLE 2). The $IC_{50}$'s against ROCK1 and ROCK2 for BA-1049 (S) (FIG. 7A and FIG. 7B) and BA-1049 (R) (FIG. 7C and FIG. 7D) were determined using 10 μM ATP for both enzyme reactions.

TABLE 2

| | Compound $IC_{50}$ (μM): | | Fold- |
|---|---|---|---|
| Compound | ROCK1 | ROCK2 | Difference |
| BA-1049 (S) | 10.2 | 0.73 | 14.1 |
| BA-1049 (R) | 3.9 | 0.24 | 16.2 |

The results show that BA-1049 (R) and (S) are ROCK2-selective and that BA-1049 (R) has the best ROCK2 $IC_{50}$ (0.24 μM).

Obtained by the protocol described in EXAMPLE 2, the results in Table 3 show the $IC_{50}$ against ROCK1 and ROCK2 for BA-1049 (S) and BA-1049 (R) with reactions performed at the Km concentration for ATP specific to each given isoform of ROCK (ROCK1 at 70 μM and ROCK2 at 15 μM ATP).

TABLE 3

| | Compound $IC_{50}$ (μM): | | Fold- |
|---|---|---|---|
| Compound | ROCK1 70 μM ATP | ROCK2 15 μM ATP | Difference |
| BA-1049 (S) | 57.9 | 1 | 57.9 |
| BA-1049 (R) | 29.6 | 0.34 | 86.2 |

These results show that BA-1049 (R) has an 86-fold greater selectivity for ROCK2 than for ROCK1. The variability in ROCK selectivity using different ATP concentrations may be due to the fact that at 10 μM ATP, ROCK1 is below its Km and therefore would take longer to reach $V_{max}$, requiring less BA-1049 to compete with and inhibit enzyme activity. Thus, BA-1049 (R) has high potency for ROCK2 in ischemic or diseased tissue where ATP concentrations are reduced compared to healthy tissue.

Therapeutic Uses of BA-1049 (R) and 1-Hydroxy-BA-1049 (R)

BA-1049 (R) and 1-hydroxy-BA-1049 (R) are selective for ROCK2, the isoform of ROCK highly expressed in the central nervous system. ROCK2 is hyperactivated in neurons in various neurological diseases in part because of the inflammatory component of the disease and entry of molecules such as tumor necrosis factor and LPA that are known to act as activators of ROCK. Such diseases include amyotrophic lateral sclerosis (ALS), Alzheimer's Disease, Parkinson's Disease, multiple sclerosis, Huntington's Disease, and spinal muscular atrophy (SMA). Because the release of myelin-derived growth inhibitory proteins in neurotrauma causes hyperactivation of ROCK2, BA-1049 (R) and 1-hydroxy-BA-1049 (R) are useful in treating spinal cord injury, traumatic brain injury, optic nerve injury and peripheral nerve injuries.

Because ischemia causes ROCK hyperactivation in brain endothelial cells, BA-1049 (R) is useful to treat stroke, vasospasm after subarachnoid hemorrhage, cerebral cavernous malformation, hereditary hemorrhagic telangiectasis, cerebral arteriovascular malformations, and Behcet's Disease.

BA-1049 (R) and 1-hydroxy-BA-1049 (R) are useful to treat autism and diseases such as Fragile X, Rett's Syndrome, and other disorders where there are abnormalities in dendritic spines. This is because ROCK is a critical regulator of the cytoskeleton and of dendritic spine formation, and overactivation of ROCK leading to abnormal dendritic spines has been reported in various forms of autism.

In addition, because ROCK2 is the predominant form of ROCK expressed in epithelial cells of the large colon, BA-1049 is useful in treating diseases where ROCK2 is hyperactivated in diseased epithelial cells. As with endothelial cells, ROCK2 regulates cell-cell junctions between epithelial cells. Therefore BA-1049 (R) and 1-hydroxy-BA-1049 (R) are useful in treating Crohns' disease and inflammatory bowel disease.

Because ROCK is activated in epithelial cells upon irradiation, BA-1049 (R) is useful in protecting cells from the harmful effects of ionizing radiation used in chemotherapy, or radiation resulting from environmental hazards. This is useful for the gastrointestinal effects of radiation syndrome.

In various epithelial cells ROCK also plays a role in regulating the expression of collagen. BA-1049 (R) is effective in treating various fibrotic diseases e.g., in the kidney and liver, and especially fibrosis of the lung, because ROCK2 is highly expressed in lung.

The active metabolite 1-hydroxy-BA-1049 (R) shows efficacy against ROCK2 and thus has utility in many of the same roles as for BA-1049 (R) as described above. Aldehyde oxidase is an enzyme well-known for its importance in the metabolism of xenobiotics, especially those that are N-heterocycles such as BA-1049 (R), and is the enzyme likely involved in the generation of 1-hydroxy-BA-1049 (R) when BA-1049 (R) is administered orally. As such, 1-hydroxy-BA-1049 (R) is preferentially used via the intravenous route when a patient in an acute setting shows altered or reduced levels of consciousness, and thus oral administration of a drug is difficult or impossible. In some settings, either genetics or pathology may guide the choice of compound.

Because there are naturally occurring polymorphisms in the aldehyde oxidase gene in humans that can lead to reduced activity of this enzyme (Hartmann et al. (2012) *Drug Metab. Disposition;* 40(5): 856-864), this population benefits from administration of 1-hydroxy-BA-1049 (R) for the diseases, disorders or injuries as described above. Additionally, identification of chronic alcohol use or abuse in a social history favors the choice of 1-hydroxy-BA-1049 (R) for use in treating diseases, disorders or injuries such as the ones listed above, as a history of alcohol abuse can cause significant reductions in aldehyde oxidase activity in the hepatocytes of the liver (Hutzler et al. (2014) *Drug Metab. Disposition;* 42(6): 1090-1097). Accordingly, for treatment of acute spinal cord injury and traumatic brain injury the hydroxy metabolite is useful because intoxication is a common co-morbidity with neurotrauma in civilian populations.

Therapeutic Pharmaceutical Formulations

The pharmaceutical formulations useful in the therapeutic methods according to the disclosure include a therapeutically effective amount of BA-1049 (R) and/or active metabolites thereof, such as 1-hydroxy-BA-1049 (R), and/or adipate salts thereof and/or deuterated form thereof. Other pharmaceutical formulations for use in treating CCM, aneurysm, and those disorders listed above include therapeutically effective amounts of rho kinase inhibitors other than BA-1049 (R) or 1-hydroxy-BA-1049 (R).

A "therapeutically effective amount" as used herein refers to that amount which provides a therapeutic and/or prophylactic therapeutic effect for treating a neurological trauma such as a CCM, cerebral aneurysm, stroke, vasospasm after subarachnoid hemorrhage, or spinal cord injury. If another Rho inhibitor compound is part of the BA-1049 (R) pharmaceutical formulation, or if it is to be administered in a separate pharmaceutical formulation, the therapeutically effective amount may be different for each one, and the addition of one or more of these drugs in the formulation can alter the ratio of the kinase inhibited.

Such formulations are prepared with a pharmaceutically acceptable carrier in accordance with known techniques, for example, those described in Remington, *The Science And Practice of Pharmacy* (9th Ed. 1995). The term "pharmaceutically acceptable carrier" is to be understood herein as referring to any substance that may, medically, be acceptably administered to a patient, together with a compound of this invention, and which does not undesirably affect the pharmacological activity thereof; a "pharmaceutically acceptable carrier" may thus be, for example, a pharmaceutically acceptable member(s) selected from the group comprising or consisting of diluents, preservatives, solubilizers, emulsifiers, adjuvant, tonicity modifying agents, buffers as well as any other physiologically acceptable vehicle. This pharmaceutical formulation may further contain additional Rho inhibitors.

The pharmaceutical formulation may be prepared for injectable use, for oral use, for inhalation use, for transdermal use, for transmembrane use, and the like.

Formulations suitable for oral administration may be presented in discrete units or dosage forms, such as capsules, cachets, lozenges, tablets, sublingual tablets, pills, powders, granules, chewing gum, suspensions, solutions, and the like. Each dosage form contains a predetermined amount of Rho kinase inhibitor compound. If in the form of a solution, the pharmaceutically acceptable carrier may be an aqueous liquid, such as buffered with a pharmaceutically acceptable pH buffer, or in non-aqueous liquid such as DMSO, or be prepared as an oil-in-water or water-in-oil emulsion.

Injectable dosage forms may be sterilized in a pharmaceutically acceptable fashion, for example by steam sterilization of an aqueous solution sealed in a vial under an inert gas atmosphere at 120° C. for about 15 minutes to 20 minutes, or by sterile filtration of a solution through a 0.2 µM or smaller pore-size filter, optionally followed by a lyophilization step, or by irradiation of a composition containing a compound of the present invention by means of emissions from a radionuclide source.

A therapeutically effective dosage of BA-1049 (R) or an active hydroxyl metabolite thereof may vary from patient to patient, and may depend upon factors such as the age of the patient, the patient's genetics, and the diagnosed condition of the patient, and the route of delivery of the dosage form to the patient. A therapeutically effective dose and frequency of administration of a dosage form may be determined in accordance with routine pharmacological procedures known to those skilled in the art. For example, dosage amounts and frequency of administration may vary or change as a function of time and severity of the neurological trauma. A dosage from about 0.1 mg/kg to 1000 mg/kg, or from about 1 mg/kg to about 100 mg/kg BA-1049 (R), 1-hydroxy-BA-1049 (R), or deuterated or adipate salts thereof, may be suitable.

Administration may be by injection into cerebrospinal fluid as a solution or as a suspension suitable for sustained release from the injected pharmaceutical dosage form such as from a vesicle. Administration alternatively may be made to the lesion site by stereotactic injection.

Reference will now be made to specific examples illustrating the disclosure. It is to be understood that the examples are provided to illustrate exemplary embodiments and that no limitation to the scope of the disclosure is intended thereby.

EXAMPLES

Example 1

Synthesis of BA-1049 (R)

The following scheme describes the synthesis of 50 mg to 100 mg of enantiomer R of BA-1049 (NT-000077) and includes a chiral synthesis method that enables the identification of the absolute configuration ((R) or (S)) of the molecule.

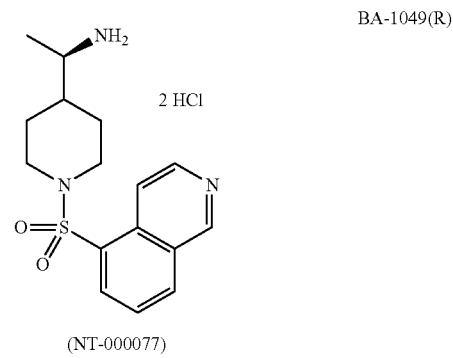 [SMILES: C[C@@H](N)C1CCN(S(=O)(=O)c2cccc3cnccc23)CC1]

To a solution of 1-benzyloxycarbonyl-4-formylpiperidine (1) (2.0 g, 8.1 mM) in THF (20 mL) was added (S)-2-methylpropane-2-sulfinamide (1.0 g, 8.5 mM) followed by Ti(OiPr)$_4$ (4.45 mL, 16.2 mM). The resulting solution was allowed to stir at room temperature (RT) for 18 hr, and then quenched with saturated aqueous NH₄Cl and diluted with EtOAc. The mixture was filtered through a pad of celite, and washed with EtOAc. The layers were separated, and the organic phase was washed with brine, dried (MgSO₄) and concentrated to give the crude residue which was purified by column chromatography (Isco 40 g) eluting with a gradient of Hexanes/EtOAc (70/30 to 30/60) to afford the desired imine 2 (2.2 g, 78%).

concentrated in vacuo. The crude residue was diluted with EtOAc and the organic layer was washed with saturated aqueous NaHCO₃, brine, dried (MgSO₄) and concentrated. The crude residue 4 was used as such in the next step. (1.16 g, 97%).

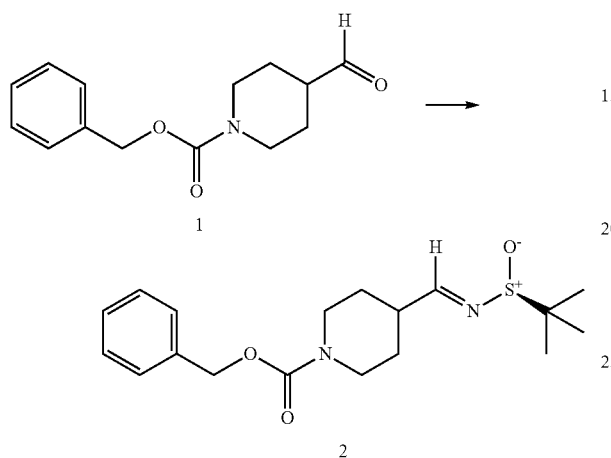

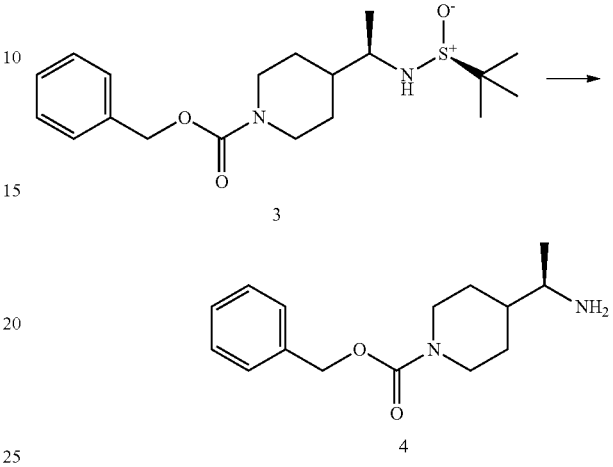

To a solution of imine 2 (2.2 g, 6.3 mM) in CH₂Cl₂ (20 mL) at −78° C. was added MeMgBr (3.1 mL, 3.0 M in Et₂O, 9.3 mM). The reaction was maintained at −78° C. for 1 hr, and then allowed to warm slowly to RT overnight. The reaction was quenched with saturated aqueous NH₄Cl and diluted with EtOAc and the layers were separated. The organic layer was washed with saturated aqueous NaHCO₃, brine, dried (MgSO₄) and concentrated. The crude residue was purified by column chromatography (Isco 80 g) eluting with a gradient of Hexanes/EtOAc (70/30 to 10/90) to afford the desired material 3 (1.67 g, 73%).

To a solution of amine 4 (1.16 g, 4.4 mM) in CH₂Cl₂ (50 mL) was added DIPEA (0.77 ml, 4.4 mM) followed by Boc₂O (3.2 g, 14.6 mM). The resulting solution was allowed to stir at RT overnight. The reaction was then quenched with water and diluted with EtOAc. The layers were separated and the organic phase was washed with saturated aqueous NaHCO₃, brine, dried (MgSO₄) and concentrated to give the crude derivative which was purified by column chromatography (Isco 80 g) eluting with a gradient of Hexanes/EtOAc (90/10 to 50/50) to afford the desired material 5 (1.55 g, 97%).

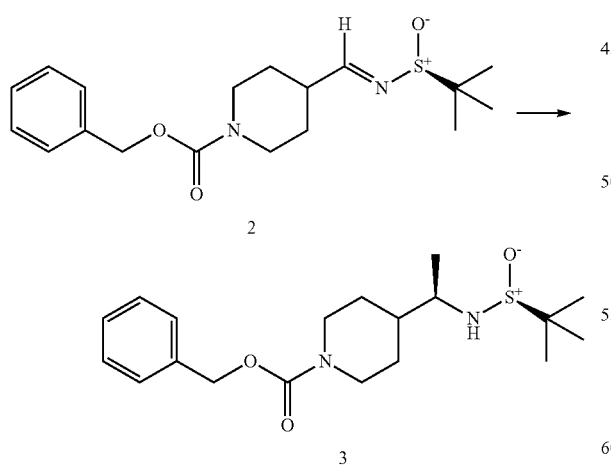

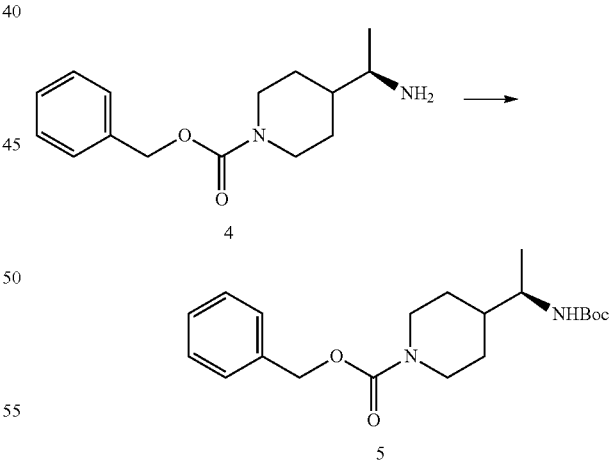

To a solution of sulfinamide 3 (1.67 g, 4.56 mM) in MeOH (50 mL) was added HCl (25 ml, 4 M in dioxane, 6.25 mM). The reaction was aged at RT monitoring disappearance of starting material by analytical reverse-phase HPLC. When the starting material was consumed, the reaction was To a solution of Cbz derivative 5 (1.55 g, 4.3 mM) in MeOH (50 mL) was added palladium on charcoal 10% (155 mg). The resulting suspension was purged twice with hydrogen and the reaction was allowed to stir at RT overnight under 1 atmosphere of hydrogen. The reaction was purged with nitrogen then diluted with CH₂Cl₂, filtered through celite and concentrated to give the crude derivative 6 which was used as such in the next step (0.98 g, quant.).

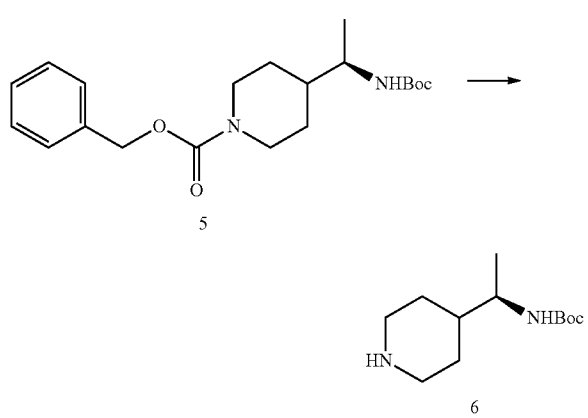

5

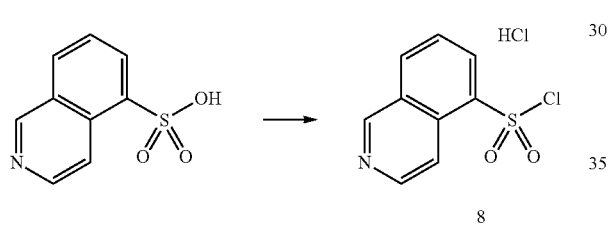

6

To a flask containing 5-isoquinolinesulfonic acid (5 g, 24 mM) was added $SOCl_2$ (22 ml, 300 mM) followed by a catalytic amount of DMF (0.25 ml). The resulting mixture was allowed to stir at reflux for 4 hr. It was then cooled down and concentrated in vacuo. The residue was purified by trituration with $CH_2Cl_2$ to yield the desired sulfonyl chloride 8 as a white solid (4.2 g, 66%).

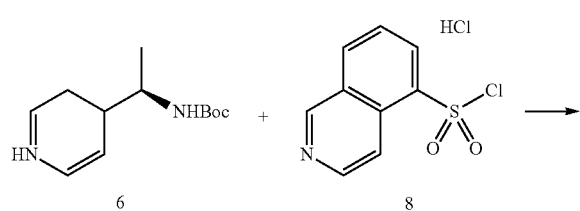

To a solution of amine 6 (1.0 g, 4.4 mM) in $CH_2Cl_2$ (50 mL) was added DIPEA (2.3 ml, 13.1 mM) followed by the sulfonyl chloride 8 (1.73 g, 6.6 mM). The resulting solution was allowed to stir at RT overnight. The reaction was then quenched with water and diluted with EtOAc. The layers were separated and the organic phase was washed with saturated aqueous $NaHCO_3$, brine, dried ($MgSO_4$) and concentrated to give the crude derivative which was purified by column chromatography (Isco 80 g) eluting with a gradient of Hexanes/EtOAc (70/30 to 100%) to afford the desired material 7. An analytical sample injected on a chiral HPLC showed an enantiomeric excess ("ee") of 95%. Recrystallization from $CH_2Cl_2$/$Et_2O$/Hexanes affords the desired material 7 as a white solid and ee >99%. (750 mg, 41%).

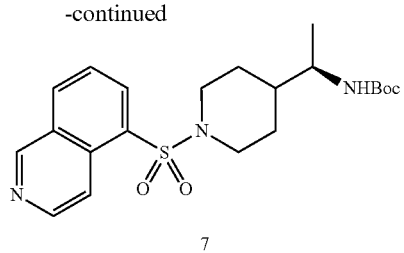

To a solution of the Boc derivative 7 (0.75 g, 1.8 mM) in $CH_2Cl_2$ (15 mL) was added HCl (4 M in dioxane, 5 ml, 20 mM). The reaction was stirred at RT overnight. The reaction was then concentrated in vacuo. The crude residue was diluted with a minimum of MeOH and added slowly to a flask containing $Et_2O$. The heterogeneous mixture was stirred for 5 min then filtered to provide BA-1049 (R) as a white solid (650 mg, 93%). $^1$H NMR ($CH_3OH$-$d_4$, 400 MHz): δ 9.97 (1H, s), 9.18 (1H, d, J=6.9 Hz), 8.76-8.81 (3H, m), 8.18 (1H, t, J=7.9 Hz), 3.98-4.01 (2H, br d, J=12 Hz), 3.15 (1H, p, J=6.6 Hz), 2.62 (2H, t, J=12 Hz), 1.79-1.84 (2H, m), 1.57-1.61 (1H, m), 1.40 (2H, qd, J=12, 4.1 Hz), 1.24 (3H, d, J=6.7 Hz).

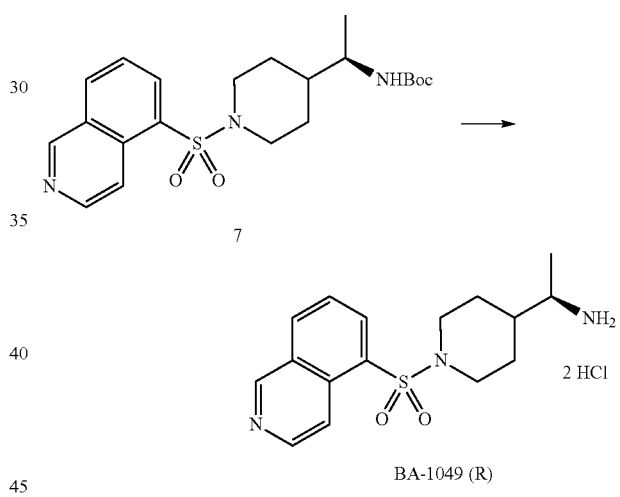

Example 2

Synthesis of 1-Hydroxy-BA-1049 (R)

The following scheme describes the synthesis of 1-hydroxy-BA-1049 (R) beginning with the same Boc derivative compound 7 shown above in EXAMPLE 1. The synthesis yields an already chirally selected compound so that the absolute stereochemistry is known.

To a flask containing the Boc derivative 7 (above) (1.2 g) was added 72 mL of DCM in a nitrogen purged atmosphere. The solution was stirred and cooled to 0-5° C. To the solution is added divided portions of meta-chloroperoxybenzoic acid (mCPBA; 0.9 g total) and the reaction was stirred overnight (ON) while being allowed to warm to RT. 30 mL of a 10% aqueous solution of $Na_2SO_3$ was added and stirred for 30 min. The product was purified by column chromatography (Isco 80 g; Fisher Scientific; Pittsburgh, Pa.)) to afford the desired material: N-oxide-Compound 7 (99.2%).

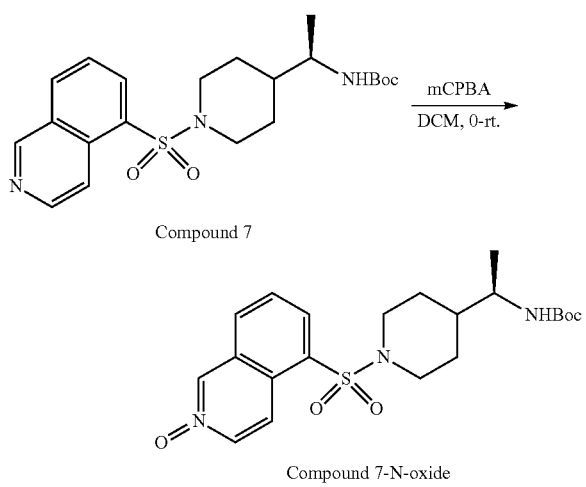

Compound 7

Compound 7-N-oxide

A flask purged with nitrogen was charged with 0.9 g of Compound 7 N-oxide and 9 mL of DCM was added with stirring. To this solution was added 0.2 g of the phase transfer catalyst tetrabutylammonium bisulfate (TBAB) and sodium acetate (NaOAc) in water (4.5 mL) with stirring. After a further 10 min of stirring, benzoyl chloride (BzCl) was added slowly to the mixture with stirring. The layers were separated and the organic phase was washed with saturated aqueous $NaHCO_3$, brine, dried ($MgSO_4$), and concentrated to give the crude derivative. The material was purified by column chromatography (98.9%) (Isco 80 g; Fisher Scientific).

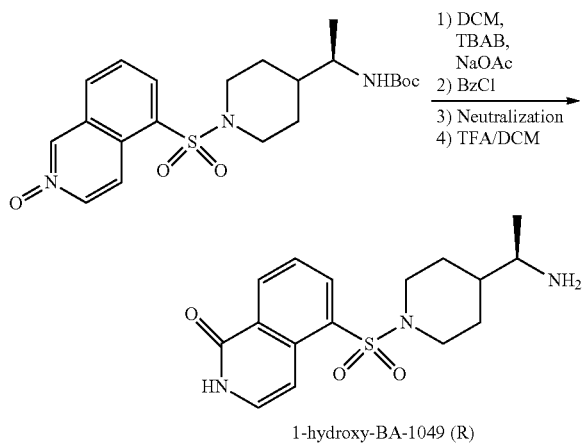

1-hydroxy-BA-1049 (R)

Example 3

Determination of BA-1049 Enantiomer Specificity for ROCK1 and ROCK2

A. Procedures

Compounds BA-1049 (R), BA-1049 (S) and other additional Rho kinase inhibitors (BA-1041, BA-1042, BA-1043, BA-1050, BA-1050A, and BA-1050B) were synthesized according to established protocols (U.S. Pat. No. 7,572,913). Compounds 1050 A and B are enantiomers that were purified by column chromatography, but the exact orientation was not identified, so they are termed A and B. Stock solutions for each compound were prepared at 100 mM in 100% DMSO and stored in an air tight container at −20° C. 10 mM working aliquots were prepared by diluting the stock solutions 1:10 in 100% DMSO. For $K_D$ determinations, 50 μL aliquots at 10 mM were prepared for each compound tested. For $IC_{50}$ determinations, compounds were prepared as 20 μL or 100 μL aliquots at 10 mM.

BA-1049 and BA-1050 exist as racemic mixtures with each having one chiral center. BA-1049 and BA-1050 were resolved into their respective enantiomers, (S) and (R) for BA-1049; BA-1050 enantiomers are called A and B because their absolute stereochemistry was not determined. 10 mM stock solutions were prepared in DMSO before storing the stock solutions at −20° C.

$IC_{50}$ determinations for BA-1049 were performed using a direct filter-binding radiometric kinase assay as described below. In one instance, ROCK1 and ROCK2 $IC_{50}$ determinations were made using an ATP concentration of 10 μM. In another instance, ROCK1 and ROCK2 $IC_{50}$ determinations were made using ATP concentrations of either 10 μM, or the Km ATP of 70 μM and 15 μM for ROCK1 and ROCK2, respectively. Variations in ATP concentrations were tested to better understand potential selectivity in ischemic and diseased tissue where ATP concentrations may be low and impact selectivity.

1. Equilibrium Dissociation Constant ($K_D$) Determinations $K_D$ values for the compounds to be tested and control articles for ROCK1 and ROCK2 were determined using the KINOMEscan™ Profiling Service (DiscoverX Corp, Freemont, Calif.). KINOMEscan™ is based on a competition binding assay that quantitatively measures the ability of a compound to compete with an immobilized, active-site directed ligand. The assay is performed by combining the DNA-tagged kinase, immobilized ligand, and a test compound. The ability of the test compound to compete with the immobilized ligand is measured via quantitative PCR of the DNA tag.

Compounds were tested using an 11-point curve with 3-fold serial dilutions. The highest concentration tested was 30 μM. Test compounds were prepared in 100% DMSO at 100× final test concentration and were diluted to 1× in the assay with a final DMSO concentration of 1%.

Streptavidin-coated magnetic beads were treated with biotinylated small molecule ligands for 30 min at RT to generate affinity resins for kinase assays. The ligand-bound beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, ligand-bound affinity beads, and test compounds in 1× binding buffer (20% SeaBlock, 0.17×PBS, 0.05% Tween 20, 6 mM DTT). All reactions were performed in polystyrene 96-well plates in a final volume of 0.135 mL. The assay plates were incubated at RT with shaking for 1 hr. The affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at RT with shaking for 30 min. The kinase concentration in the eluates was measured by qPCR.

Curves were fitted in GraphPad Prism 6.07 using non-linear least square fit with the Levenberg-Marquardt algorithm. Binding constants ($K_D$ values) were calculated with a standard dose-response curve using the Hill equation with the Hill Slope set to 1:

$$\text{Response} = \text{Background} + \frac{\text{Signal} - \text{Background}}{1 + \left(K_D^{Hill\ Slope} / \text{Dose}^{Hill\ Slope}\right)}$$

2. Half Maximal Inhibitory Constant ($IC_{50}$) Determinations $IC_{50}$ values for test articles and control articles for ROCK1 and ROCK2 were determined using the Kinase HotSpot™ Profiling Service (Reaction Biology Corp., Malvern, Pa.), and the $IC_{50}$ Profiler™ (Eurofins Pharma Discovery Services, St. Charles, Mo.). Both services use a direct filter-binding, radiometric kinase assay with slight variation in protocol.

Compounds were tested using an 11-point curve with 3-fold serial dilutions. The top concentration tested was 100 µM for both services. Test compounds were prepared in 100% DMSO at 50× final test concentration and were diluted to 1× in the assay with a final DMSO concentration of 2%.

For one assay, the substrate EAKEKRQEQIAKRRRL SSLRASTSKSGGSQK (SEQ ID NO:1) (30 µM) was mixed with reaction buffer (Table 4) and the kinase domain from either the ROCK1 or ROCK2 (as indicated in Table 4). Next, the compounds (in DMSO) were delivered into the mixture via acoustic mixing technology (Echo550, nanoliter range) (SelectScience, Waltham, Mass.), and incubated at RT for 20 min. Radiolabeled γ-$^{33}$P-ATP (10 µM) was added and the reaction incubated for 2 hr at RT. Reactions were then spotted onto P81 ion exchange paper followed by scintillation counting.

For the other assay, ROCK1 or ROCK2, was incubated with reaction buffer, substrate, 10 mM Mg acetate and γ-$^{33}$P-ATP (10 µM or Km concentrations) (see Table 4) and incubated for 40 min at RT. The reaction was stopped by the addition of 3% phosphoric acid and 10 µL of the reaction was spotted onto P30 filtermat, washed 3 times in 75 mM phosphoric acid and once in methanol prior to scintillation counting.

Curves were fitted in GraphPad Prism 6.07 using 4 parameter logistic nonlinear regression.

$IC_{50}$ values were calculated from the dose-response curves with variable slopes as follows:

$$Y = \text{Bottom} + \frac{(\text{Top} - \text{Bottom})}{1 + 10^{(Log\ IC_{50} - x) * Hill\ Slope}}$$

Raw data was captured in Microsoft Excel 2013. Data from Microsoft Excel was transferred GraphPad Prism 6.07 to derive dose-response curves and calculate $K_D$ and $IC_{50}$ values. Standard error of the mean (SEM) was calculated using Microsoft Excel 2013. Data was presented as the average value plus or minus SEM.

B. Results

1. $K_D$ Determinations

Determinations were performed in duplicate and the results are presented as average determinations in Table 5.

TABLE 5

| Compound ID | ROCK1 $K_D$ (nM) | ROCK2 $K_D$ (nM) | Fold-Difference |
|---|---|---|---|
| BA-1041 | 760 | 800 | 1.0 |
| BA-1042 | 370 | 280 | 1.3 |
| BA-1043 | 270 | 230 | 1.2 |
| Racemic BA-1049: Lot 1* | 54 | 46 | 1.2 |
| BA-1049A* | 155 | 160 | 0.9 |
| BA-1049B* | 99 | 63 | 1.6 |
| Racemic BA-1049: Lot 2 | 89 | 66 | 1.3 |
| BA-1050 | 150 | 160 | 0.9 |
| BA-1050A | 210 | 190 | 1.1 |
| BA-1050B | 370 | 280 | 1.3 |
| Fasudil | 50 | 45 | 1.1 |
| SLX-2119 (KD025) | 7400 | 65 | 113.8 |

*Repeat determinations performed

Equilibrium dissociation constants ($K_D$ values) were performed on different racemic lots of BA-1049 (Lots 1 and 2)

TABLE 4

| Kinase Domain | CRO | Kinase Sequence Expressed* | Expression System | Tag | Assay Buffer |
|---|---|---|---|---|---|
| ROCK1 | RBC | 1-535 | Insect | GST | 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO |
| ROCK1 | Eurofins | 14-535 | Insect | His | 20 mM MOPS, 1 mM EDTA, 0.01% Brij-35, 5% Glycerol, 0.1% 6-mercaptoethanol, 1 mg/mL BSA |
| ROCK2 | RBC | 5-554 | Insect | GST | 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO |
| ROCK2 | Eurofins | 11-552 | Insect | His | 50 mM TRIS, 0.1 mM EGTA, 0.1% 6-mercaptoethanol, 1 mg/mL BSA |

*Amino acid range of recombinantly produced proteins used in assay as compared to numbers of the full-length human enzyme Counts per min (cpm) were converted to percent activity as follows:

$$\% \text{ Activity} = \frac{(A - B)}{C} * 100$$

A=cpm for test article
B=cpm of blank (reaction without kinase domain)
C=Mean cpm of control (reaction with kinase domain alone)

as well as the enantiomers, R and S. The analysis also included six other Rho kinase inhibitors selected based on their structural similarity to BA-1049 and their ability to selectively inhibit ROCK2. These compounds were included BA-1041, BA-1042, BA-1043, BA-1050 and its enantiomers, A and B.

As shown in Table 5, BA-1049 and its enantiomers showed the strongest binding to both ROCK1 and ROCK2 (nM range) relative to the other Rho kinase inhibitors and the data confirmed that BA-1049 remained the strongest Rho kinase II selective inhibitor. ROCK2 $K_D$ values were similar to that of Fasudil, a known ROCK1/2 kinase inhibitor and a ROCK2 selective inhibitor, SLx-2119 (KD025). Repeat determinations were performed for the newly synthesized lot of BA-1049 and its enantiomers (Lot 2) and confirm the results of the first determinations. $K_D$ values for these compounds represent the average of 2 duplicate determinations (i.e., 4 determinations).

2. $IC_{50}$ Determinations

Using BA-1049, $IC_{50}$ values for both ROCK1 and ROCK2 were determined using an ATP concentration of 10 µM. While most kinase inhibitors compete with ATP binding, 10 µM is often used for screening, despite physiological levels being in the mM range. Two different variations on the direct filter-binding radiometric kinase assay were used, as detailed above. The results are shown in Table 6.

TABLE 6

| Compound ID | CRO | Compound $IC_{50}$ (µM) | | Fold-Difference |
|---|---|---|---|---|
| | | ROCK1 10 µM ATP | ROCK2 | |
| Racemic BA-1049: Lot 1 | Reaction Biology | 1.28 | 0.60 | 2.1 |
| | Upstate Cell Signaling | 10.2 | 0.80 | 12.8 |
| Racemic BA-1049: Lot 2 | Reaction Biology* | 1.02 (±0.28) | 1.02 (±0.28) | 2.8 |
| | Eurofins | 6.80 | 0.55 | 12.4 |
| BA-1049A | Reaction Biology* | 1.44 (±0.25) | 0.72 (±0.18) | 2.0 |
| | Eurofins | 10.2 | 0.73 | 14.1 |
| BA-1049B | Reaction Biology* | 0.69 (±0.05) | 0.34 (±0.02) | 2.0 |
| | Eurofins | 3.90 | 0.24 | 16.2 |

*Repeat determinations performed

These results show that BA-1049 and its enantiomers selectively inhibit ROCK2. In one instance, there was a 2-3 fold-difference in ROCK2 selectivity, whereas in another instance the data showed an approximate 12-13-fold difference in ROCK2 selectivity. BA-1049B had the lowest $IC_{50}$ value (0.24 µM) for ROCK2 and showed the best ROCK2 selectivity. Differences in ROCK2 selectivity are most likely due to differences in the preparation of the individual kinase domains used in the respective assays. Purity of the kinase domain can have a significant impact on the ability of compound to bind and therefore to inhibit. In addition, these compounds include a small 6×His tag for purification which remains on the kinase domain, while Reaction biology uses a 26 kDa GST protein fused to the kinase domain.

The $IC_{50}$ values for BA-1049 (S) and BA-1049 (R) were determined at the Km ATP concentration for both ROCK1 (70 µM) and ROCK2 (15 µM), an artificial assay to understand what might happen if the ATP concentration fell below the Km of ROCK1. In this case the maximal velocity of the reaction would be slower, and BA-1049 (R) would continue to be active against ROCK2. The results are shown in Table 7.

TABLE 7

| | Compound $IC_{50}$ (µM) | |
|---|---|---|
| Compound ID | ROCK1 70 µM ATP | ROCK2 15 µM ATP |
| BA-1049 (S) | 57.9 | 1.00 |
| BA-1049 (R) | 29.6 | 0.34 |

The data show a 50- to 60-fold greater selectivity for ROCK2 relative to ROCK1.

Example 4

Determination of Dose and Route of Administration of BA-1049 (R)

The murine intraluminal monofilament model of middle cerebral artery occlusion (MCAO) is used on mice in this study. MCAO involves the insertion of a surgical filament into the external carotid artery and threading it forward into the internal carotid artery until the tip occludes the origin of the MCA, resulting in a cessation of blood flow and subsequent brain infarction in the MCA territory. The technique is used herein to model transient occlusion. If the filament is removed after 1 h, reperfusion is achieved (transient MCAO). This study determines the most efficacious dose and route of administration that reduce Rho-kinase 2 (ROCK2) activation following transient MCAO-induced stroke in mice. The pharmacodynamic response is also determined in this study. This model rapidly detects BA-1049 (racemic mixture) and BA-1049 (R) efficacy in endothelial cells through the use of well characterized biomarkers for ROCK2 activity, phosphorylated adducin (p-adducin), phosphorylated myosin light chain 2 (pMLC2), phosphorylated cofilin (phospho-cofilin), phosphorylated LIMK1/2, and autophosphorylated ROCK2. Following efficacious route and dose selection, a time course is performed to assess the duration of the effect of BA-1049 (racemic mixture) based on duration of biomarker expression.

A. Animal Testing

Twenty-eight 9-wk old C57BL/6 (Charles River Laboratories) were used in this study. For surgery, the mouse was placed in a supine position on an infrared heating pad. The fur over the ventral neck was shaved and the skin was disinfected with 70% ethanol and povidone iodine. Under a stereo dissecting microscope, a 1 cm midline incision was made on the neck and retractors were used to expose the left common carotid artery (CCA), the external carotid artery (ECA) and the internal carotid artery (ICA). The arteries were carefully dissected to free them from surrounding nerves and fascia. The ECA was dissected further distally and two 8-0 silk sutures are tied around the ECA stump and a vascular clamp was applied at the bifurcation of the CCA into the ECA and ICA. A small incision was made at the end of ECA stump with Vannas-style spring scissors. A blunt 5-0 monofilament suture (Doccol) was inserted into the incision and advanced from the lumen of the ECA into the ICA for a distance of 9-10 mm beyond the bifurcation of CCA to occlude the origin of MCA. For the mouse model, a distance of 9 mm-11 mm rostral to the CCA bifurcation is inserted. After 60 min., the monofilament was removed. The incision was sutured with 4.0 prolene sutures. One mL saline was injected subcutaneously and 0.1 mg/kg buprenorphine was injected subcutaneously every 8 hr to 12 hr for up to 48 hr to decrease pain. The mouse is allowed to recover on a heating pad until thermoregulation is re-established.

The test Rho kinase inhibitor compound dosing solutions were prepared by dissolving BA-1049 powder (racemic mixture) and BA-1049 (R) in sterile PBS in order to achieve concentrations of 10 mg/mL, 25 mg/mL, and 50 mg/mL for groups B, C, and D, respectively. The pH of test compound dosing solutions was adjusted to 7. After preparation, the dosing solutions were kept at 4° C. until use, retained dosing solutions are stored at 4° C.

The test compound dosing solutions were prepared by dissolving Fasudil (Calbiochem) powder in sterile PBS in order to achieve concentrations of 10 mg/mL, 25 mg/mL, and 50 mg/mL. The pH of test compound dosing solutions was adjusted to 7. After preparation, the dosing solutions are kept at 4° C. until use. Retained dosing solutions were stored at 4° C.

The study consisted of 3 parts as follows in Tables 8 through 11:

TABLE 8

Part 1: Determination of an efficacious dose of BA-1049 vs. Fasudil, intraperitoneal (I.P.) inj.

| Group | N | Surgical Procedure | Route | Treatment, Dose |
|---|---|---|---|---|
| 1 | 4 | Transient (60 min.) MCAO | I.P. | PBS |
| 2 | 4 | Transient (60 min.) MCAO | I.P. | BA-1049 (racemate), 10 mg/kg |
| 5 | 4 | Transient (60 min.) MCAO | I.P. | Fasudil, 10 mg/kg |

TABLE 9

Part 2a: Determination of Optimal Delivery Method, I.P. vs. Oral Gavage (PO)

| Group | N | Surgical Procedure | Route | Treatment, Dose BA-1049 (racemic) |
|---|---|---|---|---|
| 1 | 4 | Transient (60 min.) MCAO | I.P. | 10 mg/kg |
| 2 | 4 | Transient (60 min.) MCAO | PO | 10 mg/kg |
| 3 | 4 | Transient (60 min.) MCAO | PO | 25 mg/kg |
| 4 | 4 | Transient (60 min.) MCAO | PO | 50 mg/kg |

TABLE 10

Part 2b: Determination of Optimal Delivery Method, IP vs. SC

| Group | N | Surgical Procedure | Route | Treatment, Dose BA-1049 (racemic) |
|---|---|---|---|---|
| 1 | 4 | Transient (60 min.) MCAO | I.P. | 10 mg/kg |
| 4 | 4 | Transient (60 min.) MCAO | SC | 10 mg/kg |
| 5 | 4 | Transient (60 min.) MCAO | SC | 25 mg/kg |
| 6 | 4 | Transient (60 min.) MCAO | SC | 50 mg/kg |

TABLE 11

Part 3: Time Course of BA-1049 Efficacy Following Selection of Best Route and Dose

| Group | N | Surgical Procedure | Route | Treatment, Dose BA-1049 (racemic) | Collection post-MCAO |
|---|---|---|---|---|---|
| Dose and perform MCAO surgery on Groups 1-3 | | | | | |
| 1 | 4 | Transient (60 min.) MCAO | TBD | TBD mg/kg | 1 d |
| 2 | 4 | Transient (60 min.) MCAO | TBD | TBD mg/kg | 2 d |
| 3 | 4 | Transient (60 min.) MCAO | TBD | TBD mg/kg | 3 d |
| Analyze Groups 1-3, if biomarkers persist dose and perform MCAO surgery on Group 4 | | | | | |
| 4 | 4 | Transient (60 min.) MCAO | TBD | TBD mg/kg | 7 d |
| Analyze Group 4, if biomarkers persist dose and perform MCAO surgery on Group 5 | | | | | |
| 5 | 4 | Transient (60 min.) MCAO | TBD | TBD mg/kg | 12 d |

For Part 1, the test articles (BA-1049 racemic, BA-1049 (R), Fasudil) and (saline) were administered at the specified dose at a volume of about 0.2 mL (volume was adjusted based on individual body weights) to all mice as a single dose I.P. 30 min after MCAO surgery using sterile 1 mL-syringes fitted with a 25 G 5/8 needle.

For Part 2a/2b, the test and vehicle articles were administered at the specified dose at a volume of about 0.2 mL (volume is adjusted based on individual body weights) to all mice by either oral gavage (PO) (<10 mg/kg) 30 min after MCAO surgery (2a) or subcutaneous (SC) injection in the right flank 30 min after MCAO surgery (2b) using sterile 1 mL-syringes fitted with a 25 G 5/8 needle.

At 24 hr post-MCAO surgery, mice were euthanized and brains are collected for biomarker analysis by Western blot analysis or immunohistochemistry. For Western blot analysis, mice were anesthetized using isoflurane and decapitated. The right and left middle cerebral arteries supply the lateral surface of their respective lobes in the territory of the motor and sensory cortices. The brain rostral to the cerebellum (excluding olfactory bulb) was collected ipsilateral (left hemisphere) and contralateral (right hemisphere) to the occlusion. Ipsilateral and contralateral hemispheres are collected in 2 separate tubes. Frozen brain tissue was further processed into tissue lysates following the experimental protocol documented below.

For immunohistochemistry, mice were anesthetized using isoflurane and perfused intracardially using paraformaldehyde (4% PFA), brain and weights were recorded. Brain specimens from fixed animals were frozen in OCT and sectioned using a cryostat.

B. Tissue Lysate Preparation and Quantification

20 μL protease inhibitor (Halt, Protease, Fisher Scientific, Pittsburgh, Pa.) and 10 μL phosphatase inhibitor (Fisher Scientific) were added to 1 mL RIPA buffer (Santa Cruz Biotechnology, Dallas, Tex.). 0.5 mL lysis buffer was added to each tissue sample and the tissues ground individually using a clean BioMasher II® tube/pestle (Kimble Chase Life Science, Vineland, N.J.) for each sample. The mixture was vortexed to aid in tissue lysis and centrifuged at 4° C. for 10 min at 13,000 rpm. The supernatants from each tube were collected. The protein concentration of each sample was determined using the DC Protein Assay Kit and following the manufacturer's instructions.

C. Western Immunoblotting

Protein lysates were analyzed by Western blot analysis following the experimental protocol below in Table 12.

TABLE 12

| Primary Antibody | Dilution | Secondary Antibody | Dilution |
|---|---|---|---|
| pCofilin rabbit polyclonal (Cell Signaling Cat# 3313, lot# 7) | 1:500 | Anti-Rabbit IgG HRP (Cell Signaling Cat# 7074, lot #26) | 1:1500 |
| pROCK2 rabbit polyclonal (Genetex Cat# GTX122651, lot# 42025) | 1:500 | Anti-Rabbit IgG HRP (Cell Signaling Cat# 7074, lot #26) | 1:1500 |
| Cyclophilin 40 rabbit polyclonal (Santa Cruz Cat# sc-66848, lot# H3103) | 1:2000 | Anti-Rabbit IgG HRP (Cell Signaling Cat# 7074, lot #26) | 1:1500 |
| pMLC2 (Thr18/Ser19) rabbit polyclonal (Cell Signaling Cat#3674, lot# 3) | 1:1000 | Anti-Rabbit IgG HRP (Cell Signaling Cat# 7074, lot #26) | 1:1500 |
| pMLC2 (Ser19) rabbit polyclonal (Cell Signaling Cat#3671, lot# 3) | 1:500 | Anti-Rabbit IgG HRP (Cell Signaling Cat# 7074, lot #26) | 1:1500 |
| pAdducin Rabbit polyclonal (Santa Cruz Cat# sc-16738, lot# B0414) | 1:200 | Anti-Rabbit IgG HRP (Cell Signaling Cat# 7074, lot #26) | 1:1500 |
| pLIMK 1/2 rabbit polyclonal (Cell Signaling Cat#3841, lot# 6) | 1:500 | Anti-Rabbit IgG HRP (Cell Signaling Cat# 7074, lot #26) | 1:1500 |

The left and right hemispheres of each brain were homogenized and prepared for Western blotting, and the signal of phospho-cofilin was measured quantitatively by densitometry compared to an internal standard, cyclophilin.

Figure 8:
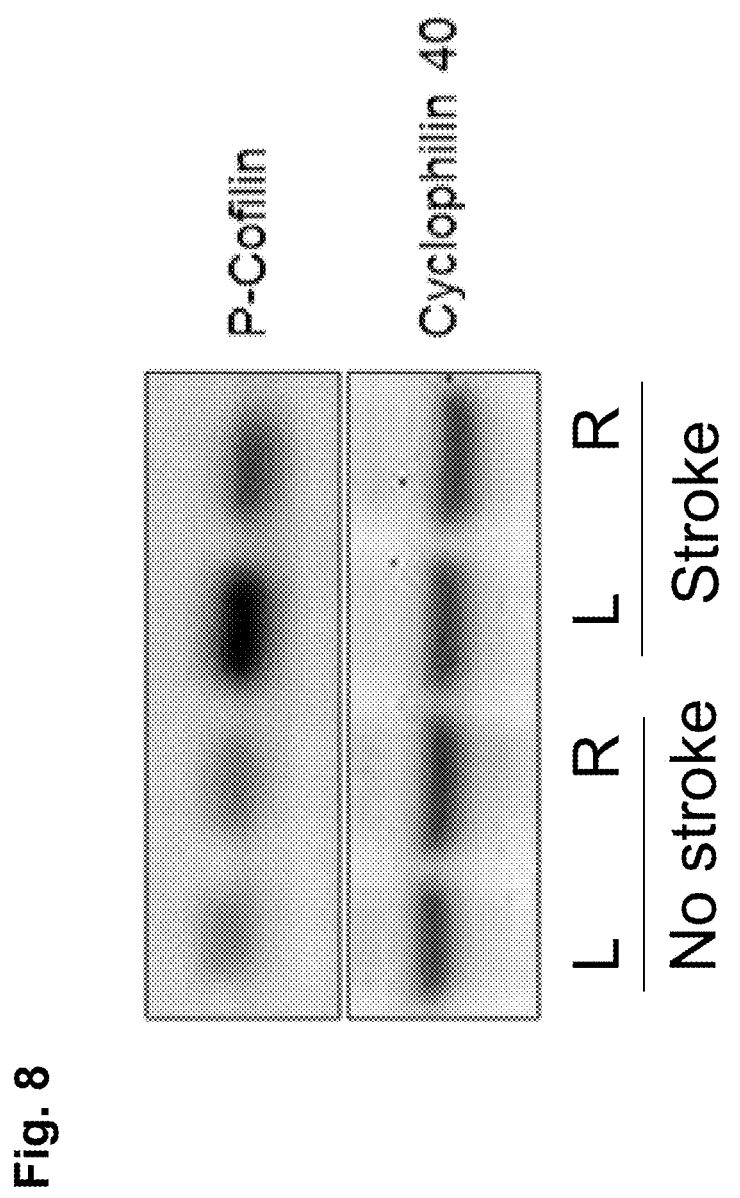
FIG. 8 is a representation of a Western blot of brain homogenates from a mouse that received a transient middle cerebral artery occlusion (stroke) compared to a normal mouse (no stroke), where tissue homogenates from the left (L) and right (R) hemispheres of the brain were probed with antibodies to phospho-cofilin, a downstream target of ROCK activity, and the left side of the stroke brain is the affected side and shows an increase in phospho-cofilin expression.
Figure 9:
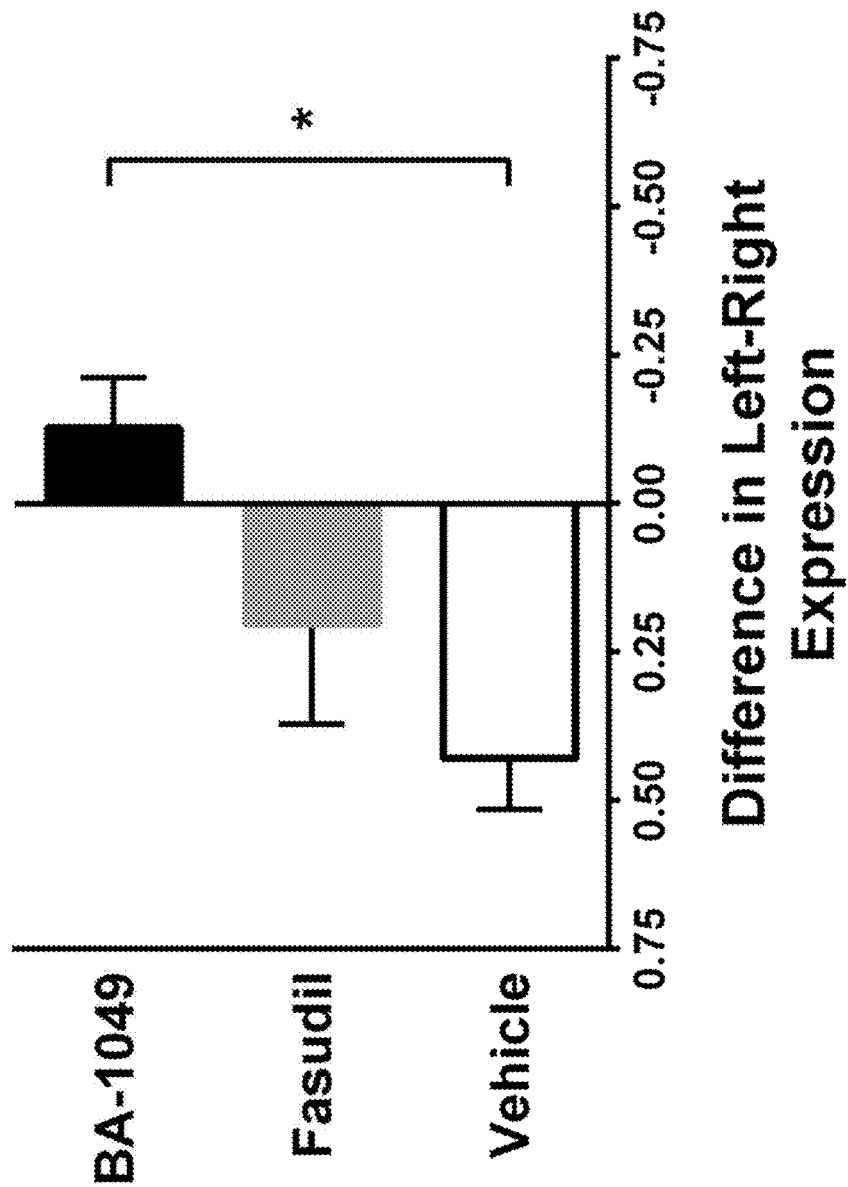
FIG. 9 is a graphic representation showing the left-right ratio of phospho-cofilin expression between the stroke and control hemispheres of the brain after MCAO and treatment with racemic BA-1049 or Fasudil, where BA-1049 strongly and significantly reduced the ratio of phospho-cofilin expression, as visible in the shift of the ratio close to 0, where 0 indicates equal expression on both sides of the brain.

FIG. 9 shows the results of Part 1 of the study outlined above and in Table 3. BA-1049 (10 mg/kg) was compared to Fasudil (10 mg/kg) and vehicle controls. Injections were made IP within 30 min of recovery after MCAO. Tissue was harvested 24 hr post MCAO. The ratio of phospho-cofilin signal in the left versus right hemispheres of the brain was examined using Western blotting. In these experiments, a reduction in the ratio of phospho-cofilin expression between the left (MCAO) and right (uninjured) sides demonstrates a reduction in ROCK activation and therefore an increase in ROCK inhibition by the given treatment. FIG. 8 shows that phospho-cofilin expression is strongly increased in the stroke side of the brain and acts as an effective biomarker for ROCK2 activation.

As shown in FIG. 9, the ratio of phospho-cofilin expression was strongly reduced by racemic BA-1049 and reduced to a lesser extent by Fasudil compared to vehicle-only controls. When the experiment is repeated with BA-1049 (R), the effect on reducing phospho-cofilin after MCAO is augmented. These experiments show 10 mg/kg BA-1049 (R) is efficacious in reducing ROCK2 activation by MCAO, as compared with Fasudil. Thus, these results show that BA-1049 (R) more strongly reduces phospho-cofilin than Fasudil when both are compared at 10 mg/kg.

D. Immunohistochemistry

Frozen tissue sections embedded in OCT were analyzed by immunohistochemistry. The left side of the brain slice contains ischemic tissue due to the MCAO while the right hemisphere acts as a control without ischemia. Brain slices were treated with antibodies listed in Table 13. Staining with these antibodies provide biomarkers for both ischemic area and ROCK2 activation.

TABLE 13

| Primary Antibody | Dilution | Secondary Antibody | Dilution |
|---|---|---|---|
| pCofilin rabbit polyclonal (Cell Signaling Cat# 3313, lot# 7) | 1:100 | Alexa 488 Anti-Rabbit IgG (Molecular Probes Cat# A11008, lot #1622775) | 1:500 |
| Von Willebrand's Factor rabbit polyclonal (Millipore Cat#AB7356, Lot# 2569161) | 1:250 | Alexa 488 Anti-Rabbit IgG (Molecular Probes Cat# A11008, lot #1622775) | 1:500 |
| pMLC2 (Thr18/Ser19) rabbit polyclonal (Cell Signaling Cat#3674, lot# 3) | 1:250 | Alexa 488 Anti-Rabbit IgG (Molecular Probes Cat# A11008, lot #1622775) | 1:500 |
| pMLC2 (Ser19) rabbit polyclonal (Cell Signaling Cat#3671, lot# 3) | 1:100 | Alexa 488 Anti-Rabbit IgG (Molecular Probes Cat# A11008, lot #1622775) | 1:500 |
| pAdducin rabbit polyclonal (Santa Cruz Cat# sc-16738, lot# B0414) | 1:250 | Alexa 488 Anti-Rabbit IgG (Molecular Probes Cat# A11008, lot #1622775) | 1:500 |
| IBA1 rabbit polyclonal (Wako chemicals Cat#019-1974, lot#SAN3725) | 1:250 | Alexa 488 Anti-Rabbit IgG (Molecular Probes Cat# A11008, lot #1622775) | 1:500 |

FIGS. 10A-10D show phospho-MLC2 (Ser19) staining in small blood vessels of insular cortex. Blood vessels are strongly stained in the insular cortex on the left (MCAO) side of the brain (FIG. 10A) while there is no staining of small vessels on the control (non-MCAO) side (FIG. 10B). Phospho-MLC2 is a downstream marker for ROCK2 activation. 10 mg/kg Fasudil injected intraperitoneally (I.P.) (FIG. 10C) reduces the amount of staining while 10 mg/kg BA-1049 (FIG. 10D) injected I.P. is even more effective than Fasudil at reducing small vessel staining. FIGS. 10E and 10F show Iba-1 immunoreactivity in the left brain striatum after MCAO and I.P. injection with vehicle (FIG. 10E) or BA-1049 (R) (FIG. 10F). Iba-1 immunoreactivity is a marker for microglia in the brain. Iba-1 staining intensity is increased in activated microglia, responding to ischemic damage in the brain. These results demonstrate that BA-1049 (R) reduces the microglial reaction to ischemia.

Example 5

Effective Dose of BA-1049 (R)

To determine the effective dose to reverse the activation of ROCK, the MCAO model as described above in EXAMPLE 4 was used. In these experiments, mice having received MCAO vessel occlusion and an intraperitoneal injection of doses of 0.1 mg/kg, 1 mg/kg, 3, mg/kg or 10 mg/kg or saline (vehicle) as control, ROCK activation is assessed by phospho-cofilin expression in left versus right brain. In this model, after a single application of BA-1049 (R), the minimal effective dose was 1 mg/kg as seen in FIGS. 11A and 11B. The minimal effective levels are less than 1 mg/kg with daily repeat dosing.

In a separate set of experiments, daily repeat dosing experiments were performed to assess adverse effects. Normal mice received 1 mg/kg or 10 mg/kg of BA-1049 (R) once daily by intraperitoneal injection for 2 weeks. During the course of the experiment, animals were monitored daily for the appearance of any clinical signs. Hematology, blood chemistry, and histopathology were followed at termination of the experiment.

In daily repeat dosing for 2 weeks, no abnormal findings related to daily dosing of BA-1049 (R) at 1 mg/kg and at 10 mg/kg were noted. Therefore, the therapeutic dose of BA-1049 (R) shown in FIGS. 11A and 11B is below the no observed effect level dose of 10 mg/kg determined from the 2 week repeat dose experiments.

Example 6

Pharmacodynamic Response

To determine the pharmacodynamic response mice were subject to MCAO and then the ratio of left brain to right brain phospho-cofilin levels determined as described above in EXAMPLE 4. Mice were examined 4 hr or 24 hr after reperfusion and administration of 10 mg/kg of BA-1049 (R).

As shown in FIGS. 12A and 12B, both time points showed efficacy, demonstrating efficacy of BA-1049 (R) for at least 24 hr. In further experiments, the mice were given BA-1049 (R) for 24 hr, 72 hr, or 168 hr prior to the MCAO. The results shown in FIG. 12C demonstrate that 3 days prior exposure to BA-1049 (R) prevents the hyperactivation of ROCK after MCAO.

Example 7

Endothelial Permeability Reversed by BA-1049 (R)

This study demonstrates the ability of BA-1049 (R) to reverse the endothelial cell permeability that occurs in the mouse MCAO model of stroke.

Mice were given an MCAO lesion, as described in EXAMPLE 4. Two hr after reperfusion, mice were injected I.P. with a 1.2% solution of Evans blue dye in PBS, which binds tightly to serum albumin. Two hr after MCAO, Evans blue was injected, and 4 hr since reperfusion, mice were sacrificed, perfused, decapitated, and their brains dissected as described in EXAMPLE 4.

Homogenates were prepared as in EXAMPLE 4 and then precipitated in 50% trichloroacetic acid to precipitate proteins and release Evans blue dye from the albumin. After spinning down proteins (at 10,000×g), supernatants were placed in a 96-well dish and the absorbance at 595 nm and fluorescence (535 Ex/642 Em) read using a Victor 2 Wallac plate reader (Perkin-Elmer; Branford, Conn.). Comparison to a standard curve allows a determination of Evans blue dye concentration in the sample and, therefore, a measure of permeability to albumin.

Figure 13B:
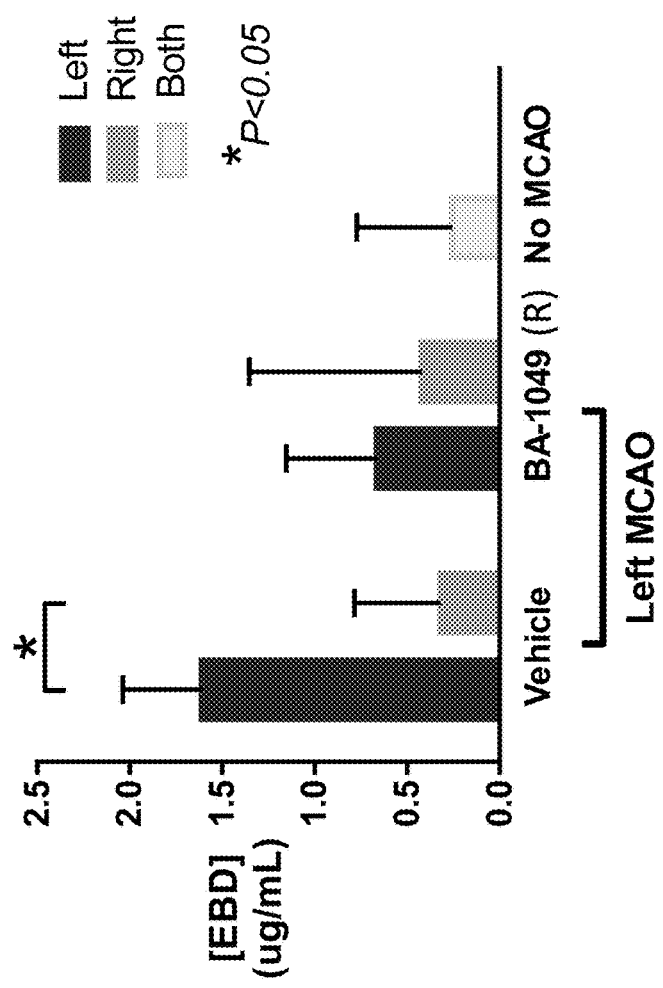
FIG. 13B shows a graphic representation of the results of FIG. 13A.
Figure 13A:
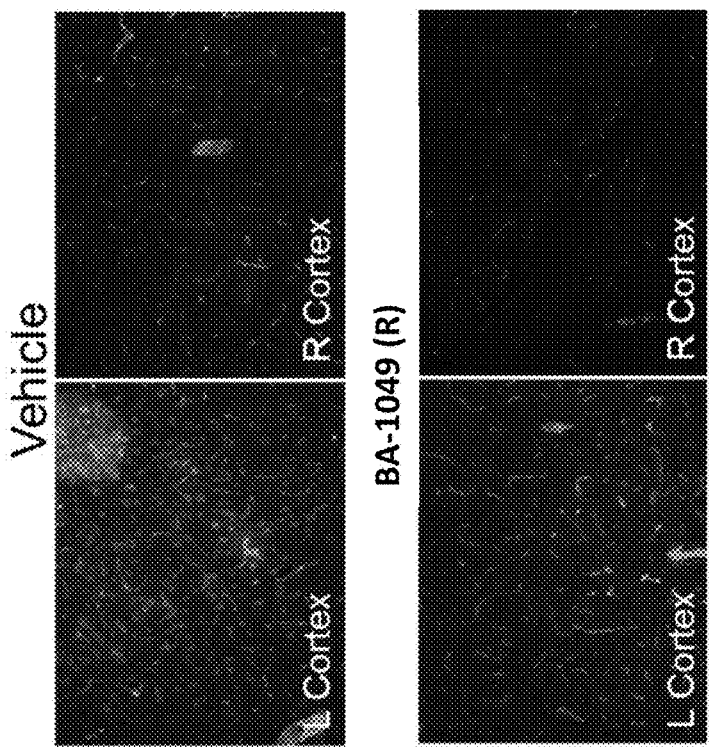
FIG. 13A shows photographic representations of the left (L) and right (R) cortex of mice treated with BA-1049 (R) or vehicle (control) after MCAO then injected with Evans blue, which appears red in the fluorescent image.

FIG. 13A shows micrographs of the brains of animals treated with Vehicle or BA-1049 (R). The Left (L) side is the ischemic side of the brain and is compared to the right (R) cortex. BA-1049 (R) reduces the fluorescent signal compared to the vehicle control. FIG. 13B shows a graphic representation of the results and shows that BA-1049 (R) treatment is able to reduce the Evans blue signal compared to the left brain of the vehicle control. These results demonstrate that BA-1049 (R) is able to reduce endothelial cell permeability.

Example 8

Routes of BA-1049 (R) Administration in C57BL/6 Mice (Non-GLP)

To determine the plasma concentrations and pharmacokinetics of the test compounds and test article following a single intravenous (IV) (5 mg/kg), intraperitoneal (IP) (10 mg/kg), or oral dose (PO) (30 mg/kg) administration to C57BL/6 male mice, the following testing [WAS/IS] performed according to the conductions set forth in Table 14.

TABLE 14*

| Route | Amount Delivered | Volume | Concentration of dosing solution | Volume of PBS needed | Weight of TA in vial |
|---|---|---|---|---|---|
| IV | 0.125 mg | 0.1 mL | 1.25 mg/mL | 3 mL | 3.75 mg |
| IP | 0.25 mg | 0.5 mL | 0.5 mg/mL | 15 mL | 7.5 mg |
| PO | 0.75 mg | 0.2 mL | 3.75 mg/mL | 6 mL | 22.5 mg |

*This table was generated based on providing enough test article to dose 30 mice of each route.

C57BL/6 mice, 8-10 weeks old (Charles River Labs, Wilmington, Mass.) were used in this study. The test drug is provided in Table 15 below:

TABLE 15

| Group # | No. of Mice/Sex | Route of Administration | Dose (mg/kg) | Dose Conc. (mg/mL) | Dose Vol. (mL/kg) | Dose Vol. (µL/g) |
|---|---|---|---|---|---|---|
| 1 | 24M | IV | 5 | 1.25 | 4.0 | 4 |
| 2 | 24M | IP | 10 | 0.5 | 20.0 | 20 |
| 3 | 24M | PO | 30 | 3.75 | 8.0 | 8 |
| 4* | 5M | — | — | — | — | — |

*Group 4 is for collection of naïve whole brain only and will not be dosed.

The test drug is provided once as follows: Each I.V. dosing syringe is weighed loaded and unloaded to at least 4 decimal places. The actual dose (5 mg/kg) administered to the animal is the difference between the loaded and unloaded dosing syringe weights. Each IP dosing syringe is weighed loaded and unloaded to at least 4 decimal places. The actual dose (10 mg/kg) administered to the animal is the difference between the loaded and unloaded dosing syringe weights. 30 mg/kg PO administration is conducted using a ball-tipped, stainless steel gavage needle attached to a plastic syringe.

A. Pharmacokinetics

1. Blood Sampling

Following I.V. dose administration, terminal blood samples (about 1 ml to 2 ml each) are collected from 4 animals at each of the following time points post-dose: 0.083 hr, 0.5 hr, 2 hr, 6 hr, 12 hr, and 24 hr. Following I.P. or PO dose administration, terminal blood samples (about 1 ml to 2 ml each) are collected from four animals at each of the following time points post-dose per dose route: 0.25 hr, 1 hr, 4 hr, 8 hr, 12 hr, and 24 hr. Each animal is anesthetized by $CO_2$ inhalation and terminal blood samples are collected via cardiocentesis and transferred into pre-labeled tubes containing sodium heparin as the anticoagulant. Following cardiocentesis blood collection, the animal is returned to the $CO_2$ chamber and euthanized by $CO_2$ asphyxiation. Collected blood samples are gently inverted several times to mix the anticoagulant.

B. Plasma Harvesting

Blood samples are centrifuged at about 3000×g rpm for 10 min at about 4° C., [resultant plasma is observed for hemolysis]. All derived plasma samples are stored frozen at approximately −80° C. until further processing.

C. Brain Harvesting

Following I.V. dose administration, whole brain is collected following cardiocentesis from 4 animals at each of the following time points post-dose: 0.083 hr, 0.5 hr, 2 hr, 6 hr, 12 hr, and 24 hr. Following I.P. and PO dose administration, whole brain is collected following cardiocentesis from 4 animals at each of the following time points post-dose per dose route: 0.25 hr, 1 hr, 4 hr, 8 hr, 12 hr, and 24 hr. Whole brain is rinsed in 1×PBS, the tissue weight recorded and snap frozen in pre-labeled tubes using liquid nitrogen. In addition, whole brain from 5 naïve mice is harvested at 24 hr, rinsed in 1×PBS, the tissue weight recorded and snap frozen in pre-labeled tubes using liquid nitrogen.

D. Bioanalytical Analysis

Samples are analyzed by LC/MS/MS using an Agilent 6410 mass spectrometer coupled with an Agilent 1200 HPLC and a CTC PAL chilled autosampler, all controlled by MassHunter software (Agilent). After separation on an X-Select HPLC column (Waters, 130A, 3.5 µm, 2.1×50 mm) using an acetonitrile-water gradient system (shown below), peaks were analyzed by mass spectrometry (MS) using ESI ionization in MRM mode.

Figure 14:
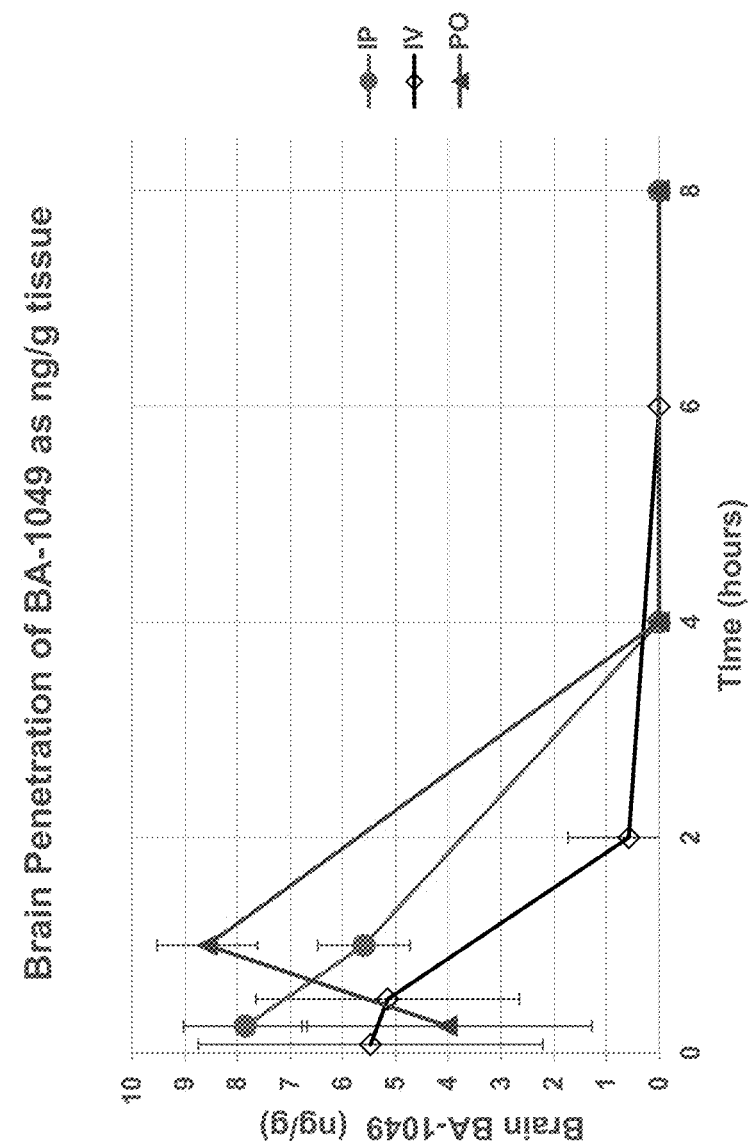
FIG. 14 is a graphic representation of the penetration of BA-1049 (R) detected in the brain following intraperitoneal (I.P.), intravenous (I.V.) or oral (PO) administration, measured as ng/g tissue.

For calibration samples, a working dilution of the test article at 25 times the final concentration is prepared and serially diluted (3-fold). These samples are diluted 25-fold into C57BL/6 mouse blank plasma and mixed with three volumes of acetonitrile containing an analytical internal standard (propranolol), incubated on ice for 10 min at 4° C. and then centrifuged. The protein-free supernatant is used for LC-MS/MS (liquid chromatography-tandem mass spectrometry) analysis. The results shown in FIG. 14 show that BA-1049 (R) is able to penetrate the brain by the three routes of administration.

Example 9

Effect of BA-1049 (R) and BA-1049 (S) on Neurite Outgrowth From NG108 Cells

BA-1049 (R) and BA-1049 (S) were compared for their effect on neurite outgrowth using a cell culture assay with NG-108 cells. First the effective dose for use with NG-108 cells was determined and then BA-1049 (R) was compared with a ROCK2 specific inhibitor SLx-2119.

BA-1049 (S) and BA-1049 (R) were compared for their effect on neurite outgrowth from NG-108 cells. As shown in FIG. 15D, BA-1049 (R) was the most potent compound to stimulate neurite outgrowth compared to the DMSO control (FIG. 15A), racemic BA-1049 (FIG. 15B), or BA-1049 (S) (FIG. 15C). Thus, BA-1049 (R) produces the most robust neurite outgrowth than the (S) compound.

As shown in FIGS. 16A-16C, 5 µM SLx-2119 was shown to be toxic to NG-108 cells, and cells showed formation of vacuoles and began to die (FIG. 16A). By contrast, BA-1049 (R) promoted neurite outgrowth at 5 µM (FIG. 16B) and 50 µM (FIG. 16C); BA-1049 (R) was not toxic to NG-108 cells at the highest concentrations tested (FIG. 16C).

Example 10

Effect of PTEN Silencing on the Expression of ROCK2

Neuronal cells were isolated from the developing brain cortex of embryonic rats using enzymatic and mechanical disruption methods and then plated onto specialized growth substrates including laminin and poly-D-lysine in a tissue culture dish. These cell mixtures were grown in a specialized medium under conditions of low serum containing specialized selected media additions (NeuroBasal Medium with B27 additive, Thermo Fisher Scientific, Waltham, Mass.) designed to enhance the survival of the neuronal cells in the dish. Neuronal cell cultures were grown in the dish for either 1 d (D1) or 7 d (D7) before they were exposed to 1 µM concentration of sdRNA molecules (sdRNA=self-delivering RNAi) that target the PTEN sequence or a non-related "non-targeting" control RNA sequence. The neuronal cultures were then incubated in the presence of these sdRNA molecules for a further 3 d. Proteins were extracted from the cultures in a Tris buffer based solution containing NP-40 and deoxycholic acid detergents by trituration and vortexing followed by centrifugation to eliminate non-soluble materials. Protein concentrations of the extracts were determined by modified Bradford assay and equivalent amounts of protein containing extract were analyzed by Western blot to determine whether there were specific changes in the amount of PTEN, ROCK2, or GAPDH proteins after treatment with the indicated sdRNA.

Figure 17:
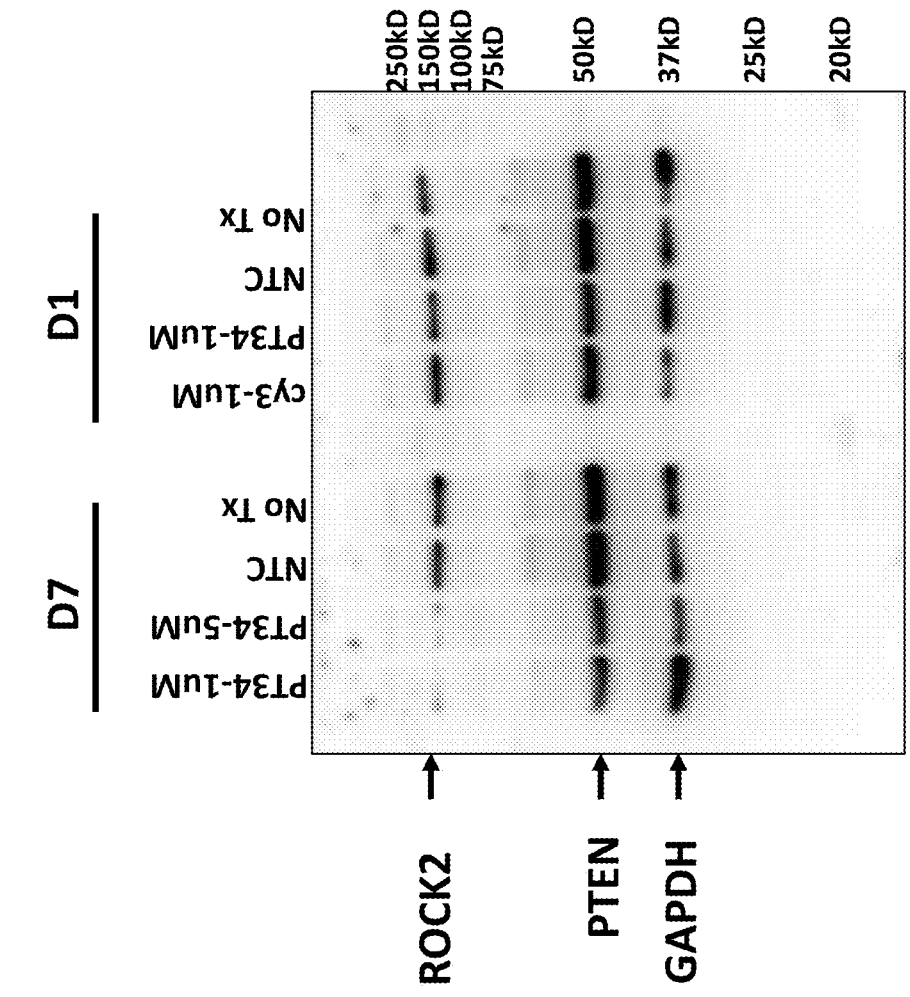
FIG. 17 is a representation of a Western blot of homogenates of primary rat cortical neurons treated for 3 days with RNAi against PTEN to knock down PTEN expression after 7 days in culture (D7) or after one day in culture (D1), showing ROCK2, PTEN, and GAPDH expression.

The results shown in FIG. 17 are from Western blotting experiments where levels of PTEN, ROCK2 and GAPDH proteins were analyzed. In the case of the neuron cultures grown for 7 days before treatment with the sdRNA (D7), targeting PTEN mRNA for reduction using PTEN-specific sdRNA leads to reduced PTEN protein levels in these cells, as expected. The reduction in PTEN protein levels also leads to a substantial reduction in the protein levels of the ROCK2 kinase. These data show that interventions that lead to decreases in PTEN protein can ultimately also lead to a decrease in ROCK2 protein as well. The ability to reduce total cellular ROCK2 activity by reducing the expression of PTEN may also be a component of what is currently known regarding the involvement of reducing PTEN activity in neural regeneration. This indicates that part of the effects that are seen when PTEN function is inhibited may ultimately be due to decreases in ROCK2 expression. Thus, the ability to inhibit ROCK2 selectively using BA-1049 (R) and produce regenerative effects may also be part of the pathway that is implicated when regeneration occurs as a result of interfering with PTEN.

ROCK2 expression is decreased by knockdown of PTEN, showing unexpectedly that ROCK2 is a promising target downstream of PTEN. Thus, BA-1049 which inactivates ROCK2 is a better target than PTEN for eliciting axon regeneration in the CNS.

Using both surgical injury to the corticospinal tract of the spinal cord in a group of 12 mice (central nervous system), the optic nerve in a group of 12 animals, and the sciatic nerve of the peripheral nervous system in an additional group of 12 mice, 5 µL of 1 µM BA-1049 (R) or control saline solution (per group of 6 mice) is applied during surgery by direct injection at the injury site at the time of the experimental injury and the animals recovered for 2 to 4 weeks after injury. At the time of sacrifice, changes in the relative extent of regeneration are measured using histological techniques. One day prior to sacrifice, fluorescent tracer molecules such as labeled cholera toxin are injected into the motor cortex to stain the axons that project into the spinal cord, in the eye to measure retinal ganglion cell axon regeneration, or in the case of the sciatic nerve, injection of labeled dextran amine proximal to the spinal cord at the region of the nerve roots allows for the characterization, by anterograde labeling, of the peripheral nerve axons. Sections are prepared the next day following the sacrifice and perfusion of the animal with fixative. The sections are collected onto glass slides and then the fluorescent markers are visualized through the microscope and the distance to which the labeled regenerating axons are growing are measured in a series of photographs taken of the specified sections. The lengths of the labeled axons are compared between the animals treated with BA-1049 (R) and those treated simply with saline injections.

Animals treated with BA-1049 (R) show regeneration in the central nervous system (e.g., corticospinal tract and optic nerve) compared to untreated animals; more axons in the peripheral nerves regenerate and reach their targets, compared to controls.

Example 11

Effect of BA-1049 (R) on Endothelial Cells

To determine the effects of BA-1049B (R) on ROCK hyperactivation and endothelial barrier function, human umbilical vein endothelial cells (HUVECs) are used. ROCK hyperactivation is induced by administration of lysophosphatidic acid (LPA)(Sigma-Aldrich, St. Louis, Mo.), a potent activator of the Rho/ROCK pathway. BA-1049 (R) efficacy is determined by investigating actin stress fiber formation, a biomarker for ROCK activity, and distribution of the focal adhesion complex protein vinculin, a biomarker for endothelial barrier integrity.

A. Cell Culture and LPA Stimulation

Primary HUVEC cells (Gibco®, Thermo Fisher, Waltham, Mass.) are cultured in endothelial growth media (Gibco® Medium 200 basal media Cat supplemented with Gibco® Large Vessel Endothelial Supplement). HUVECs between passage 1 and 4 are used for all experiments. HUVECs are cultured on poly-D-lysine-treated glass coverslips (Corning, Corning, N.Y.) coated with 70 µg/ml rat collagen I (Corning, Corning, N.Y.) and cultured for 4 d until a confluent monolayer of cells is established. Before LPA stimulation, cells are serum-starved for 1 hr using Medium 200 supplemented with 0.1% human serum albumin containing 50 µM BA 1049 (R), 50 µM Fasudil, or vehicle (DMSO) respectively. Then HUVECs are stimulated with 20 µM LPA for 10 min and subsequently fixed using 4% paraformaldehyde (PFA)/sucrose solution.

B. Immunocytochemistry and Microcopy

After PFA fixation, cells on coverslips are permeabilized with TBS-Triton-X100 (0.1%), blocked with 1% bovine serum albumin and incubated with mouse vinculin primary antibody (Table 16). Vinculin immunolabelling is visualized using a secondary anti-mouse fluorescent antibody (Table 16). Actin cytoskeleton is visualized by staining with fluorescent phalloidin (Table 16), a compound that specifically binds F-actin filaments. Epifluorescence microscopy is used to acquire images of Immuno- and phalloidin fluorescence, respectively.

TABLE 16

| Antibody/Dye | Dilution |
| --- | --- |
| Vinculin mouse mAb IgG (Becton Dickinson) | 1:400 |
| Alexa 488 conjugated goat anti-mouse pAB (Becton Dickinson) | 1:500 |
| Alexa 568 conjugated Phalloidin (Thermo Fisher) | 1:100 |

The results shown in FIGS. 18A and 18B demonstrate that LPA stimulation induces pronounced actin stress fiber formation in HUVECs (FIG. 18B) compared to cells prior to stimulation (FIG. 18A).

Figure 19B:
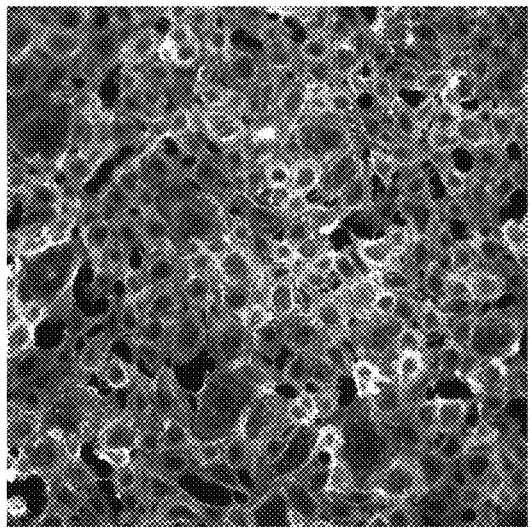
FIG. 19B is a representation of a photomicrograph of endothelial cells treated with LPA to induce Rho activation, then treated with Fasudil, and then stained with phalloidin to show stress fibers.
Figure 19D:
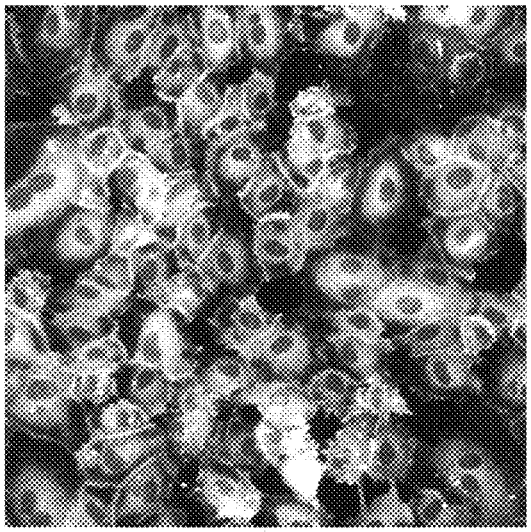
FIG. 19D is a representation of a photomicrograph of endothelial cells treated with LPA to induce Rho activation, then treated with Fasudil, and then stained with vinculin to show junctional complexes.
Figure 19A:
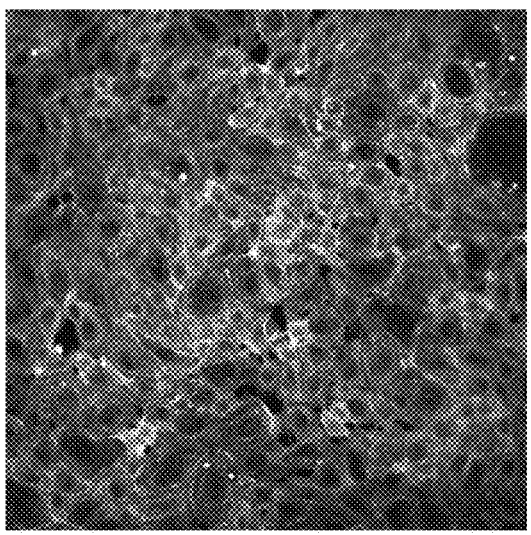
FIG. 19A is a representation of a photomicrograph of endothelial cells treated with LPA to induce Rho activation, then treated with BA-1049 (R), and then stained with phalloidin to show stress fibers.
Figure 19C:
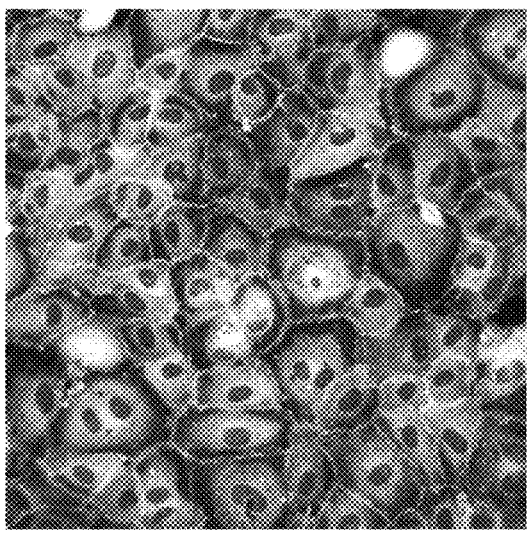
FIG. 19C is a representation of a photomicrograph of endothelial cells treated with LPA to induce Rho activation, then treated with BA-1049 (R), and then stained with vinculin to show junctional complexes.

As shown in FIGS. 19A-19D, treatment with either BA-1049 (R) (FIGS. 19A and 19C) or Fasudil (FIGS. 19B and 19D) prevents such formation of stress fiber. In addition, the reduction in actin stress fibers is more pronounced in HUVECs treated with BA-1049 (R) (FIG. 19A) compared to Fasudil-treated cells (FIG. 19B). In addition, vinculin immunofluorescence reveals that BA-1049 (R) (FIG. 19C) is superior in preserving the integrity of the HUVEC monolayer upon LPA stimulation in comparison to Fasudil (FIG. 19D). While BA-1049 (R) treated cells show a thin, peripheral band of vinculin immunofluorescence (FIG. 19C), characteristic for a confluent cellular monolayer, Fasudil treated cells show an upregulation of vinculin-positive focal adhesion complexes associated with a decreased cell confluency (FIG. 19D).

Example 12

BA-1049 (R) Metabolites Generated in Cultured Hepatocytes

To investigate the metabolism of BA-1049 (R) in different mammalian species an in vitro system was used. BA-1049 (R) was added to cultures of rat, human, mouse, cynomolgus monkey, and canine hepatocytes to investigate metabolism in different species.

A stock solution of BA-1049 was first diluted in acetonitrile at a concentration 100× of the desired final concentration. Test articles were incubated in duplicate rat hepatocytes at 37° C. The reaction contained 106 viable hepatocytes/ml KHB buffer, a pH 7.4. At indicated times (0 min, 15 min, 30 min, 60 min, 120 min), an aliquot was removed from each experimental and control reaction and mixed with an equal volume of ice-cold methanol. Stopped reactions were incubated at least ten minutes at −20° C. The samples were centrifuged to remove precipitated protein, and the supernatants were analyzed by LC-MS/MS.

Figure 20:
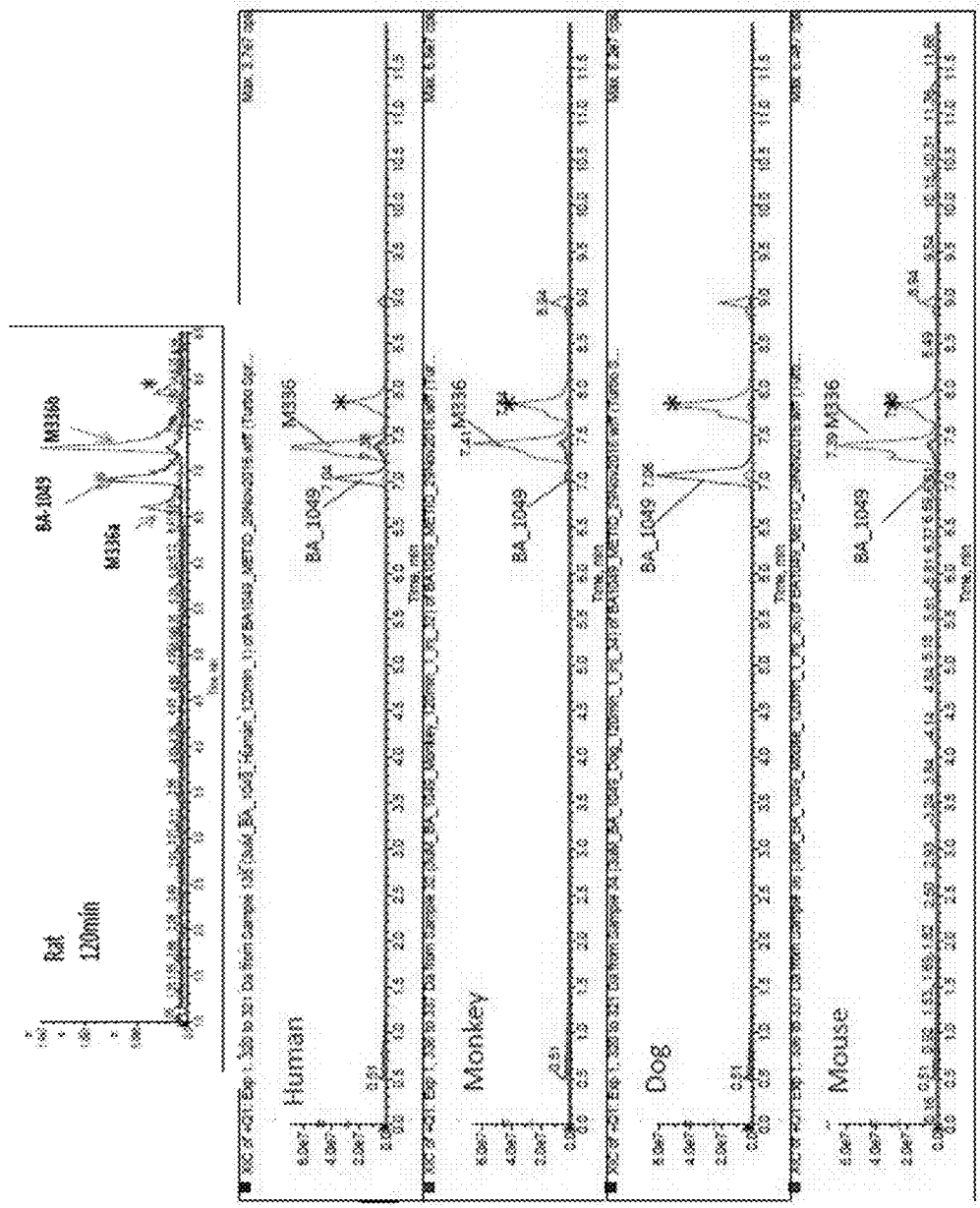
FIG. 20 are representations of chromatographic profiles of BA-1049 (R) and its metabolites generated by treatment of hepatocytes from rat, human, monkey, dog, and mouse, demonstrating that dog does not produce any metabolite and rat produces a minor metabolite, (M336a) not seen in other species, whereas the peak at 7.4 minutes represents 1-hydroxy-BA-1049 (R), and all peaks eluting later than 7.6 minutes are background peaks.

The results in FIG. 20 show that the half-life of BA-1049 (R) is different in different species and that dog hepatocytes appear to not metabolize the compound. Table 17 further indicates that rat and monkey are good species to model drug metabolism in preparation for human studies owing to their more nearly similar rates of metabolism.

In parallel, blank hepatocytes in the absence of test agent were incubated for 120 min. This blank hepatocyte incubation was used as a control to show the presence of peaks derived from the hepatocytes themselves. A negative control was run by incubating hepatocytes in the absence of test article, then adding test article to the quenched assay (T=0 min). This negative control was included to show the presence of any impurities in the test article.

A full scan mass spectrum (100 mg-800 m/z) in both positive and negative ionization mode was run across the gradient to look for the presence of metabolites. Scans from the blank hepatocytes and negative control (T=0 min) were compared with the incubated samples (T=120 min). A peak was deemed a potential metabolite when it was present in both duplicates of the test sample at a level at least 5-fold higher than either negative control sample. Product ion scans of observed peaks were performed to confirm if these observed peaks are indeed parent-related.

TABLE 17

| Species | ½ Life (min) |
|---------|--------------|
| Human | 41.7 |
| Monkey | 15.3 |
| Dog | >480 |
| Mouse | 2.2 |
| Rat | 60 |

Table 17 shows the half-life at BA-1049 (R) in different species. The results in FIG. 20 and Table 17 show that BA-1049 (R) added to cultured hepatocytes from multiple species is readily metabolized to 1-hydroxy-BA-1049 (R) in human, rat, mouse, and monkey hepatocytes, while rat hepatocytes also generate N-oxide-BA-1049 (R). The structure of N-oxide-BA-1049 (R) is shown represented in FIG. 21C. Dog hepatocytes do not show any detectable metabolism of BA-1049 (R), indicating they may be a poor species choice for studies of the drug prior to testing in human.

Example 13

Penetration of BA-1049 (R) and
1-Hydroxy-BA-1049 (R) in

Mouse and Rat Brain and in Vascular Tissue

The following experiment demonstrates the penetration of BA-1049 (R) and its metabolite, 1-hydroxy-BA-1049 (R), in rat and mouse brains via intravenous (IV) administration.

Mouse brains are dissected out at specific time points after IV BA-1049 (R) administration, and the concentration of BA-1049 (R) and 1-hydroxy-BA-1049 (R) in homogenized brain tissue determined using LC-MS/MS analysis. In rats, brains and blood vessels are dissected out at specific time points after IV BA-1049 (R) administration.

The results of the experiment demonstrate that BA-1049 (R) and 1-hydroxy-BA-1049 (R) penetrate brain tissue to treat or manage diseases, disorders, or injuries.

A. Animals and Dosing

Adult male C57BL/6 mice (Charles River Laboratories) are used in this study. Mice are dosed either by intravenous (IV) administration or oral (PO) administration via oral gavage. Mice dosed by IV receive a single 5 mg/kg BA-1049 (R) dose formulated in phosphate buffered saline (PBS). An additional cohort of mice receives a single 30 mg/kg BA-1049 (R) oral dose formulated in PBS.

Mice are monitored after administration for clinical signs of adverse effects of the administered compound.

Adult male, Sprague-Dawley rats (Charles River Laboratories) are used in this study. Rats are dosed by a single intravenous (IV) 2.5 mg/kg BA-1049 (R) dose via tail vein injection. Both doses are formulated in phosphate buffered saline (PBS).

Rats are monitored after administration for clinical signs of adverse effects of the administered compound.

B. Sample Collection and Analysis

After IV dosing, brains are collected from 4 mice at each time point: 0.083 hr, 0.5 hr, 2 hr, 6 hr, 12 hr, and 24 hr after dose. Each mouse is euthanized by $CO_2$. The entire brains are removed, weighed, rinsed with PBS, placed in tubes, and snap frozen in liquid nitrogen.

After IV dosing, brains are collected from 3 rats at each time point: 0.25 hr, 0.5 hr, and 1 hr after dose. Brain samples are weighed, placed in a tube and frozen on dry ice. Brains are the stored at −80° C. until analysis.

A portion of the inferior vena cava is dissected out, weighed, and placed in a tube on dry ice. This vascular tissue is stored at −80° C. until analysis.

Mouse brain samples are analyzed for determination of the plasma concentration of BA-1049 (R) and its metabolite 1-hydroxy-BA-1049 (R). Brain tissue was homogenized in 1 mL/g PBS. Brain homogenates are precipitated by pipetting 200 µL of homogenate into a tube using aseptically cut off 1000 µL pipette tips to prevent clogging. Samples are further diluted with 100 µL PBS to aid in precipitation. 900 µL of cold methanol is added to each sample and samples are vortexed for 5 sec to 10 sec. Samples are placed at 4° C. for 30 min to 40 min and then centrifuged at 10,000 RPM for 15 min at 4° C. The supernatant is collected and stored at −80° C. until analyzed.

These samples are injected into an LC-MS/MS (liquid chromatography-tandem mass spectrometry) system for detection of BA-1049 (R) and 1-hydroxy-BA-1049 (R).

Rat brain samples are analyzed for determination of the plasma concentration of BA-1049 (R) and its metabolite 1-hydroxy-BA-1049 (R). Brain tissue is homogenized in 1 mL/g PBS. Brain homogenates are precipitated by pipetting 200 µL of homogenate into a tube using aseptically cut-off 1000 µL pipette tips to prevent clogging. Samples are further diluted with 100 µL PBS to aid in precipitation. 900 µL of cold methanol is added to each sample and samples are vortexed for 5-10 seconds. Samples are placed at 4° C. for 30 min to 40 min, and then centrifuged at 10,000 RPM for 15 min at 4° C. The supernatant was collected and stored at −80° C. until analyzed.

Inferior vena cava were homogenized by adding 2 mL/g PBS and mashed with a biomasher pestle (Kimble). Precipitation was performed by adding 3 mL/mL cold methanol. Samples were vortexed for 5 sec to 10 sec. Samples were placed at 4° C. for 60 min, then centrifuged at 10,000 RPM for 15 min at 4° C. The supernatant was collected and stored at −80° C. until analyzed.

These samples were injected into an LC-MS/MS (liquid chromatography-tandem mass spectrometry) system for detection of BA-1049 (R) and 1-hydroxy-BA-1049 (R).

Concentrations of BA-1049 (R) and 1-hydroxy-BA-1049 (R) in each sample were adjusted for dilution and tissue weight to calculate the amount of each compound per gram of brain tissue. These values were reported, averaged, and plotted against time to determine the time course of the appearance and disappearance of BA-1049 (R) and metabolite.

C. Results

BA-1049 (R) and its primary, active metabolite 1-hydroxy-BA-1049 (R) were detectable in rat and mouse brains after IV administration (FIGS. 22A and B). In mouse, BA-1049 (R) remained detectable at least 24 hr after administration, while 1-hydroxy-BA-1049 (R) was undetectable by 12 hr. In rat brains, like in mice, there was more BA-1049 (R) than 1-hydroxy-BA-1049 (R) at 30 min post-administration. There was a large amount of both compounds in vascular tissue of rats 30 min after IV administration, with more 1-hydroxy-BA-1049 (R) than BA-1049 (R).

These results demonstrate that BA-1049 (R) and its metabolite 1-hydroxy-BA-1049 (R) are present and detectable in blood, brain and vascular tissue after IV administration. By weight, vascular tissue, such as the inferior vena cava, contains even more of both compounds than brain tissue. Additionally, intravenous administration provides pharmacologically active compound into brain and vascular tissue to treat or manage diseases, disorders, or injuries.

Example 14

Activity of BA-1049 (R) Metabolites

To determine if the metabolites of BA-1049 (R), 1-hydroxy-BA-1049 (R) and the N-oxide-BA-1049 (R), show inhibitory activity for ROCK2, inhibition curves are determined for each compound compared to the parent compound BA-1049 (R).

Each compound was dissolved at 100 mM in DMSO. This compound-DMSO solution is diluted to 500 µM in $dH_2O$. Serial dilutions were prepared so that a semi-log range of compound is present after being diluted 5× in other assay reagents, from 100 µM through 1 nM.

10 µL of each concentration of each compound was added in duplicate to individual wells of a 96-well Maxisorp plate (ThermoFisher) pre-coated with the ROCK2 substrate MYPT1 (ThermoFisher). $dH_2O$ is added as a negative control.

Using a multichannel pipettor, 40 µL of final volume per well was made by the addition of the following of each solution to begin the reaction: 10 µL 20 mM MOPS pH 7.2, 25 mM β-glycerophosphate, 5 mM EGTA, 1 mM $Na_3VO_4$, and 1 mM DTT, 10 µL 50 µM ATP, 10 µL 75 mM $MgCl_2$, and 10 µL 1 mU/µL ROCK2 solution. The solutions were mixed by agitation and incubated on shaker for 10 min at 30 C°.

The reaction was stopped by emptying plate and washing 3 times for 3 min each with 200 µL Washing Buffer (Tris-buffered saline and 0.05% Tween-20).

100 µL 0.5 µg/mL of an anti-phosphorylated MYPT1 (Thr696) antibody (EMD, Billerica, Mass., Cat. No. CS205309) solution was added to each well. The plate was incubated at RT on shaker for 1 hr and then washed 3 times for 3 min with 200 µL washing buffer.

100 µL goat anti-rabbit IgG horseradish peroxidase-conjugated secondary antibody (EMD; Billerica, Mass.; Cat. No. 90276, 1:2000 dilution) was added to each well. The plate was incubated at RT on a shaker for 1 hr and then washed 3 times for 3 min with 200 µL Washing Buffer. The plate was washed 2 additional times for 3 min each with Tris-buffered saline.

100 µL TMB/E solution was added to each well with a multichannel pipette. Upon sufficient color development, the reaction was stopped using 100 µL stop solution and absorbance read using a Wallac Victor2 plate reader at 450 nm.

Because absorbance values proportional to ROCK2 activity, plotting absorbance at 450 nm versus final concentration of metabolite and parent compound provides inhibition curves. Relative inhibitory profiles were determined through 4PL analysis of these curves. Variations in calculated $IC_{50}$ are common before assay optimization due to variations in experimental variables.

Figure 23:
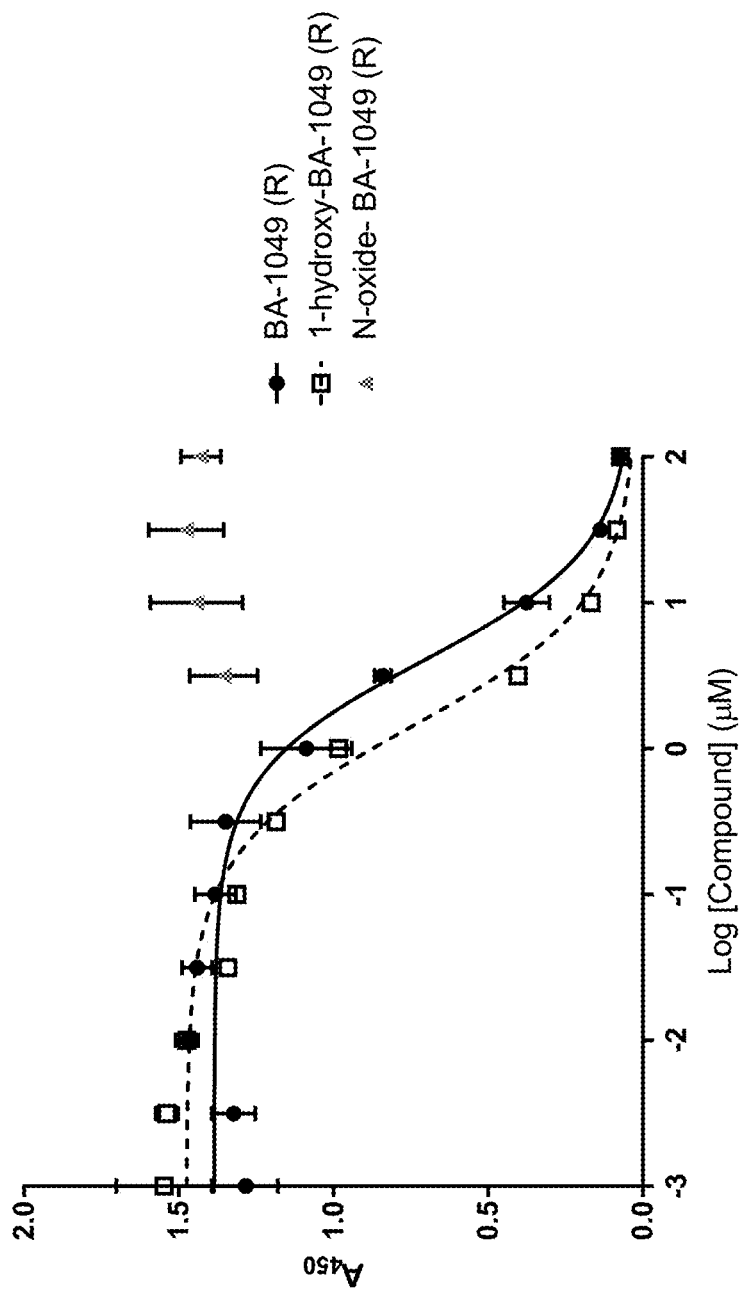
FIG. 23 is a graphic representation of relative inhibition curves of purified ROCK2 by BA-1049 (R) and two metabolites 1-hydroxy-BA-1049 (R) and N-oxide BA-1049 (R).

The results in FIG. 23 show that 1-hydroxy-BA-1049 (R) is a ½ log more potent as an inhibitor of ROCK2 activity than the parent BA-1049 (R) compound. The N-oxide-BA-1049 (R) does not exhibit any inhibitory activity.

Example 15

In Vitro Effect of BA-1049 (R), BA-1049 (S), and Metabolites Thereof on Human Umbilical Vein Endothelial Cells after Rho/Rock Activation The activities of BA-1049 (R), BA-1049 (S) and metabolites of BA-1049 (R) were investigated using cultured human vascular endothelial cells.

1. Cell Culture

Primary HUVECs (ATCC, Manassas, Va.) were grown on collagen-1 (50 µg/mL) coated 75 $cm^2$ tissue culture flasks using Medium-200 supplemented with large vessel endothelium growth supplement (both ThermoFisher, Waltham, Mass.). After reaching 80% confluency, cells were extracted using 0.25% trypsin-EDTA (ThermoFisher, Waltham, Mass.) and plated on tissue culture substrate as described below.

2. Dosing and Analysis Timing

Five individual doses (1 µM, 10 µM, 25 µM, 50 µM, and 100 µM) of BA-1049 (R), 1-Hydroxy-BA-1049 (R), N-Oxide-BA-1049(R) and of BA-1049 (S) were evaluated for the ability to restore normal Rho/ROCK activity in LPA-treated HUVECs. Cell lines were exposed to each dose for 1 hr, and then are stimulated with 20 µM LPA for either 5 min or 1 hr as described below. All experiments were conducted in triplicate and analyzed by two independent assessors blinded to both cell line and treatment.

a. Phosphorylation of ROCK2 Downstream Targets Myosin Light Chain 2 (MLC2) and Cofilin Cells were subjected to biochemical analysis of diphosphorylated MLC2 (Threonine 18/Serine 19 phosphorylation sites) and cofilin (Serine 9 phosphorylation site) using SDS-PAGE and immunoblotting. Cells were plated in 24-well tissue culture plates coated with 70 µg/ml rat collagen-1 (Corning; Corning, N.Y.), and grown for 2 d to 3 d at 37° C./5% $CO_2$ until confluency. Cells were pretreated with 5 individual doses (1 µM, 10 µM, 25 µM, 50 µM, and 100 µM) of BA-1049 (R), 1-Hydroxy-BA-1049 (R), N-Oxide-BA-1049 (R) and of BA-1049 (S) diluted in Medium 200 (ThermoFisher) supplemented with 0.1% human serum albumin (HSA, Sigma-Aldrich, St. Louis, Mo.) for 1 hr. Then medium was exchanged for Medium 200 supplemented with 0.1% HSA (Sigma-Aldrich) and 20 µM of LPA (Santa Cruz Biotech; Santa Cruz, Calif.) and incubated for 5 min. After LPA stimulation, proteins were extracted from cells by lysis with RIPA buffer supplemented with HALT complete protease/phosphatase inhibitor (ThermoFisher, Waltham, Mass.), reduced and denatured using Laemmli sample buffer (BioRad, Hercules, Calif.)/beta-mercaptoethanol and subjected to SDS-PAGE.

Denatured samples were electrophoresed in reducing 10% Bis-Tris-gels polyacrylamide gels (Novex; Thermo-Fisher, Waltham, Mass.) and were transferred onto 0.25 µm PVDF membranes (EMD Millipore, Billerica, Mass.). Membranes are probed using amti-pMLC2 T18/S19 (1:500; Cell Signaling, Danvers, Mass.) or anti-pCofilin S9 (1:500, Cell Signaling, Danvers, Mass.) and anti-glyceraldehyde 3-phosphate dehydrogenase loading control (GAPDH, 1:10000; Abcam). Protein levels were detected using chemiluminescence substrate (Super Signal West, ThermoFisher, Waltham, Mass.) and images captured using a FluoroChem SP Imaging System.

b. Endothelial Monolayer Integrity

To examine HUVEC monolayer integrity, cells were plated on PDL-coated coverslips (Corning) coated with fibronectin, collagen-1 and gelatin. 50,000 cells were seeded on each coverslip situated in a 24-well plate. Cells were grown for 3 days at 37° C./5% $CO_2$. Different cell samples were pretreated with five different doses (1 µM, 10 µM, 25 µM, 50 µM, and 100 µM) of BA-1049 (R), 1-Hydroxy-BA-1049 (R), N-oxide-BA-1049 (R) or BA-1076 (S) diluted in Medium 200 (ThermoFisher, Waltham, Mass.) supplemented with 0.1% human serum albumin (HSA, Sigma) for 1 hr. The medium was exchanged by Medium 200 supplemented with 0.1% HSA and 20 µM of LPA (Santa Cruz) and incubated for 60 min.

After LPA stimulation, cells were fixed with 4% paraformaldehyde and stained for actin-phalloidin (ThermoFisher, Waltham, Mass.) and V-Cadherin (Cell Signaling, Danvers, Mass.) and mounted on microscope slides. Coverslips were imaged by fluorescence microscopy and the cell free holes in the monolayer are measured using Image J (freeware; https://imagej.nih.gov/ij/).

3. Results

Figure 24:
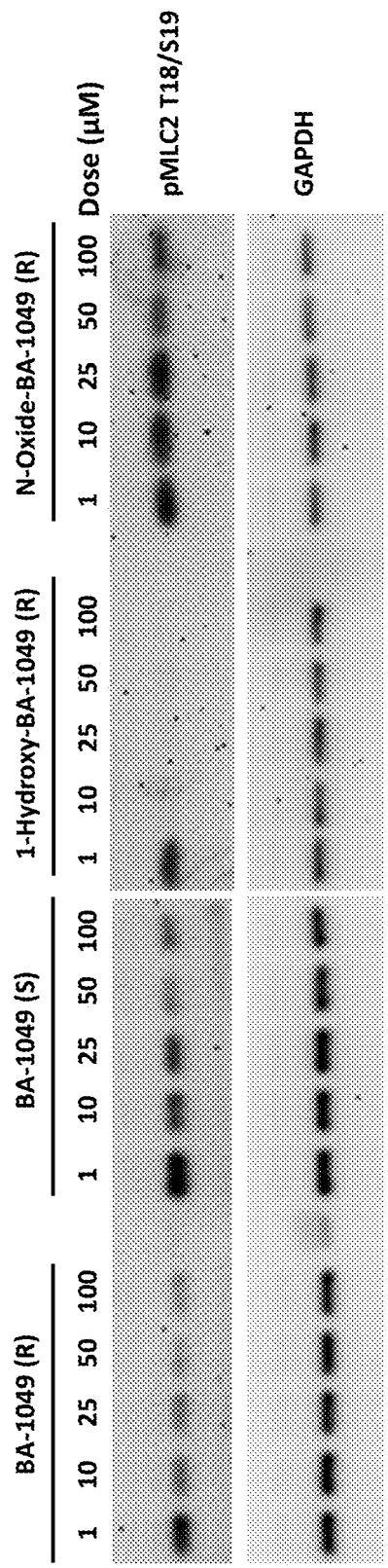
FIG. 24 are representations of immunoblots of pMLC2 T18/S19 compared with loading control GAPDH when human umbilical vein endothelial cells were treated with purified stereoisomers of BA-1049 (R) and BA-1049 (S) and the two metabolites of BA-1049 (R), 1-hydroxy-BA-1049 (R) and N-oxide BA-1049 (R)

In LPA-treated HUVECs, BA-1049 (R), BA-1049 (S) and 1-hydroxy-BA-1049 (R) reduce MLC2 diphosphorylation, while N-Oxide-BA-1049 (R) did not show such an effect (FIG. 24). BA-1049 (R) shows a higher potency in reducing pMLC2 T18/S19 than BA-1049 (S) (FIG. 24). 1-hydroxy-BA-1049 (R) shows the highest potency of all tested compounds, fully abolishing MLC2 diphosphorylation at a concentration of 10 µM or higher (FIG. 24). HUVECs treated with LPA to stimulate ROCK activation show increased stress fibers and changes in cell-cell junctions, which results in cell free holes in the monolayer (FIG. 25D), as compared to controls (FIG. 25A). Cells treated with LPA and 1 µM BA-1049 (R) (FIG. 25B) or 10 µM of BA-1049 (R) (FIG. 25C) resemble control cultures with normal monolayer appearance. When cells are treated with LPA plus 1 µM BA-1049 (S) (FIG. 25E) or 10 µM BA-1049 (S) (FIG. 25F), neither concentration reverses the effect of LPA. Thus, BA-1049 (R) and 1-hydroxy-BA-1049 (R), but not BA-1049 (S) nor N-Oxide-BA-1049 (R), prevents Rho/ROCK activation and restores monolayer integrity in human umbilical vein endothelial cells (HUVEC) after exposure to lysophosphatidic acid (LPA).

Example 16

In Vitro Effect of BA-1049 (R), BA-1049 (R), 1-Hydroxy-BA-1049, and BA-1076 Rho/Rock Activation (S) on Brain Microvascular Endothelial Cells After Rho/Rock Activation The activities of BA-1049 (R), BA-1049 (S), and metabolites of BA-1049 (R) are investigated using primary human brain microvascular endothelial cells.

1. Cell Culture

Primary hBMVECs (Neuromics, Edina, Minn.) are grown on collagen-1 (70 µg/mL, Corning) coated 75 $cm^2$ tissue culture flasks using ENDO-growth media (ENDO-Basal media+ENDO-growth supplement, both Neuromics, Edina, Minn.). After reaching 90% confluency, cells are extracted using 0.25% trypsin-EDTA and plated on tissue culture substrate as described below.

2. Dosing and Analysis Timing

Five individual doses of BA-1049 (R), 1-Hydroxy-BA-1049 (R), N-Oxide-BA-1049(R) and of BA-1049 (S) are evaluated for the ability to restore normal Rho/ROCK activity in LPA-treated hBMVEC. Cells are exposed to each dose for 1 hr, and are then stimulated with 20 µM LPA for either 5 min or 1 hr as described below. All experiments are conducted in triplicate and analyzed by 2 independent assessors blinded to both cell line and treatment.

a. Phosphorylation of ROCK2 Downstream Targets Myosin Light Chain 2 (MLC2) and Cofilin Cells are subjected to biochemical analysis of diphosphorylated MLC2 (Threonine 18/Serine 19 phosphorylation sites) and phosphorylated cofilin (Serine 9 phosphorylation site) using SDS-PAGE and immunoblotting. Cells are plated in 24-well tissue culture plates coated with 70 µg/ml rat collagen-1 (Corning) and grown in ENDO-growth media (Neuromics) for 3 days at 37° C./5% $CO_2$ until confluency. Cells are pretreated with 5 individual doses (1 µM, 10 µM, 25 µM, 50 µM, 100 µM) of BA-1049 (R), 1-Hydroxy-BA-1049 (R), N-Oxide-BA-1049 (R) and of BA-1049 (S) diluted in ENDO Basal media (Neuromics) supplemented with 0.1% human serum albumin (HSA, Sigma-Aldrich) for 1 hr. The medium is exchanged for ENDO basal media supplemented with 1% HSA, 20 µM of LPA (Santa Cruz Biotech; Santa Cruz, Calif.) and the appropriate amount of compound being tested. After 5 min, the medium is aspirated and the cells are briefly washed with 1×PBS. Proteins are extracted from cells by lysis with RIPA buffer supplemented with complete protease/phosphatase inhibitor (HALT, Thermo Fisher Scientific), reduced and denatured using Laemmli sample buffer (BioRad; Hercules, Calif., beta-mercaptoethanol and subjected to SDS-PAGE.

Denatured samples are electrophoresed in reducing 10% Bis-Tris-PA gels (Novex; Thermo-Fisher), and are transferred onto 0.25 µm PVDF membranes (EMD Millipore). Membranes are probed using amti-pMLC2 T18/S19 (1:500; Cell Signaling) or anti-pCofilin (1:500, Cell Signaling S9) and anti-glyceraldehyde 3-phosphate dehydrogenase loading control (GAPDH, 1:10000; Abcam, Cambridge, Mass.). Protein levels are detected using a chemiluminescence substrate (Super Signal West, ThermoFisher) and images are captured using a FluoroChem SP Imaging System.

b. Endothelial Monolayer Integrity

To examine hBMVECs monolayer integrity, cells are plated on PDL-coated coverslips (Corning) coated with Fibronectin, Collagen-1 and gelatin. 50,000 cells are seeded on each coverslip situated in a 24-well plate. Cells are grown for 3 days in ENDO-growth media (Neuromics) at 37° C./5% $CO_2$. Different cell samples are pretreated with five different doses of BA-1049 (R), 1-Hydroxy-BA-1049 (R), N-Oxide-BA-1049 (R) or BA-1076 (S) diluted in ENDO-basal media (Neuromics) supplemented with 0.1% human serum albumin (HSA, Sigma-Aldrich) for 1 hr. The medium is exchanged for ENDO basal media supplemented with 1% HSA, 20 µM of LPA (Santa Cruz Biotech; Santa Cruz, Calif.) and the appropriate amount of compound being tested. After 60 min, cells were fixed with 4% paraformaldehyde and stained for actin-phalloidin (ThermoFisher) and V-Cadherin (Cell Signaling), and then were mounted on microscope slides. Coverslips were imaged by fluorescence microscopy and the cell-free holes in the monolayer are measured using Image J.

3. Results

In LPA-treated hBMVECs, BA-1049 (R), BA-1049 (S) and 1-hydroxy-BA-1049 (R) reduce MLC2 diphosphorylation, while N-Oxide-BA-1049 (R) do not show such an effect. BA-1049 (R) shows a higher potency in reducing pMLC2 T18/S19 than BA-1049 (S). 1-hydroxy-BA-1049 (R) shows the highest potency of all tested compounds, fully abolishing MLC2 diphosphorylation at a concentration of 10

μM or higher. hBMVECs treated with LPA to stimulate ROCK activation show increased stress fibers and changes in cell-cell junctions, resulting in cell-free holes in the monolayer, as compared to controls. Cells treated with LPA and 1 μM BA-1049 (R) or 10 μM of BA-1049 (R) resemble control cultures with normal monolayer appearance. When cells are treated with LPA plus 1 μM BA-1049 (S) or 10 μM BA-1049 (S), neither concentration reverses the effect of LPA.

BA-1049 (R) but not BA-1049 (S) is able to reverse the cellular changes induced by LPA stimulation of ROCK activation in endothelial cells.

Thus, of BA-1049 (R) and 1-Hydroxy-BA-1049 (R), but not BA-1049 (S) or N-oxide-BA-1049 (R), prevent Rho/ROCK activation and to protect tight junction preservation in human brain microvascular endothelial cells (hBMVECs) after exposure to lysophosphatidic acid (LPA).

Example 17

Efficacy and Potency of BA-1049 (R) and 1-Hydroxy-BA-1049 (R) in Human Endothelial Cells 1-hydroxy-BA-1049 (R) was tested to determine its efficacy in primary human endothelial cells. The $EC_{50}$ for BA-1049 (R) and for 1-hydroxy-BA-1049 (R) in cultured human endothelial cells (HUVECs) was also investigated to compare potency of both compounds and to provide information about required exposure in vivo.

1. Cell Culture

Primary human umbilical vein endothelial cells (HUVECs; ATCC) were grown on plastic tissue culture flasks using Medium-200 supplemented with large vessel endothelium growth supplement (Thermo Fisher Scientific). After reaching 80% confluency, cells were extracted using 0.25% trypsin-EDTA and plated in 24-well tissue culture plates (Falcon) as described below.

2. Dosing and Analysis Timing

Eight different doses of BA-1049 (R) or 1-hydroxy-BA-1049 (R) (0 nM, 10 nM, 100 nM, 1 μM, 10 μM, 50 μM, 100 μM, and 1 mM) were evaluated for their effects on intracellular ROCK activity. Cells were exposed to each dose for 1 h. All experiments were conducted in triplicate and analyzed by 2 independent assessors blinded to the compound and compound concentration.

a. Phosphorylation of ROCK2 Downstream Target Myosin Light Chain 2 (MLC2)

Cells were subjected to biochemical protein analysis of di-phosphorylated MLC2 (Threonine 18/Serine 19 phosphorylation sites) using SDS-PAGE and immunoblotting. Cells were plated in a 24-well tissue culture plates, coated with 70 μg/ml rat collagen-1 (Corning) and grown for 2-3 days at 37° C./5% $CO_2$ until confluency. Cells were pretreated with different doses of BA-1049 (R) or 1-hydroxy-BA-1049 (R) for 1 hr. Drugs were diluted in Medium 200 (Thermo Fisher Scientific) supplemented with 0.1% human serum albumin (HSA, Sigma-Aldrich). After 1 h, cells were lysed with RIPA buffer (Boston Bioproducts; Ashland, Mass.) supplemented with complete protease/phosphatase inhibitors (HALT, Thermo Fisher Scientific), reduced, and denatured with Laemmli sample buffer (BioRad)/beta-mercaptoethanol. Denatured samples were electrophoresed in reducing 10% Bis-Tris-PA gels (Novex) and then transferred onto 0.25 μm PVDF membranes (EMD Millipore). Membranes were incubated with 4% bovine serum albumin solution to block unspecific antibody binding sites and then immunolabeled for ppMLC2 T18/S19 (1:500, Cell Signaling) and glyceraldehyde 3-phosphate dehydrogenase loading control (GAPDH, 1:10,000; Abcam). Protein levels were detected using a chemiluminescence substrate (Super Signal West, ThermoFisher) and were captured with FluoroChem SP imaging system. Chemiluminescence of ppMLC2 and GAPDH was measured by densitometric analysis. ppMLC2 signal was normalized against GAPDH signal plotted as percentage of no treatment control (0 μM). $EC_{50}$ values were determined by dose-response analysis using GraphPad software.

3. Results

Figure 26A:
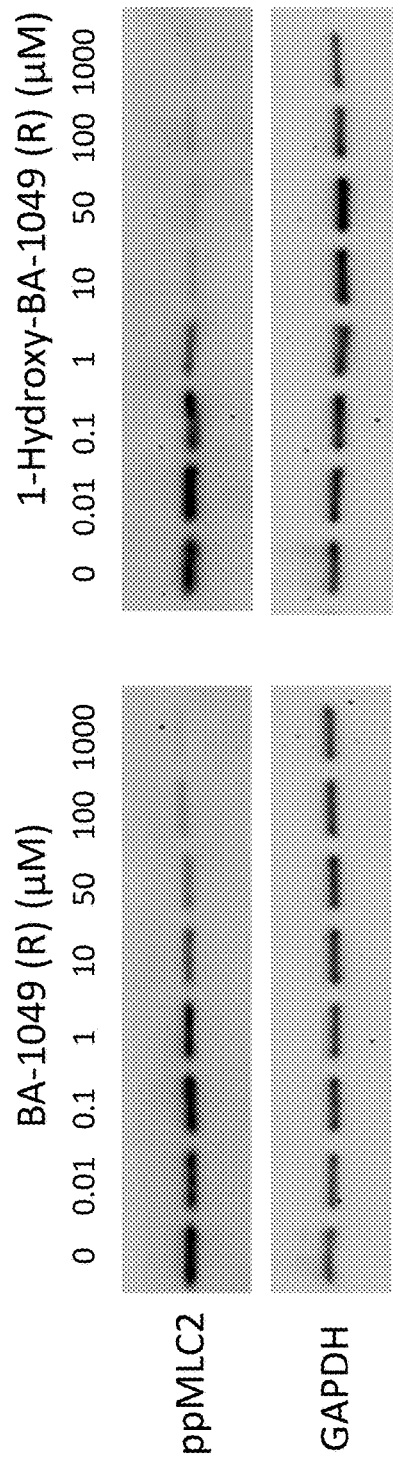
FIG. 26A are representations of immunoblots of pMLC2 T18/S19 compared with loading control GAPDH when human umbilical vein endothelial cells were treated with BA-1049 (R) or 1-hydroxy-BA-1049 (R)
Figure 26B:
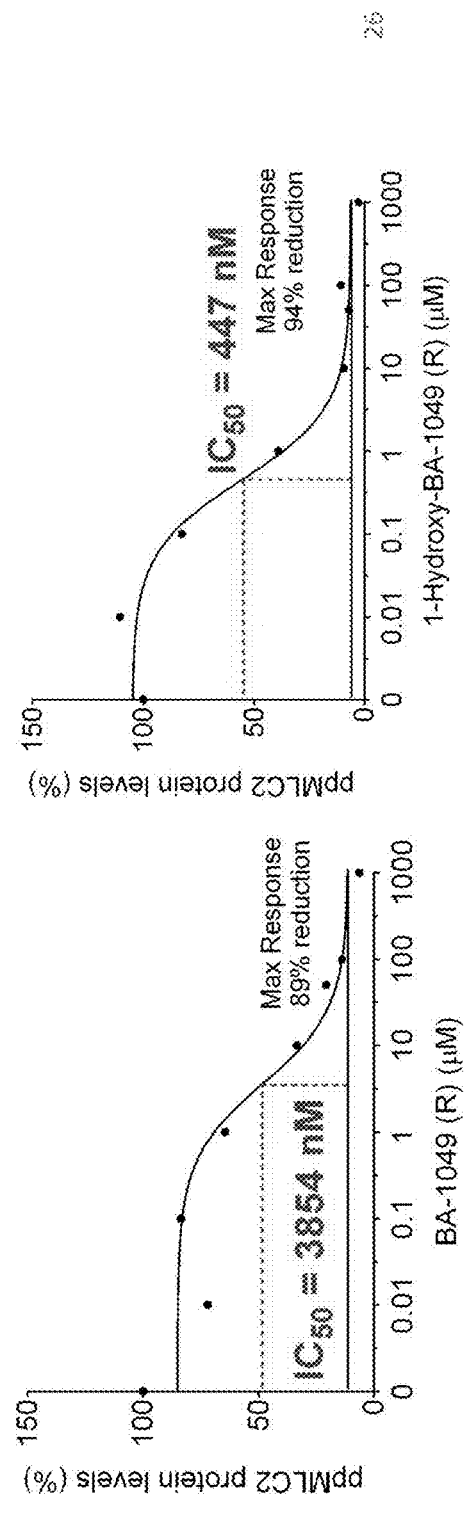
FIG. 26B are graphical representations of the densitometric measurements of the immunoblots (shown in FIG. 25A) resulting from treatment with BA-1049 (R) or 1-hydroxy-BA-1049 (R), where densitometric values of pMLC2 are normalized and plotted as % of untreated control, and where the inhibitory concentration ($IC_{50}$) is calculated.

As shown in FIGS. 26A and 26B dose-response analysis show that both, BA-1049 (R) and 1-hydroxy-BA-1049 (R) reduced MLC2 diphosphorylation in a dose-dependent fashion (FIG. 26A). Both drugs showed a similar efficacy with a maximum reduction of ppMLC2 levels of 89% for BA-1049 (R) and 94% for 1-hydroxy-BA-1049 (R) at the highest dose tested (=1 mM). However, 1-hydroxy-BA-1049 showed a one log higher potency than BA-1049 (R), indicated by an $EC_{50}$ value of 449.1 nM for 1-hydroxy-BA-1049 (R) compared to an $EC_{50}$ value of 3830 nM for BA-1049 (R) (FIG. 26B).

These results suggest that 1-hydroxy-BA-1049 (R) is cell-permeable and biological active and that 1-hydroxy-BA-1049 (R) has similar efficacy but higher potency in inhibiting ROCK in HUVECs than its parent BA-1049 (R).

Example 18

Effects of BA-1049 (R) and BA-1049 (S) on Systolic Blood Pressure Values in Mice The following experiment demonstrates the difference in effect of BA-1049 (R) and BA-1049 (S) on lowering systolic blood pressure in mice. Rho kinase plays an important role in regulating vascular tone, but blood pressure depends more on peripheral blood vessels, where ROCK1 expression is greater than ROCK2. Mice are exposed to increasing doses of either BA-1049 (R) or BA-1049 (S), delivered via their drinking water and their blood pressure is monitored. The lower selectivity of BA-1049 (S) for ROCK2 causes a lowering of systolic blood pressure at a dose significantly lower than BA-1049 (R), which shows greater selectivity for ROCK2.

Three test cohorts of mice are housed with unlimited access to normal chow and drinking water. For the first 5 days, the mice are handled daily to habituate them to contact and their blood pressures measured using a multi-animal tail cuff plethysmography apparatus (MRBP Tail Cuff Blood Pressure System; IITC Life Science; Woodland Hills, Calif.). Systolic blood pressure for each mouse is recorded multiple times over a 5 min. session on days 2 and 5. These values serve as the baseline.

On day 5, one cohort of mice is switched to drinking water containing BA-1049 (R) at 0.5 mg/kg-body weight. A second cohort receive water containing BA-1049 (S) at 0.5 mg/kg-body weight. The third cohort receives normal, unadulterated drinking water. On day 8, blood pressure is measured for all mice.

After the day 8 blood pressure measurement, drug dosage in the 2 test cohorts is increased to 1 mg/kg-body weight and the cohort continues for 3 days at the new dose. On day 11, blood pressure is again recorded by tail cuff plethysmography for all mice during a 5 min. recording session.

Following the blood pressure recording, ON DAY 11, drug dosages in drinking water of test groups are increased up to 3 mg/kg-body weight and the cohorts continue for 3 days at the new dose. On day 14, blood pressure is recorded by tail cuff plethysmography for all mice during a 5 min. recording session.

One or more of the test doses of BA-1049 (S) reduce average systolic blood pressure within a given treatment cohort. Increasing doses of BA-1049 (S)) show larger reductions in systolic blood pressure. BA-1049 (R), because of its higher selectivity for ROCK2, shows little or no effect on average systolic blood pressure.

Example 19

In Vitro Effect of BA-1049 (R) and BA-1049 (S) on Vascular Endothelial Cells Depleted of CCM Proteins The following experiment demonstrates the ability of BA-1049 (R) but not BA-1049 (S) to restore key wildtype (WT) features in vascular endothelial cells depleted of CCM proteins. These in vitro experiments are conducted in endothelial cell lines derived from CCM lesion biopsy in patients with Ccm1, Ccm2, or Ccm3 mutations, and in a human microvascular endothelial cell line (HMVEC).

1. Cell Line Preparation

HMVEC cells are depleted of each of the CCM proteins via transfection with small interfering RNA (siRNA) specific to Ccm1, Ccm2 or Ccm3 (Dharmacon, Lafayette, Colo.); the Wildtype cell line consists of untreated HMVEC cells. Patient biopsy cell lines (Wildtype, Ccm1 Mutation; Ccm2 Mutation; Ccm3 Mutation) are generated from endothelial cells obtained during biopsies of patients with specific Ccm mutations; the Wildtype cell line is derived from a biopsy sample of a subject with no Ccm mutations.

2. Dosing and Analysis Timing

Five individual doses (1 μM, 10 μM, 25 μM, 50 μM, 100 μM) of BA-1049 (R) and of BA-1049 (S) are evaluated for the ability to restore a Wildtype phenotype in each CCM HMVEC cell line and each Ccm mutant biopsy cell line. Cell lines are exposed to each dose as: (1) a repeating daily dose in culture media; (2) a 30 min. exposure and washout daily; and (3) treatment for an initial 24 hr period only.

The endpoints described below are used to assess the ability of each dose to restore a Wildtype endothelial phenotype in each cell line at each time point. Each endpoint is evaluated at 24 hr, 48 hr, 72 hr, 96 hr, 120 hr, 144 hr, and 168 hr after initial treatment. All experiments are conducted in triplicate and analyzed by two independent assessors blinded to both cell line and treatment.

a. Endothelial Cell Vasculogenesis

Cells are suspended in collagen matrices to permit an analysis of their capacity for vessel-like tube formation. The matrices are made as follows: Collagen is added to tubes containing a mixture of Medium 199 (ThermoFisher Scientific, Waltham, Mass.) and NaOH at 0° C. Cells are added to a final collagen concentration of 3.75 mg/mL, and the cell-collagen mixture is seeded out into 4.5 mm microwells. The collagen is allowed to gel and equilibrated at 37° C. in a $CO_2$ incubator. After a 3 hr incubation in serum-free culture medium (Medium 199 containing reduced-serum II supplement (Upstate Biotechnology, Lake Placid, N.Y.), bFGF (40 ng/mL), VEGF (40 ng/mL), phorbol ester (50 ng/mL), and ascorbic acid (50 μg/mL), cultures are fixed with 3% glutaraldehyde for 30 min.

Time-lapse fluorescence microscopy is conducted to collect images of cultures at 0 hr, 3 hr, 6 hr, 9 hr, 12 hr, 16 hr, 20 hr, and 24 hr after fixation. Vacuole and lumen area over time is traced and quantified using MetaMorph imaging software (Molecular Devices Corp., Sunnyvale, Calif.) (n=5 independent fields per time point), and the number of lumens per field at 24 hr is counted (n=5 independent fields).

b. Endothelial Cell Migration

Haptotactic migration is examined as follows: 20,000 cells are seeded into the upper well of a Boyden chamber (Neuro Probe, Gaithersburg, Md.) in endothelial growth medium-2 (Lonza, Walkersville, Md.) and allowed to migrate for 3 hr into a polycarbonate membrane (8 μM pores) (Sigma-Aldrich) coated on the lower surface with human fibronectin (1 μg/mL) (Biomedical Technologies, Ward Hill, Mass.).

After removal of nonmigrated cells, membranes are fixed and stained (Hema3 kit, Fisher Scientific, Waltham, Mass.), and mounted on glass slides. The number of migrated cells per high-power microscopy field is quantified (n=10 fields per condition).

c. Endothelial Cell Permeability

The permeability of endothelial cells to horseradish peroxidase is measured using a trans-well assay as follows: Trans-well inserts (48-well, 3 μM pore) (Corning Inc., Corning, N.Y.) are coated with human fibronectin and seeded with 30,000 cells per well. Horseradish peroxidase (25 μg/mL) is added to the top of the insert and allowed to permeate for 6 hr. After 6 hr, the solution from the bottom of each well is mixed with 0.1 mL guaiacol and 0.2 mL hydrogen peroxide and measured for absorbance at A490 nm (n=6 wells each).

d. Intra-Endothelial Rho Kinase Activity

Intra-endothelial ROCK activity is assessed by measuring levels of phosphorylated myosin light chain 2 (phospho-MLC2) as follows: Sub-confluent cells are collected and lysed in RIPA Lysis Buffer (Santa Cruz Biotechnology, Inc., Dallas, Tex.). Cell lysates are analyzed by SDS-PAGE (7% gel) and Western blot using an antibody specific to diphosphorylated myosin light chain 2 (Cell Signaling Technology; Danvers, Mass.) (3674). Horseradish peroxidase (HRP)-conjugated secondary antibodies are used to permit development and imaging; relative levels of phosphorylated myosin light chain 2 are quantified via a densitometric quantification of band intensity on ImageJ, according to the ImageJ User Manual instructions for Gel Analysis: http://rsb.info.nih.gov/ij/docs/menus/analyze.html#gels.

e. Intra-Endothelial Ratio of ROCK1 to ROCK2

The ratio of ROCK1 to ROCK2 within endothelial cells is assessed as follows: Sub-confluent cells are collected and lysed in RIPA Lysis Buffer (Santa Cruz Biotechnology, Inc.). Cell lysates are analyzed by SDS-PAGE (7% gel) and Western blot using anti-ROCK1 and anti-ROCK2 antibodies (611136 and 610623) (BD Biosciences, San Jose, Calif.). HRP-conjugated secondary antibodies are used to permit development and imaging; relative levels of ROCK1 and ROCK2 are quantified via a densitometric quantification of band intensity on ImageJ, according to the ImageJ User Manual instructions for Gel Analysis: http://rsb.info.nih-.gov/ij/docs/menus/analyze.html#gels.

B. Results

One or more of the tested BA-1049 doses restores endothelial cell vasculogenesis, migration, permeability, Rho kinase activity, and ROCK1:ROCK2 ratio to WT levels when administered according to a tested dosing regimen; None of the tested BA-1049 (R), 1049 (S) doses restore endothelial cell vasculogenesis, migration, permeability, Rho kinase activity, and ROCK1:ROCK2 ratio to WT levels when administered according to a tested dosing regimen.

Example 20

Endothelial Permeability after Treatment with BA-1049 (R) or BA-1049 (S)

Transvascular transport of labeled-albumin is used to study endothelial permeability. BA-1049 (R) and BA-1049 (S) are compared for their effect on repairing the blood-retinal barrier in a retinal model of extravasation. Extravasation in retina is detected after intravenous injection of a fluorescent tracer, albumin-FITC. This tracer is not normally able to traverse the blood-brain or blood-retinal barrier, but will leaky into the retina when there is detective endothelial cell permeability. Extravasation of the tracer can be detected in retinal whole mounts that allow visualization of the retinal vasculature.

To disrupt the blood-retinal barrier in adult rats, 4 µL of 10 µg of cell-permeable C3 transferase (Cytoskeleton, Inc., Denver Colo.) is injected into the left and right eyes of 8 Sprague Dawley rats after anesthetizing the rats with isoflurane. Intravitreal injection is into the posterior chamber using a 10 µl Hamilton syringe. Twenty-four hr later, 1 µM BA-1049 (R) is injected into the left eye of 4 rats, and of 1 µM of BA-1049 (S) is injected into the left eye of the remaining 4 rats. The right eye serves as an untreated control to detect extravasation induced by the high concentration of cell-permeable C3 transferase. Twenty-four hr later, fluorescein isothiocyanate (FITC, 300 µg/ml) tagged to bovine serum albumin (BSA, Sigma-Aldrich St. Louis, Mo.) is then injected intra-arterially (0.2 ml/100 g of body wt) and allowed to circulate for 10 min and then the eyes are removed for preparation of retinal whole mounts. The eyes are fixed in 4% paraformaldehyde in labelled tubes for 1 hr prior to preparation of whole mounts.

Retinal whole mounts are prepared by cutting around the sclera, and gently removing the lens. The eye is pinned on a wax plate is cut into 4 quadrants in the eye cup with single clean cuts. The flaps are pinned down, sticking the pins in the sclera, not the retina, and then the flaps are folded back to expose the retina. When all 4 are folded, the optic nerve is snipped at the fovea to release the retina from the optic nerve. Using a small paint brush to transfer the retina to a slide, it is placed ganglion cell layer up, attached to a filter paper and post-fixed (the eye curls naturally with the ganglion layer inside). The ganglion cell layer is kept up (the retina curls naturally with ganglion cell layer inside and the filter paper to fix it flat). The sample is post-fixed in 4% paraformaldehyde in phosphate buffer to flatten retina and rinsed overnight in PBS. The retina is teased away from the filter paper using a brush. Excess vitreous is blotted away with paper wicks. The slides are coverslipped and the FITC-labeled blood vessels are detected by epifluorescence microscopy.

The results show that BA-1049 (R) is able to reverse endothelial permeability and extravasation of FITC-BSA more effectively than BA-1049 (S).

The effect of BA-1049 (R) and BA-1076(S) on the tight junction protein occludin is also investigated in 4 rats. Occludin is downregulated in retinal endothelial cells in the first 24 hr after injection of cell-permeable C3 transferase. In four rats, cell-permeable C3 transferase is injected as above, and 24 hr later BA-1049 (R) or BA-1076(S) is injected as described above. Three days later the retinas are removed and processed for Western blotting for quantitative determination of occludin expression.

Loosening of the tight junctions leads to disruption in the blood retinal barrier and result in extravasations. Application of BA-1049 (R) restores the expression of occludin.

Example 21

Selective Deuteration of BA-1049R and Metabolites

Deuterium is a stable isotope of hydrogen, containing a single electron but with a nucleus containing one proton and one neutron. Consequently, deuterium has an atomic mass (AMU) of 2.0, whereas hydrogen, whose nucleus only contains one proton, is 1.0 AMU. The presence of deuterium in a carbon-deuterium bond, as opposed to a carbon-hydrogen bond, requires greater energy to cleave the bond and affects the pharmacokinetic profile of a compound, making a deuterated compound last longer. While selective deuteration of a compound may change its metabolism or half-life in the organism once administered, the compound is tested to make certain that a change in biologic behavior has been instilled by virtue of deuteration as compared to the non-deuterated compound.

Compounds can be deuterated using specialty deuterated chemical precursors, many of which are now commercially available, or through methods such as flow chemistry in the presence of $D_2O$ (Ötvös et al. (2011) *Molec. Diversity,* 15(3): 605-11).

The following experiment demonstrates the time course of the appearance and disappearance of BA-1049 (R) and 1-hydroxy-BA-1049 (R), as well as their deuterated counterparts, in rat plasma after oral and intravenous administration.

1. Animals and Dosing

Adult male, double jugular vein-cannulated Sprague-Dawley rats (Charles River Laboratories) are used in this study. Rats are dosed by either intravenous (IV) administration or oral (PO) administration. Rats dosed by IV receive a single dose of a 1:1 mixture of 1 mg/kg BA-1049 (R) and 1 mg/kg deuterated BA-1049 (R) via a surgically-implanted jugular vein cannula while rats dosed by PO receive a single 10 mg/kg dose of the 1:1 mixture of normal and deuterated compounds via oral gavage. Both doses are formulated in phosphate buffered saline (PBS). The presence of deuterium in place of hydrogen increases the mass of each ion by 1 AMU per site of exchange. Therefore, for example, if 4 sites were exchanged deuterium for hydrogen, the resulting deuterated ions would have a total mass that is 4 AMU higher.

Rats were monitored after administration for clinical signs of adverse effects of the administered compound.

After IV or PO dosing, blood samples are collected at 0.083 hr, 0.25 hr, 0.5 hr, 1 hr, 2 hr, 4 hr, 8 hr, 12 hr, 16 hr, and 24 hr. At each time point, 0.3 mL of blood is collected from a jugular vein cannula and placed in a tube containing dipotassium EDTA as an anticoagulant. Immediately after each blood sample collection, 0.3 mL of sterile 0.9% sodium chloride for Injection, USP is administered through the cannula to replace the collected blood volume. Blood samples are placed on ice until centrifuged. Samples are centrifuged and plasma pipetted to a new tube and placed on dry ice before being transferred to −80° C. for storage prior to further analysis.

2. Sample Analysis

Plasma samples are analyzed for determination of the plasma concentration of BA-1049 (R) and 1-hydroxy-BA- 1049 (R), and the deuterated equivalent of each. 25 µL of each sample of plasma, as well as standards and quality control (QC) samples are mixed with 200 µL internal standard solution containing 10 ng/mL propranolol in acetonitrile/methanol (50/50 v/v). The samples are vortexed and centrifuged at 4° C. 100 µL of the resulting supernatant is mixed with 300 µL of water/formic acid (100/0.1 v/v) and an aliquot is removed.

These samples are injected into an LC-MS/MS (liquid chromatography-tandem mass spectrometry) system for detection of BA-1049 (R) and 1-hydroxy-BA-1049 (R), and their deuterated forms.

3. Data Analysis

Plasma concentrations of the analytes are identified, averaged and plotted against time to determine various pharmacokinetic values such as the time course of appearance and disappearance (T1/2), the maximum concentration in plasma ($C_{max}$) and the time at which the plasma maximum occurs ($T_{max}$), and area under the concentration curve (AUC) as an indication of overall systemic exposure to the compounds.

4. Results

BA-1049 (R), 1-hydroxy-BA-1049 (R) and their deuterated counterparts are all detectable in blood plasma after either IV or PO administration, as is seen with the method represented in FIGS. 22A-22B. After administration of the BA-1049 (R) or its deuterated forms via IV dosing, the rate of time over which each form disappear from the plasma indicates how deuteration changes the metabolism or removal of BA-1049 (R) from the circulatory system. Administration via the oral route shows that the production of the 1-hydroxy-BA-1049 (R) and its deuterated form is detectable and the deuterated forms are likely to have different rates of disappearance from the circulation.

These results demonstrate that substitution of deuterium for hydrogen at different locations in the chemical structure of BA-1049 (R) or 1-hydroxy-BA-1049 (R) changes the rate at which both the deuterated form of BA-1049 (R) and 1-hydroxy-BA-1049 (R) disappear from the plasma after dosing. The results indicate that specific deuterated forms have a more advantageous pharmacokinetic profile and therefore longer-lasting effects to treat or manage diseases, disorders, or injuries.

Example 22

Ability of 1-Hydroxy-BA-1049 (R) Metabolite to Elicit Neurite Outgrowth

To determine if the 1-hydroxy-BA-1049 (R) metabolite is active in specific settings, a neurite outgrowth assay is used. Following the methods describe in EXAMPLE 9, BA-1049 (S), BA-1049 (R), and 1-hydroxy-BA-1049 to compare the ability of the different compounds to promote neurite outgrowth.

The 1-hydroxy metabolite of BA-1049 (R) stimulates neurite outgrowth at a lower concentration than any of the other test compounds.

Example 23

Kinase Inhibitory Screening of BA-1049 (R) and 1-Hydroxy-BA-1049 (R)

The following experiment demonstrates how BA-1049(R) and 1-hydroxy-BA-1049(R) were assessed by a kinome screen. The KINOMEscan™ screening platform (DiscoverX, Fremont, Calif.) employs a novel active site-directed competition binding assay to quantitatively measure interactions between test compounds and more than 450 human kinases and disease relevant mutant variants. These assays do not require ATP and thereby report true thermodynamic interaction affinities, as opposed to $IC_{50}$ values, which can depend on the ATP concentration. Compounds that bind the kinase active site and directly (sterically) or indirectly (allosterically) prevent kinase binding to the immobilized ligand, will reduce the amount of kinase captured on the solid support. Conversely, test molecules that do not bind the kinase have no effect on the amount of kinase captured on the solid support. Screening "hits" are identified by measuring the amount of kinase captured in test versus control samples by using a quantitative, precise and ultra-sensitive qPCR method that detects the associated DNA label.

Kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 µm) to remove cell debris. The remaining kinases were produced in HEK-293 cells and subsequently tagged with DNA for qPCR detection (Wein, et al. (2016) *Nat. Comm.* 7). Streptavidin-coated magnetic bead were treated with biotinylated small molecule ligands for 30 min at RT to generate affinity resins for kinase assays (Pegoraro, et al. (2017) *Nat. Comm.* 8). The liganded beads were blocked with excess biotin and washed with blocking buffer (SeaBlock, (Pierce Biochemical; Rockford, Ill.), 1% BSA, 0.05% Tween 20, 1 mM DTT) to remove unbound ligand and to reduce non-specific phage binding. Binding reactions were assembled by combining kinases, liganded affinity beads, and test compounds in 1× Binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.02 ml. The assay plates were incubated at RT with shaking for 1 hr, and the affinity beads were washed with Wash buffer (1×PBS, 0.05% Tween 20). The beads were then re-suspended in Elution buffer (1×PBS, 0.05% Tween 20, 0.5 µM non-biotinylated affinity ligand) and incubated at RT with shaking for 30 min. The kinase concentration in the eluates was measured by qPCR.

Table 17 shows study results for a 1-hydroxy-BA-1049 and BA-1049 screened against 468 kinases and for kinases implicated in cardiotoxicity.

TABLE 18

| | % Negative Binding | |
| Kinase | 1-Hydroxy BA-1049 (R) | BA-1049 (R) |
| --- | --- | --- |
| AMPK (1 and 2) | 100 | 95 |
| ALK | 81 | 94 |
| FGFR4 | 100 | 100 |
| IRAK3 | 96 | 92 |
| GCN | 96 | 99 |
| MARK1 | 69 | 67 |
| MARK2 | 100 | 100 |
| MARK3 | 81 | 100 |
| MARK4 | 92 | 94 |
| PRKCQ | 66 | 74 |
| MEK2 | 97 | 99 |
| MEK1 | 100 | 99 |
| SLK | 100 | 70 |
| ROCK1 | 0.15 | 0.65 |
| ROCK1 | 0.35 | 0.6 |

The values represent the percent of negative control binding (i.e. 100% equals no interference with binding by compound; significant binding is present when 30% or less of negative control is present). Neither compound interacted with biologically relevant affinity for any of the compounds. However, under these assay conditions they bind to both ROCK1 and ROCK2.

Example 24

Properties of the Adipate Salt of BA-1049(R)

BA-1049(R) is an ionizable compound which, when in the free base form, exists as a cation under the appropriate conditions and, forms a salt with an acceptable anion. The following salt screen was undertaken to identify appropriate counterions with which to pair the molecule so as to achieve good crystallinity and acceptable physicochemical properties. Formation of a crystal, with a stable lattice, can help to shield impurities from the drug substance crystal during production and also enhance its stability.
Experimental Method Approximately 100 mg of BA-1049(R) as the free base was dissolved in 2 mL of isopropyl alcohol followed by 0.5 mL of dichloromethane, and the solution stirred until the BA-1049(R) is completely dissolved. Either 1 molar equivalent or 0.5 molar equivalent amount of a pharmaceutically-acceptable counterion was added to the solution which was stirred at 68° C. for 2 hr to 6 hr to initiate the process of salt formation. Acceptable counterion include hydrochloride, tosylate, adipate, mesylate, D-tartrate, L-tartrate, fumarate, malate, maleate, mandelate, succinate, phosphate and others. The solution was cooled to RT with continuous stirring and the salt collected by filtration, and subsequently dried for further analysis of crystallinity and physical properties via X-ray powder diffraction (XRPD), water absorption by hygroscopicity, melting point and other physicochemical parameters.
Results A significant percentage of the tested counterions generated stable crystals with BA-1049(R) and were evaluated further using various means. Numerous different salt forms of BA-1049(R) showed substantial increases in melting temperature profiles, as compared to the free base, as determined by dynamic scanning calorimetry and were evaluated by thermogravimetric analysis (TGA) and dynamic vapor sorption (DVS).

Figure 27:
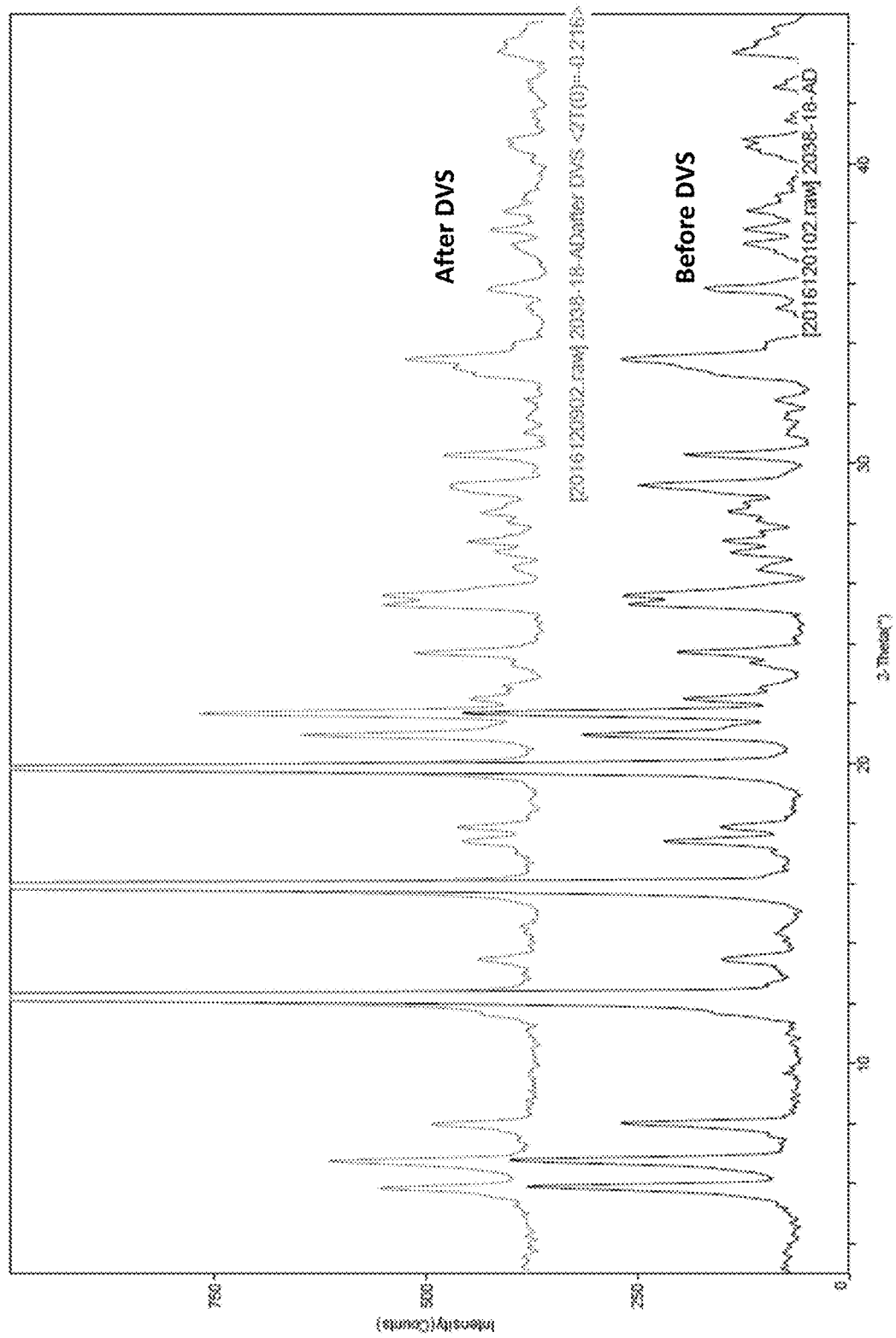
FIG. 27 is a graphic representation of X-Ray powder diffraction analysis traces of BA-1049 (R) adipate form before undergoing Dynamic Vapor Sorption (DVS) testing and after undergoing DVS testing, showing that exposure to humidity and then drying does not alter the crystal lattice as detected by X-Ray diffraction of BA-1049 (R) adipate.

While many of the salts that formed solids with good crystallinity by XRPD showed increased melting temperatures, their respective behaviors in DVS were different. Repeated cycles of humidification and de-humidification specifically identified the adipate salt as capable of absorbing small amounts of water vapor. As shown in FIG. 27, the BA-1049(R) adipate form was able to shed water upon drying, and did so without showing a change in the behavior of the crystal lattice, and to do so over multiple cycles of hydration followed by dehydration (FIG. 27). Coupled with the ability of the adipate salt to dissolve readily in water (>200 mg/mL at RT), while retaining low water content as a crystalline solid, these properties identified the adipate salt as a useful salt for therapeutic indications.

Example 25

Off-Target Safety Scan

Small molecule kinase inhibitors are targeted against a specific kinase or group of kinases. However, all kinase inhibitors display unintended off-target effects against other kinases, and they may also affect non-kinase targets. An example of off-target activity against non-kinase targets is the compound AR-13324 that also inactivates the norepinephrine transporter (NET) and the serotonin transporter (SERT) (Table 19) (Sturdivant et al. (2016) Bio-organic Med. Chem. Lett. 36: 2475). Part of the difficulty with off-target effects arises because many kinase inhibitors are synthesized to interfere directly or indirectly with the binding of adenosine triphosphate (ATP). A screen for off-target interactions between a kinase inhibitor and other targets can reveal if a kinase inhibitor has appropriate drug properties.

The following experiment identifies potential off-target interactions of either BA-1049(R) or 1-hydroxy-BA-1049 (R) using assays that measure the specific activities of selected cell surface targets on tissue culture cell lines or from purified enzymes. The SAFETYscan™ (DiscoverX) is used for rapid testing of any compound against a panel that includes well-known membrane proteins of importance for drug development such as selected voltage-gated ion channels, G-protein coupled receptors, neurotransmitter transporters and also a selected group of purified cellular enzymes.

Cell lines engineered to express individual transmembrane receptor proteins such as the muscarinic acetylcholine receptor or the dopamine D1 receptor were grown in culture in their standard growth medium until reaching confluence. BA-1049(R) and 1-hydroxy-BA-1049(R) were applied at 10 µM concentration and the cultures incubated for varying times until activity of the specific ion channel is measured using fluorescent reporters to assess activation or inhibition of the target ion channels or membrane transporters. The experiment also contains controls for comparison including known agonists and antagonists of the targeted membrane proteins.

For assays using purified enzymes, an enzyme assay is set up in standard reaction buffer and necessary indicators for activity such as co-factors, buffers and synthetic substrates. Activity assays are then undertaken in the presence or absence of 10 µM of either BA-1049(R) or 1-hydroxy-BA-1049(R) and the impact of their presence on enzyme activity is measured. As positive controls, a binding assay using Rho kinase (ROCK) was included in the panel. Other targets in the panel included G-protein coupled receptors, nuclear hormone receptors, intracellular non-kinase enzymes, ion channels, and neurotransmitter transporters. The specific targets were chosen because of their previous known associations with being the source of problematic off-target effects in cellular or whole animal studies.
Results As shown in Table 19, neither BA-1049 (R) nor 1-hydroxy-BA-1049(R) showed any significant impact on the two listed non-ROCK targets. Additionally, BA-1049(R) showed no activity against any of the targets in the total SAFETYscan™ with the exception for a potential antagonistic interaction with the 5-HT2b-receptor.

TABLE 19

% Inhibition of Neurotransmitter Transporter Activity

| Transporter | BA-1049(R) | 1-Hydroxy-BA-1049(R) | AR-13324 (Sturdivant et al., ibid.) |
|---|---|---|---|
| NET | 12% | 11% | 96% |
| SERT | 9% | 14% | 94% |

NET = norepinephrine transporter;
SERT = serotonin transporter

The absence of significant hits for either BA-1049(R) or for 1-hydroxy-BA-1049(R) provided clear evidence of the specificity of these compounds and their potential development to treat diseases, disorders or injuries.

Example 26

BA-1049(R) Improves Functional Recovery After Spinal Cord Injury the Effect of BA-1049(A) on Spinal Cord Injury The following experiment demonstrates the ability of BA-1049 (R) to improve functional recovery in mice after spinal cord injury (SCI).

1. Animals and Surgery

Adult female BALB/c mice (Charles River Laboratories) were used in this study. Mice received a dorsal overhemisection via the following method. Induction of anesthesia was accomplished by 5% isoflurane in 100% $O_2$. Mice remained anesthetized under 1-2% isoflurane in 100% $O_2$ for the rest of the surgery. Mice received Buprenorphine SR for pain relief. The mouse's back was shaved and sterilized with alternating 70% ethanol and povidone solution solutions. An incision was made above the lower thoracic spine. A laminectomy was performed at spinal level T9-T10. An 0.5 mm deep cut into and transversely across the dorsal spinal cord is made, accomplishing the dorsal overhemisection.

The muscles and skin were sutured and the mouse was supplied 0.9% sodium chloride solution to assist with fluid replenishment. The mice were provided water gel, softened food, normal mouse chow and water during their recovery. The mouse's bladder was expressed twice daily until they regain the ability to empty on their own. Mice were then weighed daily and monitored daily for clinical signs.

2. Dosing

SCI mice were randomly assigned to one of three groups: BA-1049 (R) treatment starting 2 d after surgery and continuing for 2 wk, BA-1049 (R) treatment starting 14 d after surgery and continuing 2 wk, and a control group receiving no BA-1049 (R).

Mice in treatment groups received 10 mg/kg intraperitoneal (IP) BA-1049 (R) in phosphate buffered saline (PBS) daily during the appropriate treatment period.

3. Behavioral Testing

At 28 d post-injury, mice from all 3 groups were graded by an experimenter masked to the identity of each mouse's treatment paradigm for performance on 2 behavioral tests. The first is a test of open-field locomotion and the second is a hindlimb grasping test in which the mouse is securely dangled with its hindlimbs near a thin, conical object such as a pencil. An uninjured mouse will reach out with its hindlimbs and grasp the object; the injured mice are graded on how similar their response it to that of an uninjured mouse.

The behavioral notes of the "masked" experimenter were consolidated by another scientist and the mice are ranked according to their performance on each test. After ranking, the identity of the mice were "unmasked."

4. Results

Figure 28:
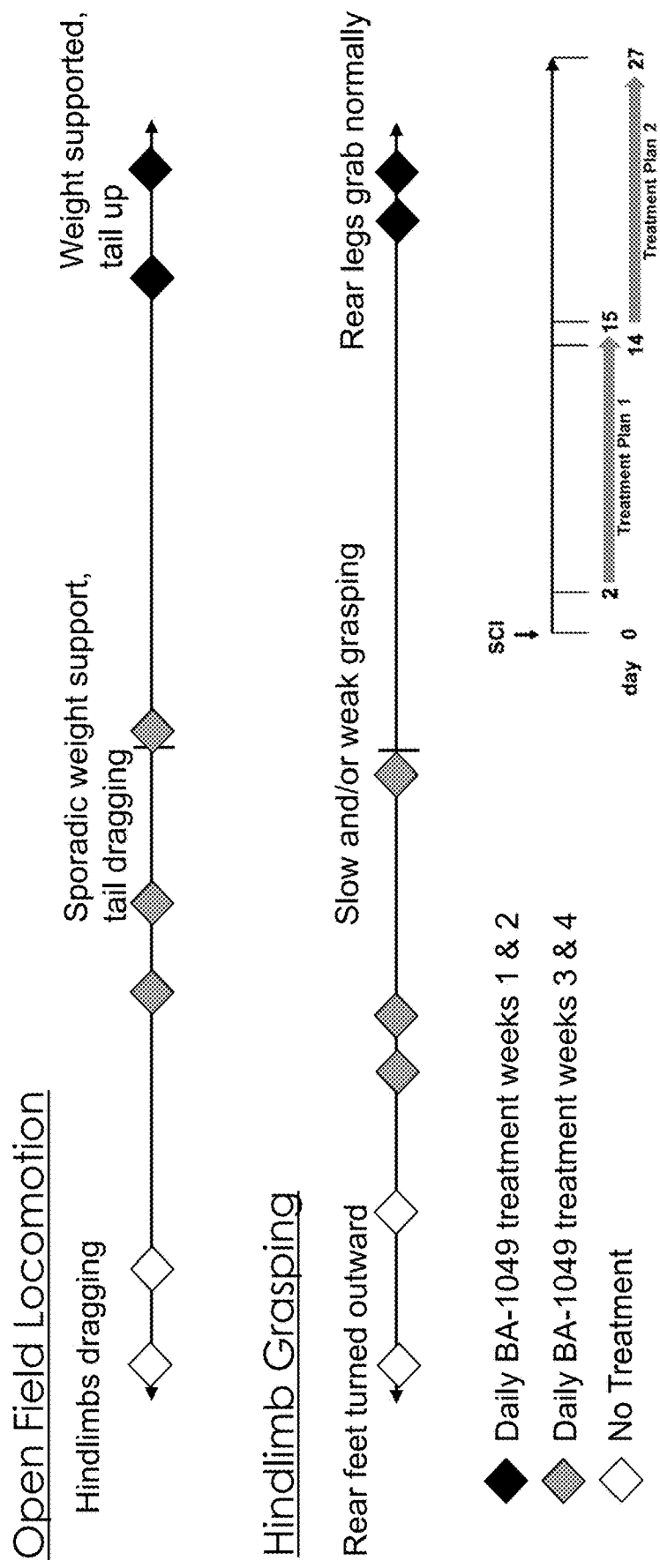
FIG. 28 is diagrammatic schematic representation showing the behavioral outcome measurements (open field locomotion and Hindlimb grasping) obtained from cohorts of SCI mice receiving no treatment, or either daily treatment with BA-1049 (R) for the first 2 weeks after injury, or received daily treatment with BA-1049 (R) for the $3^{rd}$ and $4^{th}$ weeks after injury.

Mice treated with 10 mg/kg IP BA-1049 (R) daily for the first 2 weeks after injury demonstrated performance on both behavioral tests closer to that of uninjured mice (FIG. 28). This recovery included weight-support on the hindlegs and tail elevation during open-field locomotion, as well as normal grasping with the rear legs during the grasping test. Mice receiving no BA-1049 (R) treatment demonstrated dragging rear hindlimbs during open-field locomotion and rear feet turned outward with no grasping during the grasping test. Injured mice receiving 10 mg/kg BA-1049 (R) intraperitoneally starting 14 d after injury and continuing 14 d demonstrated an intermediate recovery compared to the other groups; sporadic weight support in the open field and slow or weak grasping during the grasping test.

These results shown in FIG. 28 demonstrate that daily BA-1049 (R) induces significant locomotor and hindlimb motor control recovery after SCI. They also suggest that there may be a window for treatment after spinal cord injury, specifically, that treatment with BA-1049 (R) is more effective when administered early in the recovery versus starting at later time points.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of treating stroke in a patient suffering therefrom, the method comprising administering to the patient a therapeutically effective amount of a pharmaceutical formulation comprising a compound of the following structure:

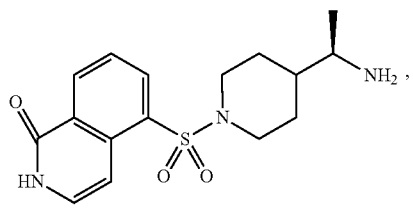 [SMILES: C[C@@H](N)C1CCN(S(=O)(=O)c2cccc3c(=O)[nH]ccc23)CC1]
or a salt thereof.
2. The method of claim 1, wherein the compound is deuterated.

SEQUENCE LISTING

```
<160> NUMBER OF SEQ ID NOS: 1

<210> SEQ ID NO 1
<211> LENGTH: 32
<212> TYPE: PRT
<213> ORGANISM: Artificial
<220> FEATURE:
<223> OTHER INFORMATION: Synthetic Peptide

<400> SEQUENCE: 1

Lys Glu Ala Lys Glu Lys Arg Gln Glu Gln Ile Ala Lys Arg Arg Arg
1               5                   10                  15

Leu Ser Ser Leu Arg Ala Ser Thr Ser Lys Ser Gly Gly Ser Gln Lys
            20                  25                  30
```